US012662484B2

(12) United States Patent
Wang et al.

(10) Patent No.: US 12,662,484 B2
(45) Date of Patent: Jun. 23, 2026

(54) SUBSTITUTED PIPERIDINES AS BRUTON'S TYROSINE KINASE INHIBITORS

(71) Applicant: Shenzhen TargetRx, Inc., Shenzhen (CN)

(72) Inventors: Yihan Wang, Shenzhen (CN); Qingfeng Xing, Shenzhen (CN)

(73) Assignee: Shenzhen TargetRx, Inc., Shenzhen (CN)

( * ) Notice: Subject to any disclaimer, the term of this patent is extended or adjusted under 35 U.S.C. 154(b) by 1169 days.

(21) Appl. No.: 17/510,815

(22) Filed: Oct. 26, 2021

(65) Prior Publication Data

US 2022/0041607 A1 Feb. 10, 2022

Related U.S. Application Data

(63) Continuation-in-part of application No. 16/325,114, filed as application No. PCT/CN2017/097633 on Aug. 16, 2017, now Pat. No. 11,186,578.

(30) Foreign Application Priority Data

Aug. 17, 2016 (CN) ......................... 201610683671.1

(51) Int. Cl.

| | |
|---|---|
| ***A61K 31/519*** | (2006.01) |
| ***A61K 9/00*** | (2006.01) |
| ***C07D 487/04*** | (2006.01) |

(52) U.S. Cl.

CPC .......... *C07D 487/04* (2013.01); *A61K 9/0053* (2013.01)

(58) Field of Classification Search

CPC ............................ A61K 31/519; C07D 487/04
USPC .................... 514/262.1, 265.1; 544/262, 280
See application file for complete search history.

(56) References Cited

U.S. PATENT DOCUMENTS

| | | | |
|---|---|---|---|
| 2008/0076921 A1 | 3/2008 | Honigberg et al. | |
| 2022/0041607 A1 | 2/2022 | Wang et al. | |

FOREIGN PATENT DOCUMENTS

| | | | |
|---|---|---|---|
| CN | 109851620 A | 6/2019 | |
| WO | WO 2010/126960 A1 | 11/2010 | |
| WO | WO-2016210165 A1 * | 12/2016 | .............. A61P 19/02 |
| WO | WO 2019/239374 A1 | 12/2019 | |
| WO | WO 2021/142257 A1 | 7/2021 | |

OTHER PUBLICATIONS

Jordan, V. C. Nature Reviews: Drug Discovery, 2, 2003, 205.*
Hackam, et al. JAMA, 296(14), 2006, 1731-1732.*
International Search Report and Written Opinion for Application No. PCT/CN2022/126956, mailed Dec. 27, 2022.

* cited by examiner

*Primary Examiner* — Douglas M Willis
(74) *Attorney, Agent, or Firm* — Wolf, Greenfield & Sacks, P.C.

(57) ABSTRACT

A fused bicyclic compound having an effect in inhibition of the activity of a tyrosine kinase, and preparation and use thereof are disclosed. In particular, a compound of formula (IV) or a pharmaceutically acceptable salt, a stereoisomer, a solvate, a hydrate, a polymorph, a prodrug or an isotopic variation thereof, as well as a pharmaceutical composition including the same are disclosed. As a selective irreversible inhibitor of Bruton's tyrosine kinase, the described compound can be used for preventing or treating diseases such as inflammation, autoimmune diseases (such as rheumatoid arthritis), xenogeneic immune diseases and cancers.

(IV)

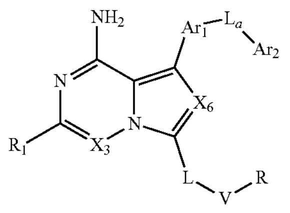

19 Claims, No Drawings

SUBSTITUTED PIPERIDINES AS BRUTON'S TYROSINE KINASE INHIBITORS

CROSS REFERENCE TO RELATED APPLICATIONS

The present application is a national application of PCT/CN2017/097633 filed on Aug. 16, 2017, which claims the priority of the Chinese Patent Application No. 201610683671.1 filed on Aug. 17, 2016. The Chinese Patent Application No. 201610683671.1 is incorporated herein by reference as part of the disclosure of the present application.

FIELD OF THE PRESENT DISCLOSURE

The disclosure belongs to the pharmaceutical field. In particular, the present disclosure relates to fused bicyclic compounds which have an inhibitory effect on protein tyrosine kinase activity, pharmaceutical compositions containing them, and processes for their preparation and use.

BACKGROUND OF THE PRESENT DISCLOSURE

Bruton's tyrosine kinase (BTK) belongs to the Tec tyrosine kinase family. BTK is mainly expressed in most hematopoietic cells (such as B cells, mast cells, and macrophages) and is present in bone marrow, spleen, and lymph node tissues. BTK plays an important role in B cell receptor (BCR) and FcR signaling pathways, which are involved in the development and differentiation of B cells. BTK can be activated by upstream Src family kinases. Once activated, BTK in turn phosphorylates PLCγ, which in turn affects B cell function and survival (Humphries et al., J. Biol. Chem. 279:37651, 2004). These signal paths must be precisely regulated. Mutations in the gene encoding BTK result in a human hereditary B cell-specific immunodeficiency disease, known as X-linked agammaglobulinemia (XLA). Abnormalities in BCR-mediated signaling may lead to dysregulation of B cell activation, leading to many autoimmune and inflammatory diseases. Preclinical studies have shown that BTK-deficient mice are resistant to the development of collagen-induced arthritis. In addition, clinical studies of Rituxan (CD20 antibody) for reducing mature B cells have shown that B cells play a key role in many inflammatory diseases such as rheumatoid arthritis, systemic lupus erythematosus, and multiple sclerosis.

In addition, abnormal activation of BTK plays an important role in the pathogenesis of B-cell lymphoma, which means that inhibition of BTK is useful in the treatment of hematological malignancies (Davis et al, Nature 463:88-92, 2010). Preliminary clinical trials have shown that Bruton's tyrosine kinase inhibitor PCI-32765 is effective in the treatment of several types of B-cell lymphoma. Since BTK acts as a mediator in multiple signal transduction pathways, BTK inhibitors have become hot spots as anti-inflammatory and/or anti-cancer drugs.

Ibrutinib (PCI-32765) is the first marketed BTK inhibitor in the world. On Nov. 13, 2013, the US Food and Drug Administration (FDA) approved use of Ibrutinib in the treatment of mantle cell lymphoma. In February 2014, the indication for chronic lymphocytic leukemia was added.

However, in order to optimize pharmacokinetics, prolong the drug resistance and reduce toxic side effects, it is necessary to further develop new BTK inhibitors.

Multiple sclerosis (MS) is a chronic, inflammatory, demyelmating, and degenerative disease of the CNS that affects approximately 900,000 people in the United States (Wallin et al. 2019) and 2.3 million worldwide (GBD 2016 Multiple Sclerosis Collaborators 2019). It is primarily a disease of young adults, with 70%-80% of patients having an age of onset (i.e., initial clinical presentation to a physician) between 20 and 40 years (Anderson et al. 1992; Noonan et al. 2002) and has a gender bias influenced by the phenotype, with approximately up to 64%-70% of diagnosed patients being women (Anderson et al. 1992; Noonan et al. 2002).

MS is mainly classified into three clinical phenotypes, one of which is primary progressive (PPMS). PPMS is further subdivided into active and non-active forms based on the presence or absence of disease activity, defined by the presence of clinical relapses and/or gadolinium-enhancing lesions on T1-weighted magnetic resonance imaging (MRI) scan (TIGd+) or new/enlarging T2-weighted lesions on MRI scan.

Even though there are many drugs currently available that target the pathological inflammatory mechanisms associated with relapses and relapse-associated worsening, currently only one is indicated for PPMS. As a result, the salient feature of disability progression in ail forms of MS remains under addressed, and treatments that can stop or delay MS disease progression represent a serious unmet medical need.

SUMMARY OF THE PRESENT DISCLOSURE

The present disclosure provides a novel fused bicyclic compound and a composition comprising the same and use thereof. The compounds have better BTK kinase inhibitory activity and/or better pharmacodynamic/pharmacokinetic properties (especially better metabolic stability) and can be used to treat, prevent, and alleviate diseases mediated by BTK kinase.

Thus, the Present Disclosure Adopts the Following Technical Solutions:

In the first aspect, the present disclosure provides a fused bicyclic compound represented by formula (I):

(I)

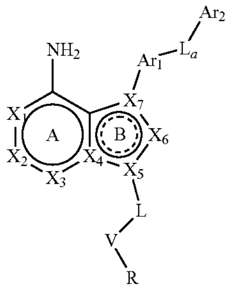

wherein, ring A is aromatic ring, ring B is aromatic ring or non-aromatic ring;

$X_1$ to $X_7$ are independently selected from C or N atom, wherein, when $X_1$, $X_2$, $X_3$ and $X_6$ are C atoms, they are each optionally substituted by $R_1$; and when $X_6$ is C atom, it may be in the oxidative form of —C(═O)—;

wherein, each $R_1$ is independently selected from H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, —$OR_{1a}$, —$N(R_{1a})_2$, —$SR_{1a}$, —$Si(R_{1a})_3$, —C(═O)$R_{1a}$, —C(═O)$OR_{1a}$, —C(═O)$N(R_{1a})_2$, —$NR_{1a}$C(═O)$R_{1a}$, —$NR_{1a}$C(═O)$OR_{1a}$, —$NR_{1a}$C(═O)N$(R_{1a})_2$, —OC(═O)$R_{1a}$, —OC(═O)$OR_{1a}$ or —OC(═O)$N(R_{1a})_2$, wherein each $R_{1a}$ is independently selected from H, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl, or two $R_{1a}$ groups together form substituted or unsubstituted $C_3$-$C_7$ heterocyclyl or substituted or unsubstituted $C_5$-$C_{10}$ heteroaryl;

$Ar_1$ is ring C of the following formula:

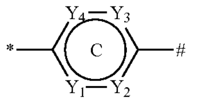

wherein, $Y_1$ to $Y_4$ are independently selected from C or N atom, wherein, when $Y_1$ to $Y_4$ are C atoms, they are each optionally substituted by $R_2$;

wherein each $R_2$ is independently selected from H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, —$OR_{2a}$, —$N(R_{2a})_2$, —$SR_{2a}$, —$Si(R_{1a})_3$, —C(═O)$R_{2a}$, —C(═O)$OR_{2a}$, —C(═O)$N(R_{2a})_2$, —$NR_{2a}$C(═O)$R_{2a}$, —$NR_{2a}$C(═O)$OR_{2a}$, —$NR_{2a}$C(═O)N$(R_{2a})_2$, —OC(═O)$R_{2a}$, —OC(═O)$OR_{2a}$ or —OC(═O)$N(R_{2a})_2$, wherein each $R_{2a}$ is independently selected from H, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, or two $R_{2a}$ groups together form substituted or unsubstituted $C_3$-$C_7$ heterocyclyl or substituted or unsubstituted $C_5$-$C_{10}$ heteroaryl;

or, $Y_1$, $Y_2$ together with their substituent $R_2$ form substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

wherein * represents the bond connects with $X_7$, # represents the bond connects with $L_a$;

$L_a$ is selected from a bond, O, S, $NR_3$, $C(R_3)_2$, C(═O), C(═O)O, OC(═O), C(═O)$NR_3$, $NR_3$C(═O), $NR_3$C(═O)$NR_3$, OC(═O)$NR_3$, $NR_3$C(═O)O, S(═O)$_m$, S(═O)$_m$$NR_3$, $NR_3$S(═O)$_m$, $NR_3$S(═O)$_m$$NR_3$, OP(═O)$_m$$R_3$, P(═O)$_m$$OR_3$, wherein, each $R_3$ is independently selected from H, OH, halo, CN, $NO_2$, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, or two $R_3$ groups together form substituted or unsubstituted $C_3$-$C_7$ heterocyclyl or substituted or unsubstituted $C_5$-$C_{10}$ heteroaryl, m is 1 or 2;

$Ar_2$ is substituted or unsubstituted $C_6$-$C_{10}$ aryl or substituted or unsubstituted $C_5$-$C_{10}$ heteroaryl;

L is selected from substituted or unsubstituted $C_1$-$C_6$ alkyl, substituted or unsubstituted $C_1$-$C_6$ heteroalkyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

V is selected from a bond, C(═O), C(═O)O, OC(═O), C(═O)$NR_4$, $NR_4$C(═O), $NR_4$C(═O)$NR_4$, OC(═O)$NR_4$, $NR_4$C(═O)O, S(═O)$_n$, S(═O)$_n$$NR_4$, $NR_4$S(═O)$_n$, $NR_4$S(═O)$_n$$NR_4$, OP(═O)$_n$$R_4$, P(═O)$_n$$OR_4$, wherein, each $R_4$ is selected from H, OH, halo, CN, $NO_2$, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl, or two $R_4$ groups together form substituted or unsubstituted $C_3$-$C_7$ heterocyclyl or substituted or unsubstituted $C_5$-$C_{10}$ heteroaryl, n is 1 or 2;

R is CN, or $C_2$-$C_6$ alkenyl or $C_2$-$C_6$ alkynyl that are optionally substituted by 0, 1, 2 or 3 $R_5$ substituents, wherein, $R_5$ is selected from H, OH, halo, CN, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

or a pharmaceutically acceptable salt, a stereoisomer, a solvate, a hydrate, a polymorph, a prodrug or an isotopic variants thereof.

In another aspect, the present disclosure provides a fused bicyclic compound of formula (IV),

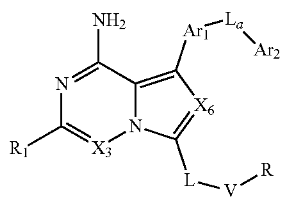

(IV)

or a pharmaceutically acceptable salt, stereoisomer, or tautomer thereof, wherein:

$Ar_1$ is ring C of the formula:

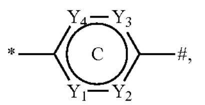

wherein:

$Y_1$ is $CR_2$ or N;

$Y_2$ is $CR_2$ or N;

$Y_3$ is $CR_2$ or N;

$Y_4$ is $CR_2$ or N;

each $R_2$ is independently H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, $—OR_{2a}$, $—N(R_{2a})_2$, $—SR_{2a}$, $—Si(R_{2a})_3$, $—C(=O)R_{2a}$, $—C(=O)OR_{2a}$, $—C(=O)N(R_{2a})_2$, $—NR_{2a}C(=O)R_{2a}$, $—NR_{2a}C(=O)OR_{2a}$, $—NR_{2a}C(=O)N(R_{2a})_2$, $—OC(=O)R_{2a}$, $—OC(=O)OR_{2a}$ or $—OC(=O)N(R_{2a})_2$, wherein each $R_{2a}$ is independently H, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, or two $R_{2a}$ groups together form substituted or unsubstituted $C_3$-$C_7$ heterocyclyl or substituted or unsubstituted $C_5$-$C_{10}$ heteroaryl;

or, $Y_1$, $Y_2$ together with their substituent $R_2$ form substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

* is the point of attachment to the carbon atom of the bicyclic ring; and

\# is the point of attachment to $L_a$;

$Ar_2$ is substituted or unsubstituted $C_6$-$C_{10}$ aryl or substituted or unsubstituted $C_5$-$C_{10}$ heteroaryl;

L is:

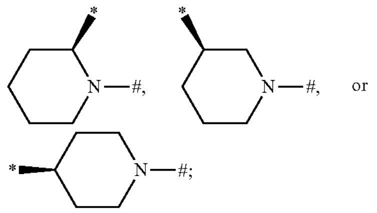

wherein:

* is the point of attachment to the carbon atom of the bicyclic ring; and

\# is the point of attachment to V;

$L_a$ is a bond, —O—, —S—, $—NR_3—$, $—C(R_3)_2—$, —C(=O)—, —C(=O)O—, —OC(=O)—, $—C(=O)NR_3—$, $—NR_3C(=O)—$, $—NR_3C(=O)NR_3—$, $—OC(=O)NR_3—$, $—NR_3C(=O)O—$, $—S(=O)_m—$, $—S(=O)_mNR_3—$, $—NR_3S(=O)_m—$, $—NR_3S(=O)_mNR_3—$, $—OP(=O)_mR_3—$, $—P(=O)_mOR_3—$, wherein, each $R_3$ is H, OH, halo, CN, $NO_2$, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, or two $R_3$ groups together form substituted or unsubstituted $C_3$-$C_7$ heterocyclyl or substituted or unsubstituted $C_5$-$C_{10}$ heteroaryl, m is 1 or 2;

V is a bond, —C(=O)—, —C(=O)O—, —OC(=O)—, $—C(=O)NR_4—$, $—NR_4C(=O)—$, $—NR_4C(=O)NR_4—$, $—OC(=O)NR_4—$, $—NR_4C(=O)O—$, —S(=O), —, $—S(=O)_nNR_4—$, $—NR_4S(=O)_n—$, $—NR_4S(=O)_nNR_4—$, $—OP(=O)_nR_4—$, $—P(=O)_nOR_4—$, wherein, each $R_4$ is H, OH, halo, CN, $NO_2$, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl, or two $R_4$ groups together form substituted or unsubstituted $C_3$-$C_7$ heterocyclyl or substituted or unsubstituted $C_5$-$C_{10}$ heteroaryl, n is 1 or 2;

$X_3$ is $CR_1$ or N;

$X_6$ is $CR_1$ or N;

R is CN, or $C_2$-$C_6$ alkenyl or $C_2$-$C_6$ alkynyl that are optionally substituted by 0, 1, 2 or 3 $R_5$ substituents, wherein, $R_5$ is selected from H, OH, halo, CN, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

each $R_1$ is independently H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, $—OR_{1a}$, $—N(R_{1a})_2$, $—SR_{1a}$, $—Si(R_{1a})_3$, $—C(=O)R_{1a}$, $—C(=O)OR_{1a}$, $—C(=O)N(R_{1a})_2$, $—NR_{1a}C(=O)R_{1a}$, $—NR_{1a}C(=O)OR_{1a}$, $—NR_{1a}C(=O)N(R_{1a})_2$, $—OC(=O)R_{1a}$, $—OC(=O)OR_{1a}$ or $—OC(=O)N(R_{1a})_2$, wherein each $R_{1a}$ is independently H, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl, or two $R_{1a}$ groups together form substituted or unsubstituted $C_3$-$C_7$ heterocyclyl or substituted or unsubstituted $C_5$-$C_{10}$ heteroaryl.

In another aspect, the disclosure provides a pharmaceutical composition comprising a compound disclosed herein and a pharmaceutically acceptable excipient. In a particular embodiment, the compound disclosed herein is provided in the pharmaceutical composition in an effective amount. In a particular embodiment, the compound disclosed herein is provided in a therapeutically effective amount. In a particular embodiment, the compound disclosed herein is provided in a prophylactically effective amount.

In another aspect, the disclosure provides a pharmaceutical composition comprising a compound disclosed herein and a pharmaceutically acceptable excipient, further comprising other therapeutic agents.

In another aspect, the disclosure provides a kit containing a compound, or a pharmaceutically acceptable salt, a stereoisomer, a solvate, a hydrate, a polymorph, a prodrug or an isotopic variants thereof, and other therapeutic agents, and pharmaceutically acceptable carriers, adjuvants or vehicles.

In another aspect, the disclosure provides a method of treating BTK mediated diseases in a subject in need thereof, the method comprising: administering to the subject an effective amount of a compound disclosed herein. In a specific embodiment, the BTK mediated disease is selected from the group consisting of allergic disease, autoimmune disease, inflammatory disease, or cancer. In a specific embodiment, the disease is selected from the following: multiple sclerosis, relapsing multiple sclerosis, relapsing-remitting multiple sclerosis, progressive multiple sclerosis, secondary-progressive multiple sclerosis, primary-progressive multiple sclerosis, and progressive-relapsing multiple sclerosis.

In a specific embodiment, the BTK mediated disease is B cell proliferative disorder, including, but not limited to, chronic lymphocytic lymphoma, non-Hodgkin's lymphoma, diffuse large B-cell lymphoma, mantle cell lymphoma, follicular lymphoma and chronic lymphocytic leukemia.

In a specific embodiment, the compound is administered orally, subcutaneously, intravenously or intramuscularly. In a specific embodiment, the compound is administered chronically.

Other objects and advantages of the present disclosure will be apparent to those skilled in the art from the specific embodiments, examples and claims.

Definitions

Chemical Definitions

Definitions of specific functional groups and chemical terms are described in more detail below.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$ and $C_5$-$C_6$ alkyl.

It should be understood that when described herein any of the moieties defined forth below may be substituted with a variety of substituents, and that the respective definitions are intended to include such substituted moieties within their scope as set out below. Unless otherwise stated, the term "substituted" is to be defined as set out below.

"$C_1$-$C_6$ alkyl" (also represented as $C_{1-6}$ alkyl) refers to a straight-chain or branched saturated hydrocarbon group having from 1 to 6 carbon atoms, and it is also referred to herein as "lower alkyl". In some embodiments, $C_1$-$C_4$ alkyl is particularly preferred. Examples of alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_1$-$C_6$ alkyl (e.g., —$CH_3$). In certain embodiments, the alkyl group is substituted $C_1$-$C_6$ alkyl.

"$C_2$-$C_6$ alkenyl" refers to a straight-chain or branched hydrocarbon group having from 2 to 6 carbon atoms, one or more carbon-carbon double bonds (e.g., 1, 2, or 3 carbon-carbon double bonds). The one or more carbon-carbon double bonds can be internal (such as in 2-butenyl) or terminal (such as in 1-butenyl). In some embodiments, $C_2$-$C_4$ alkenyl is particularly preferred. Examples of alkenyl groups include, but are not limited to, ethenyl ($C_2$), 1-propenyl ($C_3$), 2-propenyl ($C_3$), 1-propen-2-yl ($C_3$), 1-butenyl ($C_4$), 2-butenyl ($C_4$), butadienyl ($C_4$), pentenyl ($C_5$), pentadienyl ($C_5$), hexenyl ($C_6$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_2$-$C_6$ alkenyl. In certain embodiments, the alkenyl group is substituted $C_2$-$C_6$ alkenyl.

"$C_2$-$C_6$ alkynyl" refers to a straight-chain or branched hydrocarbon group having from 2 to 6 carbon atoms, one or more carbon-carbon triple bonds (e.g., 1, 2, or 3 carbon-carbon triple bonds), and optionally one or more carbon-carbon double bonds (e.g., 1, 2, or 3 carbon-carbon double bonds). In some embodiments, $C_2$-$C_4$ alkynyl is particularly preferred. In certain embodiments, alkynyl does not contain any double bonds. The one or more carbon-carbon triple bonds can be internal (such as in 2-butynyl) or terminal (such as in 1-butynyl). Examples of the alkynyl groups include, without limitation, ethynyl ($C_2$), 1-propynyl ($C_3$), 2-propynyl ($C_3$), 1-butynyl ($C_4$), 2-butynyl ($C_4$), pentynyl ($C_5$), 3-methylbut-1-ynyl ($C_5$), hexynyl ($C_6$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_2$-$C_6$ alkynyl. In certain embodiments, the alkynyl group is substituted $C_2$-$C_6$ alkynyl.

"$C_1$-$C_6$ heteroalkyl" refers to an alkyl group, as defined herein, which further contains one or more (e.g., 1, 2, 3 or 4) heteroatoms (e.g., oxygen, sulfur, nitrogen, boron, silicon, phosphorus) in the parent carbon chain, wherein one or more heteroatoms are between adjacent carbon atoms in the parent carbon chain, and/or one or more heteroatoms are between the carbon atom and the parent molecule, that is, between the connection points. Unless otherwise stated, each heteroalkyl group is independently substituted, i.e., unsubstituted ("unsubstituted heteroalkyl") or substituted with one or more substituents ("substituted heteroalkyl"). In some embodiments, a heteroalkyl group is an unsubstituted $C_1$-$C_6$ heteroalkyl group. In some embodiments, a heteroalkyl group is a substituted $C_1$-$C_6$ heteroalkyl group. As a specific example, the $C_1$-$C_6$ heteroalkyl group includes $C_1$-$C_6$ alkoxy group, $C_1$-$C_6$ alkylthio group, $C_1$-$C_6$ alkylamino group and the like, which are defined in details as follows.

"$C_1$-$C_6$ alkoxy" refers to the group —OR wherein R is a substituted or unsubstituted $C_1$-$C_6$ alkyl group. In some embodiments, $C_1$-$C_4$ alkoxy group is particularly preferred. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy.

"$C_1$-$C_6$ alkylthio" refers to the group-SR wherein R is optionally substituted $C_1$-$C_6$ alkyl. In some embodiments, $C_1$-$C_4$ alkylthio group is particularly preferred. Specifically, the $C_1$-$C_6$ alkylthio group includes, but is not limited to, methylthio, ethylthio, n-propylthio, isopropylthio, n-butylthio, tert-butylthio, sec-butylthio, n-pentylthio, n-hexylthio and 1,2-dimethylbutylthio.

"$C_1$-$C_6$ alkylamino" refers to the group —NHR or —$NR_2$, wherein R is optionally substituted $C_1$-$C_6$ alkyl. In some embodiments, $C_1$-$C_4$ alkylamino group is particularly preferred. Specifically, the $C_1$-$C_6$ alkylamino group includes, but is not limited to, methylamino, ethylamino, n-propylamino, isopropylamino, n-butylamino, t-butylamino, dimethylamino, methylethylamino and diethylamino.

"$C_1$-$C_6$ acyl" refers to the group —(=O)R, wherein R is optionally substituted $C_1$-$C_6$ alkyl. In some embodiments, $C_1$-$C_4$ acyl group is particularly preferred. Exemplary $C_1$-$C_6$ acyl groups include, but are not limited to, —(=O) $CH_3$, —(=O) $CH_2CH_3$, —(=O) $CH_2CH_2CH_3$ and —(=O)CH $(CH_3)_2$.

"Halo" or "halogen" means fluorine (F), chlorine ($C_1$), bromine (Br) and iodine (I). In some embodiments, the halo group is F, —Cl or Br. In some embodiments, the halogen group is F or Cl. In some embodiments, the halogen group is F.

Thus, "$C_1$-$C_6$ haloalkyl" and "$C_1$-$C_6$ haloalkoxy" refer to the above "$C_1$-$C_6$ alkyl" and "$C_1$-$C_6$ alkoxy", which are substituted by one or more halo groups. In some embodiments, $C_1$-$C_4$ haloalkyl group is particularly preferred, and more preferably $C_1$-$C_2$ haloalkyl group. In some embodiments, $C_1$-$C_4$ haloalkoxy group is particularly preferred, and more preferably $C_1$-$C_2$ haloalkoxy group. Exemplary haloalkyl groups include, but are not limited to, —$CF_3$, —$CH_2F$, —$CHF_2$, —$CHFCH_2F$, —$CH_2CHF_2$, —$CF_2CF_3$, —$CCl_3$, —$CH_2Cl$, —$CHCl_2$, 2,2,2-trifluoro-1,1-dimethyl-ethyl, and the like. Exemplary haloalkoxy groups include, but are not limited to: —$OCH_2F$, —$OCHF_2$, —$OCF_3$, and the like.

"$C_3$-$C_7$ carbocyclyl" refers to a non-aromatic cyclic hydrocarbon group having from 3 to 7 ring carbon atoms and zero heteroatoms. In some embodiments, $C_5$-$C_6$ carbocyclyl is preferred, which is a non-aromatic cyclic hydrocarbon group having from 5 to 6 ring carbon atoms and zero heteroatoms. In some embodiments, $C_4$ carbocyclyl is preferred, which is a non-aromatic cyclic hydrocarbon group having 4 ring carbon atoms and zero heteroatoms. In some embodiments, $C_5$ carbocyclyl is preferred, which is a non-aromatic cyclic hydrocarbon group having 5 ring carbon atoms and zero heteroatoms. In some embodiments, $C_6$ carbocyclyl is preferred, which is a non-aromatic cyclic hydrocarbon group having 6 ring carbon atoms and zero heteroatoms. Carbocyclyl also includes ring systems wherein the carbocyclyl ring, as defined above, is fused, bridged or spiro-connected with one or more carbocyclyl, heterocyclyl, aryl or heteroaryl groups wherein the point of attachment is on the carbocyclyl ring, and in such instances, the number of carbons continue to designate the number of carbons in the carbocyclic ring system. Exemplary carbocyclyl groups include, but is not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cyclohexadienyl ($C_6$), as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo [2.2.2]octanyl ($C_8$), and the like. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_3$-$C_7$ carbocyclyl. In certain embodiments, the carbocyclyl group is a substituted $C_3$-$C_7$ carbocyclyl.

"$C_3$-$C_7$ heterocyclyl" refers to a radical of a 3- to 7-membered non-aromatic ring system having ring carbon atoms and 1 to 3 ring heteroatoms, wherein each heteroatom is independently selected from nitrogen, oxygen, sulfur, boron, phosphorus, and silicon, wherein the carbon, nitrogen, sulfur and phosphorus atoms may be present in the oxidation state, such as C(O), S(O), $S(O)_2$, P(O), and the like. In heterocyclyl groups that contain one or more nitrogen atoms, the point of attachment can be a carbon or nitrogen atom, as valency permits. In some embodiments, $C_4$-$C_7$ heterocyclyl is preferred, which is a radical of a 4- to 7-membered non-aromatic ring system having ring carbon atoms and 1 to 3 ring heteroatoms. In some embodiments, $C_4$-$C_6$ heterocyclyl is preferred, which is a radical of a 4- to 6-membered non-aromatic ring system having ring carbon atoms and 1 to 3 ring heteroatoms. In some embodiments, $C_5$-$C_6$ heterocyclyl is preferred, which is a radical of a 5- to 6-membered non-aromatic ring system having ring carbon atoms and 1 to 3 ring heteroatoms. In some embodiments, $C_5$ heterocyclyl is preferred, which is a radical of a 5-membered non-aromatic ring system having ring carbon atoms and 1 to 3 ring heteroatoms. In some embodiments, the above mentioned heterocyclyl contain 1 to 3 (more preferably 1 or 2) ring heteroatoms selected from nitrogen, oxygen and sulfur (preferably nitrogen and oxygen). Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted $C_3$-$C_7$ heterocyclyl. In certain embodiments, the heterocyclyl group is substituted $C_3$-$C_7$ heterocyclyl. Heterocyclyl also includes ring systems wherein the heterocyclyl ring, as defined above, is fused, bridged or spiro-connected with one or more carbocyclyl, heterocyclyl, aryl or heteroaryl groups, wherein the point of attachment is on the heterocyclyl ring; and in such instances, the number of ring members continue to designate the number of ring members in the heterocyclyl ring system. Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxathiolanyl, oxathiolyl (1,2-oxathiolyl, 1,3-oxathiolyl), dithiolanyl, dihydropyrazolyl, dihydroimidazolyl, dihydrothiazolyl, dihydroisothiazolyl, dihydrooxazolyl, dihydroisoxazolyl, dihydrooxadiazolyl and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, tetrahydropyridinyl, and thianyl. Exemplary 6-membered heterocyclyl groups containing two heteroatoms include, without limitation, dihydropyrazinyl, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one or two heteroatoms include, without limitation, azepanyl, diazepanyl, oxepanyl and thiepanyl. Exemplary 5-membered heterocyclyl groups fused to a 6-membered aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an 6-membered aryl ring (also referred to herein as a 6,6-bicyclic heterocyclic ring) include, without limitation, tetrahydroquinolinyl, tetrahydroisoquinolinyl, and the like.

"$C_6$-$C_{10}$ aryl" refers to a radical of a monocyclic or polycyclic (e.g., bicyclic or tricyclic) 4n+2 aromatic ring system (e.g., having 6, 10 $\pi$ electrons shared in a cyclic array) having 6-10 ring carbon atoms and zero heteroatoms provided in the aromatic ring system. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). "$C_6$-$C_{10}$ aryl" also includes ring systems wherein the aryl ring, as defined above, is fused with one or more carbocyclyl, heterocyclyl, aryl or heteroaryl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, piceno, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-10}$ aryl. In certain embodiments, the aryl group is substituted $C_{6-10}$ aryl.

"$C_5$-$C_{10}$ heteroaryl" refers to a radical of a 5-10 membered monocyclic or bicyclic 4n+2 aromatic ring system (e.g., having 6 or 10 $\pi$ electrons shared in a cyclic array) having ring carbon atoms and 1-4 ring heteroatoms provided in the aromatic ring system, wherein each heteroatom is independently selected from nitrogen, oxygen and sulfur. In some embodiments, $C_5$ heteroaryl is preferred, which is a radical of a 5-membered monocyclic 4n+2 aromatic ring system (e.g., having 6 $\pi$ electrons shared in a cyclic array) having ring carbon atoms and 1-4 ring heteroatoms, wherein each heteroatom is independently selected from nitrogen, oxygen and sulfur. In some embodiments, $C_6$ heteroaryl is preferred, which is a radical of a 6-membered monocyclic 4n+2 aromatic ring system (e.g., having 6 $\pi$ electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings. Heteroaryl includes ring systems wherein the heteroaryl ring, as defined above, is fused with one or more carbocyclyl, heterocyclyl, aryl or heteroaryl groups wherein the point of attachment is on the heteroaryl ring, and in such instances, the number of ring members continue to designate the number of ring members in the heteroaryl ring system. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted $C_5$-$C_{10}$ heteroaryl. In certain embodiments, the heteroaryl group is substituted $C_5$-$C_{10}$ heteroaryl. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, alkenyl, alkynyl, carbocyclyl, heterocyclyl, aryl, and heteroaryl groups, as defined herein, are optionally substituted groups. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary substituents on carbon atom include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR)R^{bb}$, —SH, —$SR^{aa}$, —$SSR^{cc}$, —$C(=O)R^{aa}$, —$CO_2H$, —CHO, —$C(OR)_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C$ (=$NR^{bb}$)$N(R^{bb})_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —$Si(R^{aa})_3$, —$OSi(R^{aa})_3$—C(=S)$N(R^{bb})_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)$_2R^{aa}$, —OP(=O)$_2R^{aa}$, —P(=O)$(R^{aa})_2$, —OP(=O)$(R^{aa})_2$, —OP(=O)$(OR)_2$, —P(=O)$_2N(R^{bb})_2$, —OP(=O)$_2N(R^{bb})_2$, —P(=O)$(NR^{bb})_2$, —OP(=O)$(NR^{bb})_2$, —$NR^{bb}$P(=O)$(OR^{cc})_2$, —$NR^{bb}$P(=O)$(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, alkyl, haloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted with 0, 1, 2, 3, 4, or 5 $R_{dd}$ groups;

or two geminal hydrogens on a carbon atom are replaced with the group =O, =S, =$NN(R^{bb})_2$, =$NNR^{bb}$C(=O)$R^{aa}$, =$NNR^{bb}$C(=O)$OR^{aa}$, =$NNR^{bb}$S(=O)$_2R^{aa}$, =$NR^{bb}$, or =$NOR^{cc}$;

each instance of $R^{aa}$ is, independently, selected from alkyl, haloalkyl, alkenyl, alkynyl, carbocyclyl, heterocyclyl, aryl, and heteroaryl, or two $R^{aa}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(=O)$R^{aa}$, —C(=O)$N(R^{cc})_2$, —$CO_2R^{aa}$, —$SO_2R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R)_2$, —C(=O)$SR^{cc}$, —C(=S)$SR^{cc}$, —P(=O)$_2R^{aa}$, —P(=O)$(R^{aa})_2$, —P(=O)$_2N(R^{cc})_2$, —P(=O)$(NR^{cc})_2$, alkyl, haloalkyl, alkenyl, alkynyl, carbocyclyl, heterocyclyl, aryl, and heteroaryl, or two $R^{bb}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, alkyl, haloalkyl, alkenyl, alkynyl, carbocyclyl, heterocyclyl, aryl, and heteroaryl, or two Rec groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —C(=O)$R^{ee}$, —$CO_2H$, —$CO_2R^{ee}$, —OC(=O)$R^{ee}$, —$OCO_2R^{ee}$, —C(=O)$N(R^{ff})_2$, —OC(=O)$N(R^{ff})_2$, —$NR^{ff}$(=O)$R^{ee}$, —$NR^{ff}CO_2R^{ee}$, —$NR^{cc}$(=O)$N(R^{ff})_2$, —C(=$NR^{ff}$)$OR^{ee}$, —OC(=$NR^{ff}$)$R^{ee}$, —OC(=$NR^{ff}$)$OR^{ee}$, —C(=$NR^{ff}$)$N(R^{ff})_2$, —OC(=$NR^{ff}$)$N(R^{ff})_2$, —$NR^{ee}$C(=$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(=O)$R^{ee}$, —$Si(R^{ee})_3$, —$OSi(R^{ee})_3$, —C(=S)$N(R^{ff})_2$, —C(=O)$SR^{ee}$, —C(=S)$SR^{ee}$, —SC(=S)$SR^{ee}$, —P(=O)$_2R^{ee}$, —P(=O)$(R^{ee})_2$, —OP(=O)$(R^{ee})_2$, —OP(=O)$(OR^{ee})_2$, alkyl, haloalkyl, alkenyl, alkynyl, carbocyclyl, heterocyclyl, aryl, heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from alkyl, haloalkyl, alkenyl, alkynyl, carbocyclyl, aryl, heterocyclyl, and heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, alkyl, haloalkyl, alkenyl, alkynyl, carbocyclyl, heterocyclyl, aryl and heteroaryl, or two $R^{ff}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2$ $(C_{1-6}$ alkyl$)^+X^-$, —$NH_3^+X^-$, —$N(OC_{1-6}$ alkyl)$(C_{1-6}$ alkyl), —N(OH)$(C_{1-6}$ alkyl), —NH(OH), —SH, —$SC_{1-6}$ alkyl, —SS$(C_{1-6}$ alkyl), —C(=O)$(C_{1-6}$ alkyl), —$CO_2H$, —$CO_2$ $(C_{1-6}$ alkyl), —OC(=O)$(C_{1-6}$ alkyl), —$OCO_2(C_{1-6}$ alkyl), —C(=O)$NH_2$, —C(=O)$N(C_{1-6}$ alkyl$)_2$, —OC(=O)$NH(C_{1-6}$ alkyl), —NHC(=O)$(C_{1-6}$ alkyl), —$N(C_{1-6}$ alkyl) C(=O)$(C_{1-6}$ alkyl), —$NHCO_2$ $(C_{1-6}$ alkyl), —NHC(=O)$N(C_{1-6}$ alkyl$)_2$, —NHC(=O)$NH(C_{1-6}$ alkyl), —NHC(=O)$NH_2$, —C(=NH)$O(C_{1-6}$ alkyl), —OC(=NH)$(C_{1-6}$ alkyl), —OC(=NH)$OC_{1-6}$ alkyl, —C(=NH)$N(C_{1-6}$ alkyl$)_2$, —C(=NH)$NH(C_{1-6}$ alkyl), —C(=NH)$NH_2$, —OC(=NH)$N(C_{1-6}$ alkyl$)_2$, —OC(NH)$NH(C_{1-6}$ alkyl), —OC(NH)$NH_2$, —NHC(NH)$N(C_{1-6}$ alkyl$)_2$, —NHC(=NH)$NH_2$, —$NHSO_2$ $(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$—C(=S)$N(C_{1-6}$ alkyl$)_2$, C(=S)$NH(C_{1-6}$ alkyl), C(=S)$NH_2$, —C(=O)$S(C_{1-6}$ alkyl), —C(=S)$SC_{1-6}$ alkyl, —SC(=S)$SC_{1-6}$ alkyl, —P(=O)$_2$ $(C_{1-6}$ alkyl), —P(=O)$(C_{1-6}$ alkyl$)_2$, —OP(=O)$(C_{1-6}$ alkyl$)_2$, —OP(=O)$(OC_{1-6}$ alkyl$)_2$, $C_{1-6}$ alkyl, $C_{1-6}$ perhaloalkyl, $C_2$-$C_6$ alkenyl, $C_2$-$C_6$ alkynyl, $C_3$-$C_7$ carbocyclyl, $C_6$-$C_{10}$ aryl, $C_3$-$C_7$ heterocyclyl, $C_5$-$C_{10}$ heteroaryl; or two geminal $R^{gg}$ substituents can be joined to form =O or =S; wherein $X^-$ is a counterion.

Exemplary substituents on nitrogen atoms include, but are not limited to, hydrogen, —OH, —$OR^{aa}$, —$N(R)_2$, —CN, —C(=O)$R^{aa}$, —C(=O)$N(R)_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, —P(=O)$_2R^{aa}$, —P(=O)$(R^{aa})_2$, —P(=O)$_2N(R^{cc})_2$, —P(=O)$(NR^{cc})_2$, alkyl, perhaloalkyl, alkenyl, alkynyl, carbocyclyl, heterocyclyl, aryl, and heteroaryl, or two $R^{cc}$ groups attached to a nitrogen atom are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and inorganic and organic bases. Examples of pharmaceutically acceptable, nontoxic acid addition salts are salts of inorganic acids such as hydrochloric acid, hydrobromic acid, phosphoric acid, sulfuric acid and perchloric acid or salts of organic acids such as acetic acid, oxalic acid, maleic acid, tartaric acid, citric acid, succinic acid or malonic acid. Also included herein is the salt formed by using the conventional methods in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or elderly adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutically effective amount and prophylactically effective amount.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

The "Expanded Disability Status Scale" (EDSS) is a ClinRO measure for quantifying changes in the disability level of a subject with MS overtime. The EDSS is based on a standard neurological examination, incorporating functional systems (visual, brainstem, pyramidal, cerebellar, sensory, bowel and bladder, and cerebral [or mental]) that are rated and then scored as a functional system score (FSS), and ambulation, which is scored as ambulation score. Each FSS is an ordinal clinical rating scale ranging from 0 to 5 or 6, and an ambulation score that is rated from 0 to 12. These ratings may then be used in conjunction with observations, as well as information, concerning ambulation and use of assistive devices to determine the total EDSS score. The EDSS is a disability scale that ranges in 0.5-point steps from 0 (normal) to 10.0 (death)(Kurtzke 1983; Kappos 2011). In some embodiments of the methods provided herein, the item sexual dysfunction and fatigue are not included in the EDSS score.

The "9-Hole Peg Test" (9-HPT) is a quantitative measure of upper extremity (arm and hand) function (Goodkin et al. 1988; Fischer et al. 2001). The test device consists of a container with nine pegs and a block containing nine empty holes. The subject is to pick up each of the nine pegs one at a time and as quickly as possible place them in the nine holes. Once all the pegs are in the holes, the subject is to remove them again one at a time as quickly as possible and replace them into the container. The total time to complete the task is recorded. Both the dominant and non-dominant hands are tested twice (two successfully completed trials of the dominant hand, followed immediately by two successfully completed trials of the non-dominant hand). The two trials for each hand are averaged, converted to the reciprocals of the mean times for each hand, and the two reciprocals are averaged. The 9-HPT may be administered, for example, as described in the Multiple Sclerosis Functional Composite (MSFC) Administration and Scoring Manual (Fischer et al., 2001). A meaningful change in upper extremity function may, for example, be indicated by a 20% worsening from baseline of the averaged 9-HPT times.

The "Timed 25-Foot Walk Test" (T25FWT) is a quantitative measure of mobility and leg function, based on a timed 25-foot walk. The subject is directed to start at one end of a clearly marked 25-foot course and is instructed to walk 25 feet as quickly and safely as possible, and how long it takes the subject to go from start of the walk to the end of the 25 feet is timed. In some embodiments, the task is administered immediately again by having the subject walk back the same distance, and the time for both completed trials averaged to produce the score for the T25FWT. Subjects may use assistive devices (e.g., cane or wheelchair) when performing the task. The T25FWT may be administered, for example, as described in the MSFC Administration and Scoring Manual (Fischer et al., 2001) A clinically meaningful change in mobility and leg function may, for example, be indicated by a 20% worsening from baseline of the averaged T25FWT time.

"Confirmed Disability Progression" (CDP) refers to an increase in the subject's EDSS score that is sustained over a particular time period. This may be evaluated, for example, by calculating the subject's EDSS score, determining that the score is increased over a previous score (such as a baseline score, which may be a score taken before the subject began administration of the present compound or a pharmaceutically acceptable salt thereof), and then confirming the score is still increased after a specified period of time has elapsed from the initial increase (e.g., by reevaluating the subject and recalculating it again). For example, a 12-week confirmed disability progression (CDP12) refers to an EDSS score that remains increased at least 12 weeks after the initial increase (e.g., as confirmed by recalculating the EDSS score at least 12 weeks after the initial increase). A 24-week confirmed disability progression (CDP24) refers to an EDSS score remains increased at least 24 weeks after the initial increase (e.g., as confirmed by recalculating the EDSS score at least 24 weeks after the initial increase). The initial increase may be compared to a baseline EDSS score (such as prior to beginning administration with the present compound or a pharmaceutically acceptable salt thereof), or may be compared to a prior EDSS score that had remained stable over time, such as over 12, 24, 36, 48, or 60 weeks. In some embodiments, a CDP refers to an increase of ≥1.0 point from the baseline EDSS score in a subject with a baseline EDSS score of ≤5.5 points, or an increase of ≥0.5 point from the baseline EDSS score in a subject with a baseline EDSS score of ≥5.5 points. Time to onset of a CDP (e.g., time to onset of CDP12 or CDP24) refers to the time period from when the prior EDSS score was established (for example, a baseline EDSS score from before beginning administration of the present compound or a pharmaceutically acceptable salt thereof) until the sustained increase of EDSS score is observed.

"Composite Confirmed Disability Progression" (cCDP) is a composite measure of disability progression using a combination of EDSS, 9-HPT, and T25FWT. It evaluates the progression of subject's disability over a particular time period as determined by the first occurrence of a progression event. A progression event may include any one of the following: a CDP (e.g., increase of ≥1.0 point from the baseline EDSS score in a subject with a baseline EDSS score of ≤5.5 points, or an increase of ≥0.5 point from the baseline EDSS score in a subject with a baseline EDSS score of ≥5.5 points); an increase of ≥20% from baseline in time to complete the 9-Hole Peg Test (9-HPT); or an increase of ≥20% from baseline in the Timed 25-Foot Walk Test (T25FWT); wherein the occurrence of the progression event is confirmed at after a specified period of time has elapsed from the initial occurrence. For example, a composite 12-week continued disability progression (cCDP12) refers to the occurrence of at least one progression event at an initial time point, and the same progression event is confirmed at least 12 weeks later (e.g., by re-evaluating the subject using the same test). A composite 24-week confirmed disability progression (cCDP12) refers to the occurrence of at least one progression event at an initial time penod, and same progression event is confirmed at least 24 weeks later. Time to onset of a cCDP (e.g., time to onset of cCDP12 or cCDP24) refers to the time period from when the prior evaluation scores were established (for example, baseline scores before beginning administration of the present compound or a pharmaceutically acceptable salt thereof) until the initial progression event is observed. Without wishing to be bound by theory, compared with endpoints based exclusively on the Expanded Disability Status Scale (EDSS), which emphasizes lower limb function, the cCDP12 requires at least one of the following: 1) an increase in EDSS score of ≥1.0 point from a baseline (BL) score of ≤5.5 points, or ≥0.5 point increase from a BL score of ≥5.5 points (Confirmed Disability Progression); 2) a 20% increase from BL in time to complete the 9-Hole Peg Test; 3) a 20% increase from BL in the Timed 25-Foot Walk Test. Thus, the cCDP 12 is a more sensitive assessment of disability, especially at early disease stages. The use of the cCDP 12 as a primary outcome may provide a clearer, more complete picture of disability progression or improvement than the EDSS alone.

"Combination" and related terms mean the simultaneous or sequential administration of a compound and other therapeutic agent of the present disclosure. For example, a compound disclosed herein may be administered simultaneously or sequentially with another therapeutic agent in separate unit dosage forms, or together with another therapeutic agent in a single unit dosage form.

The compounds disclosed herein can be used to treat or prevent diseases mediated by Bruton's Tyrosine Kinase (BTK). BTK mediated diseases as used herein, mean any disease state or other deleterious condition in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that can be treated or prevented with the compounds disclosed herein include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), autoimmune hematologic disorders (e.g. hemolytic anemia, aplastic anemia, idiopathic thrombocytopenia, and neutropenia), autoimmune gastritis, and autoimmune inflammatory bowel diseases (e.g. ulcerative colitis and Crohn's disease), host versus graft disease, allograft rejection, chronic thyroiditis, Graves' disease, scleroderma, diabetes (type I and type II), active hepatitis (acute and chronic), pancreatitis, primary biliary cirrhosis, myasthenia gravis, multiple sclerosis, systemic lupus erythematosis, psoriasis, atopic dermatitis, contact dermatitis, eczema, skin sunburns, vasculitis (e.g. Behcet's disease), chronic renal insufficiency, Stevens-Johnson syndrome, inflammatory pain, idiopathic sprue, cachexia, sarcoidosis, Guillain-Barre syndrome, uveitis, conjunctivitis, kerato conjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that can be treated or prevented include, among others, allergies to foods, food additives, insect poisons, dust mites, pollen, animal materials and contact allergens, type I hypersensitivity allergic asthma, allergic rhinitis, allergic conjunctivitis.

Infectious diseases that can be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that can be treated or prevented include, among others, osteoporosis, osteoarthritis, traumatic arthritis, gouty arthritis and bone disorders related with multiple myeloma.

Proliferative diseases that can be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell.

DETAILED DESCRIPTION OF THE EMBODIMENTS

Compound

In the present disclosure, "compound disclosed herein" refers to the following compound of formula (I), or a pharmaceutically acceptable salt, a stereoisomer, a solvate, a hydrate, a polymorph, a prodrug or an isotopic variants thereof.

In one embodiment, the present disclosure relates to a compound of formula (I):

(I)

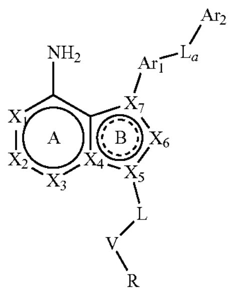

wherein, ring A is aromatic ring, ring B is aromatic ring or non-aromatic ring;

$X_1$ to $X_7$ are independently selected from C or N atom, wherein, when $X_1$, $X_2$, $X_3$ and $X_6$ are C atoms, they are each optionally substituted by $R_1$; and when $X_6$ is C atom, it may be in the oxidative form of —C(=O)—;

wherein, each $R_1$ is independently selected from H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, $—OR_{1a}$, $—N(R_{1a})_2$, $—SR_{1a}$, $—Si(R_{1a})_3$, $—C(=O)R_{1a}$, $—C(=O)OR_{1a}$, $—C(=O)N(R_{1a})_2$, $—NR_{1a}C(=O)R_{1a}$, $—NR_{1a}C(=O)OR_{1a}$, $—NR_{1a}C(=O)N(R_{1a})_2$, $—OC(=O)R_{1a}$, $—OC(=O)OR_{1a}$ or $—OC(=O)N(R_{1a})_2$, wherein each $R_{1a}$ is independently selected from H, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl, or two $R_{1a}$ groups together form substituted or unsubstituted $C_3$-$C_7$ heterocyclyl or substituted or unsubstituted $C_5$-$C_{10}$ heteroaryl;

$Ar_1$ is ring C of the following formula:

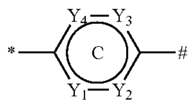

wherein, $Y_1$ to $Y_4$ are independently selected from C or N atom, wherein, when $Y_1$ to $Y_4$ are C atoms, they are each optionally substituted by $R_2$;

wherein each $R_2$ is independently selected from H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, $—OR_{2a}$, $—N(R_{2a})_2$, $—SR_{2a}$, $—Si(R_{1a})_3$, $—C(=O)R_{2a}$, $—C(=O)OR_{2a}$, $—C(=O)N(R_{2a})_2$, $—NR_{2a}C(=O)R_{2a}$, $—NR_{2a}C(=O)OR_{2a}$, $—NR_{2a}C(=O)N(R_{2a})_2$, $—OC(=O)R_{2a}$, $—OC(=O)OR_{2a}$ or $—OC(=O)N(R_{2a})_2$, wherein each $R_{2a}$ is independently selected from H, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, or two $R_{2a}$ groups together form substituted or unsubstituted $C_3$-$C_7$ heterocyclyl or substituted or unsubstituted $C_5$-$C_{10}$ heteroaryl;

or, $Y_1$, $Y_2$ together with their substituent $R_2$ form substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

wherein * represents the bond connects with $X_7$, # represents the bond connects with $L_a$;

$L_a$ is selected from a bond, O, S, $NR_3$, $C(R_3)_2$, C(=O), C(=O)O, OC(=O), $C(=O)NR_3$, $NR_3C(=O)$, $NR_3C$ (=O)$NR_3$, OC(=O)$NR_3$, $NR_3$C(=O)O, S(=O)$_m$, S(=O)$_m$$NR_3$, $NR_3$S(=O)$_m$, $NR_3$S(=O)$NR_3$, OP(=O)$_m$$R_3$, P(=O)$_m$$OR_3$, wherein, each $R_3$ is independently selected from H, OH, halo, CN, $NO_2$, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, or two $R_3$ groups together form substituted or unsubstituted $C_3$-$C_7$ heterocyclyl or substituted or unsubstituted $C_5$-$C_{10}$ heteroaryl, m is 1 or 2;

$Ar_2$ is substituted or unsubstituted $C_6$-$C_{10}$ aryl or substituted or unsubstituted $C_5$-$C_{10}$ heteroaryl;

L is selected from substituted or unsubstituted $C_1$-$C_6$ alkyl, substituted or unsubstituted $C_1$-$C_6$ heteroalkyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

V is selected from a bond, C(=O), C(=O)O, OC(=O), C(=O)$NR_4$, $NR_4$C(=O), $NR_4$C(=O)$NR_4$, OC(=O)$NR_4$, $NR_4$C(=O)O, S(=O)$_n$, S(=O)$_n$$NR_4$, $NR_4$S(=O)$_n$, $NR_4$S(=O)$_n$$NR_4$, OP(=O)$_n$$R_4$, P(=O)$_n$$OR_4$, wherein, each $R_4$ is independently selected from H, OH, halo, CN, $NO_2$, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl, or two $R_4$ groups together form substituted or unsubstituted $C_3$-$C_7$ heterocyclyl or substituted or unsubstituted $C_5$-$C_{10}$ heteroaryl, n is 1 or 2;

R is CN or $C_2$-$C_6$ alkenyl or $C_2$-$C_6$ alkynyl that are optionally substituted by 0, 1, 2 or 3 $R_5$ substituents, wherein, $R_5$ is selected from H, OH, halo, CN, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

or a pharmaceutically acceptable salt, a stereoisomer, a solvate, a hydrate, a polymorph, a prodrug or an isotopic variants thereof.

Preferably, in the above mentioned embodiment, the compound is a compound of formula (II):

(II)

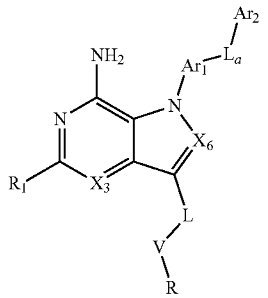

wherein, $X_3$, $X_6$, $R_1$, $Ar_1$, $L_a$, $Ar_2$, L, V and R are as defined above.

Preferably, in the above mentioned embodiment, the compound is the following compound:

(IIa)

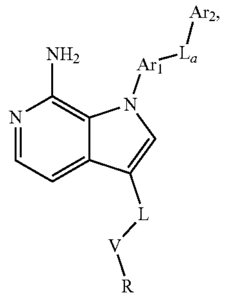

(IIb)

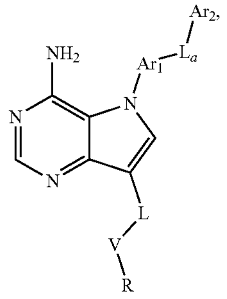

(IIc)

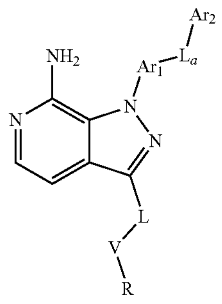

or (IId)

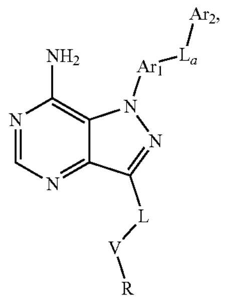

wherein, $Ar_1$, $L_a$, $Ar_2$, L, V and R are as defined above.

Preferably, in the above mentioned embodiment, at least one of $Y_1$ to $Y_4$ is N atom, and the others are C atoms; or, preferably, in the above mentioned embodiment, $Y_1$ to $Y_4$ are all C atoms; and when they are C atoms, each of them is optionally substituted by $R_2$; preferably, $Ar_1$ is selected from the following groups:

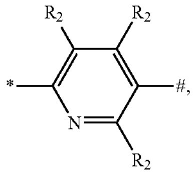

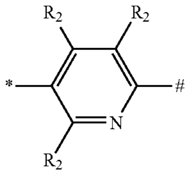

or

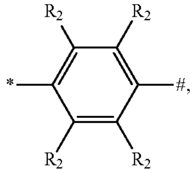

wherein, $R_2$ is independently selected from H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl; preferably, $R_2$ is independently selected from H, OH, halo, CN, $NO_2$, substituted or unsubstituted $C_1$-$C_6$ alkyl or substituted or unsubstituted $C_1$-$C_6$ heteroalkyl; preferably, $R_2$ is independently selected from H, OH, halo or CN; preferably, $R_2$ is independently selected from H or halo, preferably, $R_2$ is H.

Preferably, in the above mentioned embodiment, $L_a$ is selected from a bond, O, S, $NR_3$, $C(R_3)_2$, C(=O), C(=O)O, OC(=O), C(=O)$NR_3$, $NR_3$C(=O), $NR_3$C(=O)$NR_3$, OC(=O)$NR_3$, $NR_3$C(=O)O, $S(=O)_m$, $S(=O)_m NR_3$, $NR_3 S(=O)_m$ or $NR_3 S(=O)_m NR_3$; preferably, $L_a$ is selected from a bond, O, S, $NR_3$, $C(R_3)_2$, C(=O), C(=O)O, OC(=O), C(=O)$NR_3$, $NR_3$C(=O), $NR_3$C(=O)$NR_3$, OC(=O)$NR_3$ or $NR_3$C(=O)O; preferably, $L_a$ is selected from a bond, O, S, $NR_3$, $C(R_3)_2$, C(=O), C(=O)O, OC(=O), C(=O)$NR_3$ or $NR_3$C(=O); preferably, $L_a$ is selected from O, S, $NR_3$, $C(R_3)_2$ or C(=O)$NR_3$; preferably, $L_a$ is selected from O or C(=O)$NR_3$; preferably, $L_a$ is O;

wherein, each $R_3$ is independently selected from H, OH, halo, CN, $NO_2$, substituted or unsubstituted $C_1$-$C_6$ acyl or substituted or unsubstituted $C_1$-$C_6$ alkyl; preferably, $R_3$ is independently selected from H, OH, halo, CN or $NO_2$; preferably, $R_3$ is independently selected from H, OH, F, Cl or Br; preferably, $R_3$ is H or F;

m is 1 or 2.

Preferably, in the above mentioned embodiment, $Ar_2$ is unsubstituted $C_6$-$C_{10}$ aryl or unsubstituted $C_5$-$C_{10}$ heteroaryl; preferably, $Ar_2$ is phenyl or pyridinyl.

Preferably, in the above mentioned embodiment, L is selected from substituted or unsubstituted $C_1$-$C_6$ alkyl, substituted or unsubstituted $C_1$-$C_6$ heteroalkyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

preferably, L is selected from $C_1$-$C_6$ alkyl, substituted or unsubstituted $C_1$-$C_6$ heteroalkyl, substituted or unsubstituted $C_3$-$C_7$ carbocyclyl or substituted or unsubstituted $C_3$. —$C_7$ heterocyclyl;

preferably, L is selected from substituted or unsubstituted $C_5$-$C_6$ heterocyclyl;

preferably, L is selected from the following groups:

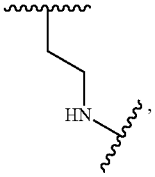, 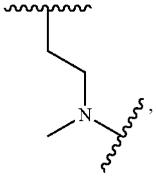, 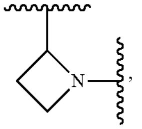,

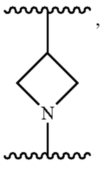, 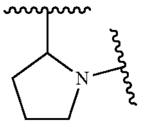, 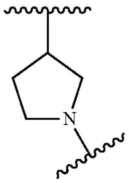,

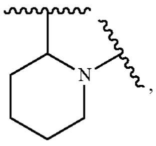, 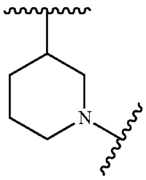, 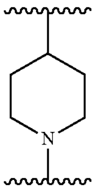,

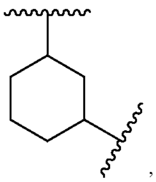, 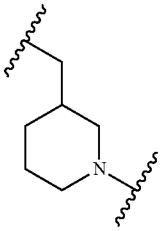, 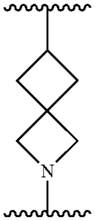,

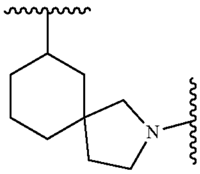, 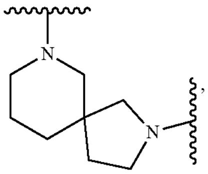,

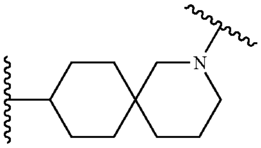, 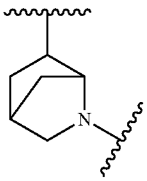,

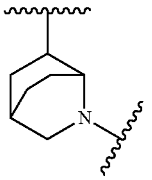 or 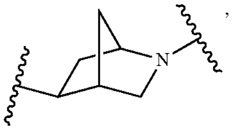, preferably. L is selected from the following groups:

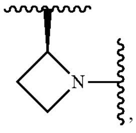, 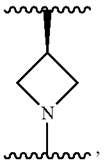, 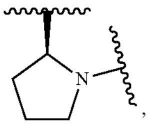,

-continued

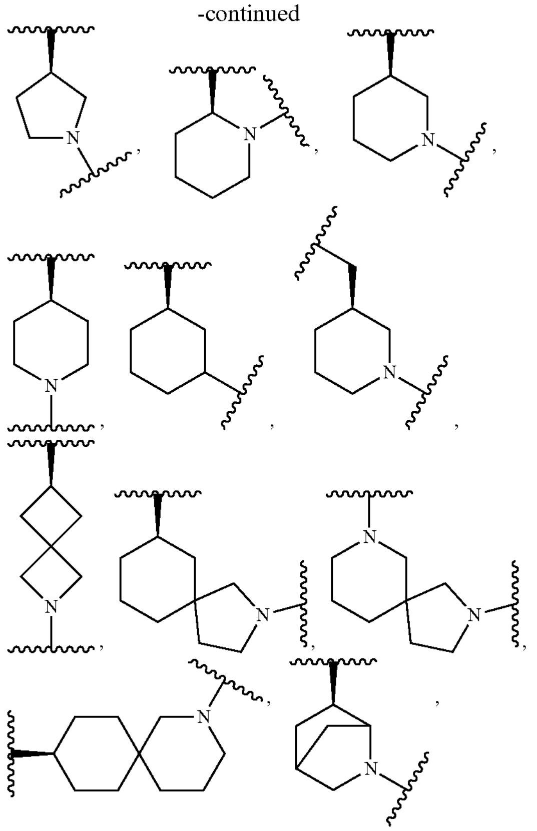

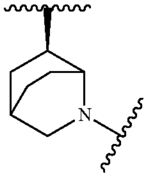

or

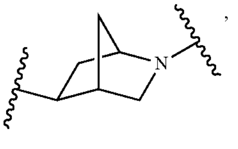

wherein ⌇ represents the connection position between $X_5$ of the parent core and V.

Preferably, in the above mentioned embodiment. V is selected from a bond. C(═O), C(═O)O, OC(═O), C(═O)$NR_4$, $NR_4C$(═O)$NR_4C$(═O)$NR_4$, OC(═O)$NR_4$, $NR_4C$(═O)O, S(═O)$_n$, S(═O)$_n NR_4$, $NR_4S$(═O)$_n$, $NR_4S$(═O)$_n NR_4$, OP(═O)$_n R_4$ or P(═O)$_n OR_4$; preferably, V is selected from a bond, C(═O), C(═O)O, OC(═O), C(═O)$NR_4$, $NR_4C$(═O), $NR_4C$(═O)$NR_4$, OC(═O)$NR_4$, $NR_4C$(═O)O, S(═O)$_n$, S(═O)$_n NR_4$, $NR_4S$(═O), or $NR_4S$(═O)$_n NR_4$; preferably, V is selected from a bond, C(═O), C(═O)O, OC(═O), C(═O)$NR_4$, $NR_4C$(═O), $NR_4C$(═O)$NR_4$, OC(—O)$NR_4$ or $NR_4C$(═O)O; preferably, V is selected from a bond, C(═O), C(═O)O, OC(═O), C(═O)$NR_4$ or $NR_4C$(═O); preferably, V is selected from a bond or C(═O); preferably, V is C(═O);

wherein, each $R_4$ is selected from H, OH, halo, CN, $NO_2$, substituted or unsubstituted $C_1$-$C_6$ acyl or substituted or unsubstituted $C_1$-$C_6$ alkyl; preferably, $R_4$ is independently selected from H or substituted or unsubstituted $C_1$-$C_6$ alkyl;

n is 1 or 2.

Preferably, in the above mentioned embodiment, R is CN, or $C_2$-$C_6$ alkenyl or $C_2$-$C_6$ alkynyl that are optionally substituted by 0 or 1 $R_5$ substituents; preferably, R is $C_2$-$C_6$ alkenyl or $C_2$-$C_6$ alkynyl that are optionally substituted by 0 or 1 $R_5$ substituents; preferably, R is $C_2$-$C_6$ alkenyl that is optionally substituted by 0 or 1 $R_5$ substituents; preferably, R is unsubstituted vinyl;

$R_5$ is selected from H, OH, halo, CN, substituted or unsubstituted $C_1$-$C_6$ alkyl or substituted or unsubstituted $C_1$-$C_6$ heteroalkyl; preferably, $R_5$ is selected from H, CN, substituted or unsubstituted $C_1$-$C_6$ alkyl or substituted or unsubstituted $C_1$-$C_6$ heteroalkyl;

preferably, in the above mentioned embodiment, R is selected from the following groups:

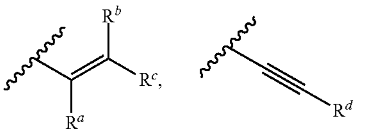

or

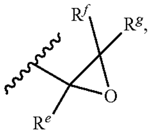

wherein, each $R^a$, $R^b$, $R^c$, $R^d$, $R^e$, $R^f$ and $R^{gg}$ is selected from the above $R_5$;

preferably, R is selected from the following groups:

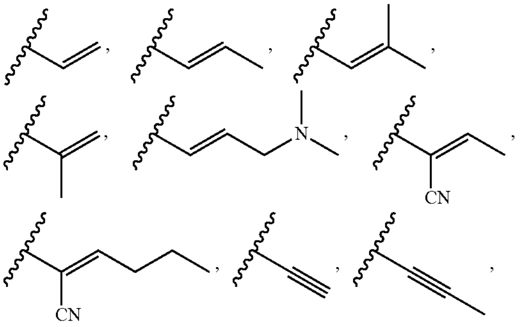

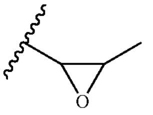

or

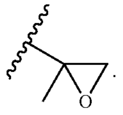

Preferably, in the above mentioned embodiment, the compound is a compound of formula (III):

(III)

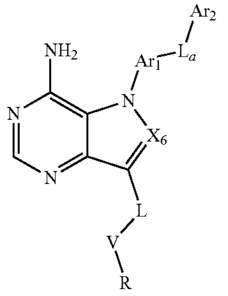

wherein.

-L-V—R is selected from:
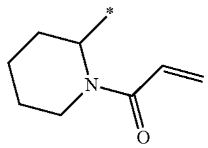,
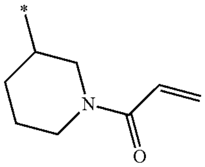,
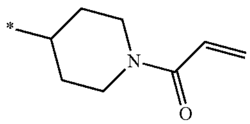,
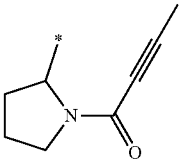
or
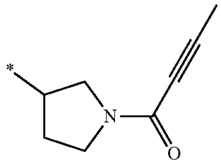
;
preferably, -L-V—R is selected from:
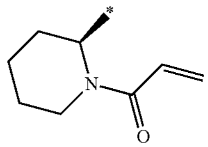,
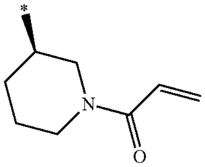,
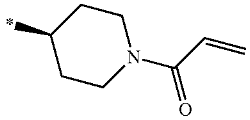,
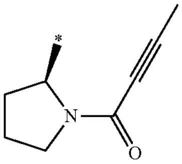
or
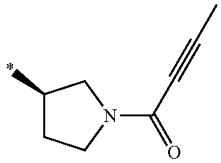
;
—$Ar_1$-$L_a$-$AR_2$ is selected from:
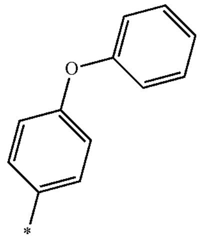
or
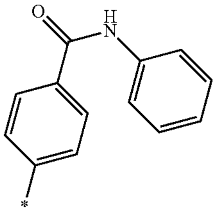
;
Preferably, in the above mentioned embodiment, the compound of formula (I) may be selected from the following compound:
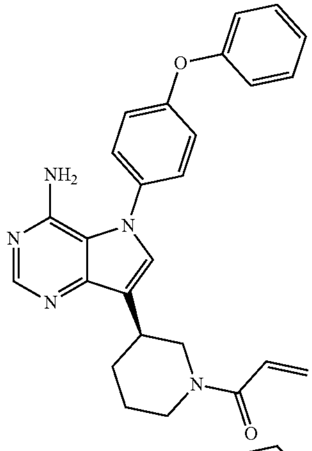,
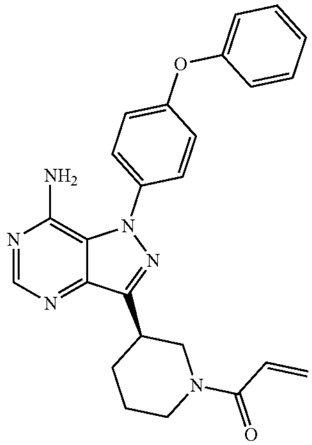
or
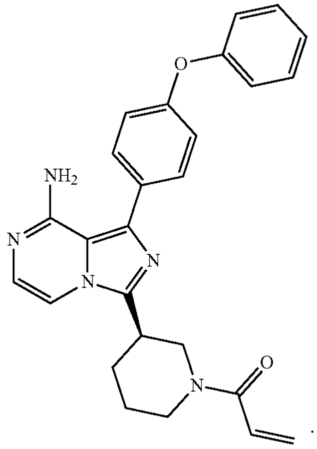.
In another embodiment, the present disclosure relates to a compound of formula (IV),
(IV)
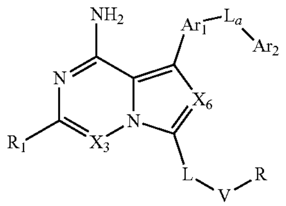

or a pharmaceutically acceptable salt, stereoisomer, or tautomer thereof, wherein:

$Ar_1$ is ring C of the formula:

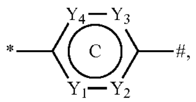

wherein:

$Y_1$ is $CR_2$ or N;

$Y_2$ is $CR_2$ or N;

$Y_3$ is $CR_2$ or N;

$Y_4$ is $CR_2$ or N;

each $R_2$ is independently H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, $—OR_{2a}$, $—N(R_{2a})_2$, $—SR_{2a}$, $—Si(R_{2a})_3$, $—C(=O)R_{2a}$, $—C(=O)OR_{2a}$, $—C(=O)N(R_{2a})_2$, $—NR_{2a}C(=O)R_{2a}$, $—NR_{2a}C(=O)OR_{2a}$, $—NR_{2a}C(=O)N(R_{2a})_2$, $—OC(=O)R_{2a}$, $—OC(=O)OR_{2a}$ or $—OC(=O)N(R_{2a})_2$, wherein each $R_{2a}$ is independently H, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, or two $R_{2a}$ groups together form substituted or unsubstituted $C_3$-$C_7$ heterocyclyl or substituted or unsubstituted $C_5$-$C_{10}$ heteroaryl;

or, $Y_1$, $Y_2$ together with their substituent $R_2$ form substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

* is the point of attachment to the carbon atom of the bicyclic ring; and # is the point of attachment to $L_a$;

$Ar_2$ is substituted or unsubstituted $C_6$-$C_{10}$ aryl or substituted or unsubstituted $C_5$-$C_{10}$ heteroaryl;

L is:

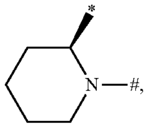

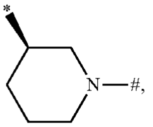

or

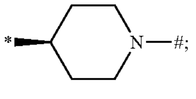

wherein:

* is the point of attachment to the carbon atom of the bicyclic ring; and # is the point of attachment to V;

$L_a$ is a bond, —O—, —S—, $—NR_3—$, $—C(R_3)_2—$, —C(=O)—, —C(=O)O—, —OC(=O)—, $—C(=O)NR_3—$, $—NR_3C(=O)—$, $—NR_3C(=O)NR_3—$, $—OC(=O)NR_3—$, $—NR_3C(=O)O—$, $—S(=O)_m—$, $—S(=O)_mNR_3—$, $—NR_3S(=O)_m—$, $—NR_3S(=O)_mNR_3—$, $—OP(=O)_mR_3—$, $—P(=O)_mOR_3—$, wherein, each $R_3$ is H, OH, halo, CN, $NO_2$, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, or two $R_3$ groups together form substituted or unsubstituted $C_3$-$C_7$ heterocyclyl or substituted or unsubstituted $C_5$-$C_{10}$ heteroaryl, m is 1 or 2;

V is a bond, —C(=O)—, —C(=O)O—, —OC(=O)—, $—C(=O)NR_4—$, $—NR_4C(=O)—$, $—NR_4C(=O)NR_4—$, $—OC(=O)NR_4—$, $—NR_4C(=O)O—$, —S(=O), —, $—S(=O)_nNR_4—$, $—NR_4S(=O)_n—$, $—NR_4S(=O)_nNR_4—$, $—OP(=O)_nR_4—$, $—P(=O)_nOR_4—$, wherein, each $R_4$ is H, OH, halo, CN, $NO_2$, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl, or two $R_4$ groups together form substituted or unsubstituted $C_3$-$C_7$ heterocyclyl or substituted or unsubstituted $C_5$-$C_{10}$ heteroaryl, n is 1 or 2;

$X_3$ is $CR_1$ or N;

$X_6$ is $CR_1$ or N;

R is CN, or $C_2$-$C_6$ alkenyl or $C_2$-$C_6$ alkynyl that are optionally substituted by 0, 1, 2 or 3 $R_5$ substituents, wherein, $R_5$ is selected from H, OH, halo, CN, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl;

each $R_1$ is independently H, OH, halo, CN, $NO_2$, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl, substituted or unsubstituted $C_5$-$C_{10}$ heteroaryl, $—OR_{1a}$, $—N(R_{1a})_2$, $—SR_{1a}$, $—Si(R_{1a})_3$, $—C(=O)R_{1a}$, $—C(=O)OR_{1a}$, $—C(=O)N(R_{1a})_2$, $—NR_{1a}C(=O)R_{1a}$, $—NR_{1a}C(=O)OR_{1a}$, $—NR_{1a}C(=O)N(R_{1a})_2$, $—OC(=O)R_{1a}$, $—OC(=O)OR_{1a}$ or $—OC(=O)N(R_{1a})_2$, wherein each $R_{1a}$ is independently H, substituted or unsubstituted $C_1$-$C_6$ acyl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_7$ carbocyclyl, substituted or unsubstituted $C_3$-$C_7$ heterocyclyl, substituted or unsubstituted $C_6$-$C_{10}$ aryl or substituted or unsubstituted $C_5$-$C_{10}$ heteroaryl, or two $R_{1a}$ groups together form substituted or unsubstituted $C_3$-$C_7$ heterocyclyl or substituted or unsubstituted $C_5$-$C_{10}$ heteroaryl.

Preferably, in the above mentioned embodiment, the compound is of formula (IVa), (IVb), (IVc), or (IVd):

(IVa)

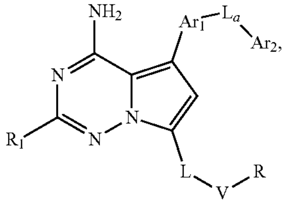

(IVb)

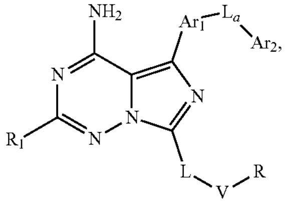

(IVc)

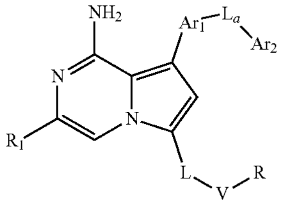

or (IVd)

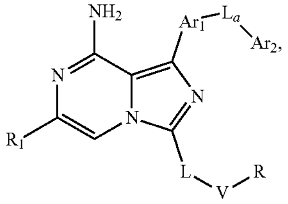

or a pharmaceutically acceptable salt, stereoisomer, or tautomer thereof.

Preferably, in the Above Mentioned Embodiment, Wherein:

$Y_1$ is $CR_2$;

$Y_2$ is $CR_2$;

$Y_3$ is $CR_2$;

$Y_4$ is $CR_2$;

each $R_2$ is H, OH, halo, CN, $NO_2$, substituted or unsubstituted $C_1$-$C_6$ alkyl or substituted or unsubstituted $C_1$-$C_6$ heteroalkyl.

Preferably, in the above mentioned embodiment, $L_a$ is —O—, —S—, —$NR_3$—, —$C(R_3)_2$— or —C(═O)$NR_3$—; wherein, each $R_3$ is independently H, OH, halo, CN or $NO_2$.

Preferably, in the above mentioned embodiment, $Ar_2$ is phenyl or pyridinyl.

Preferably, in the above mentioned embodiment, V is a bond, —C(═O)—, —C(═O)O—, —OC(═O)—, —C(═O)$NR_4$— or —$NR_4$C(═O)—; wherein, each $R_4$ is independently H or substituted or unsubstituted $C_1$-$C_6$ alkyl.

Preferably, in the above mentioned embodiment, R is $C_2$-$C_6$ alkenyl that is optionally substituted by 0 or 1 $R_5$ substituent; $R_5$ is H, CN, substituted or unsubstituted $C_1$-$C_6$ alkyl or substituted or unsubstituted $C_1$-$C_6$ heteroalkyl.

Preferably, in the above mentioned embodiment, R is CH—$CH_2$.

Preferably, in the above mentioned embodiment, -L-V—R is:

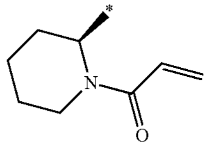

,

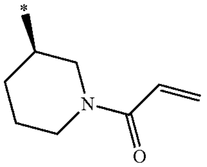

, or

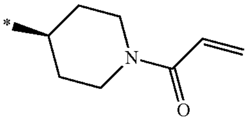

;

—$Ar_1$-$L_a$-$Ar_2$ is:

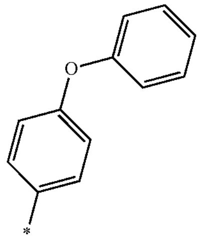

or

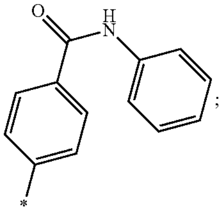

;

$X_3$ is CH or N;

$X_6$ is CH or N.

Preferably, in the above mentioned embodiment, the compound is selected from:

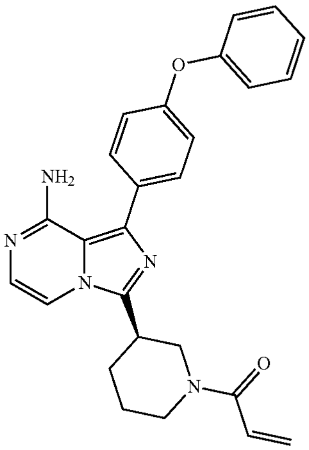

,

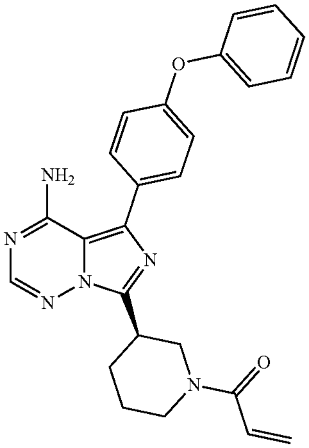

, or

-continued

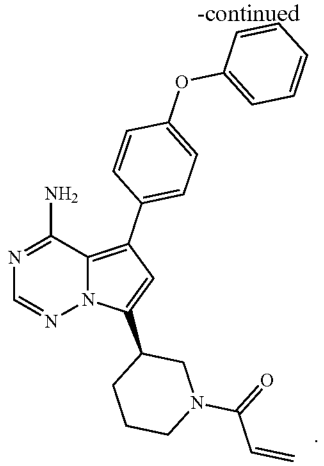

In another embodiment, the present disclosure relates to a pharmaceutical composition, comprising a compound disclosed herein, or a pharmaceutically acceptable salt, stereoisomer, or tautomer thereof, and a pharmaceutically acceptable excipients.

In another embodiment, the present disclosure relates to method of treating or preventing a disease mediated by BTK kinase in a subject, comprising administering to the subject a therapeutically effective amount of a compound disclosed herein, or a pharmaceutically acceptable salt, stereoisomer, or tautomer thereof.

Preferably, in the above mentioned embodiment, the BTK kinase is the C481S mutant form of BTK kinase.

In another embodiment, the present disclosure relates to a method of treating or preventing a disease selected from the following, or reducing the rate of relapse thereof in a subject, comprising administering to the subject a therapeutically effective amount of a compound disclosed herein, or a pharmaceutically acceptable salt, stereoisomer, or tautomer thereof: allergic diseases, autoimmune diseases, inflammatory diseases, or cancers, such as asthma, arthritis, multiple sclerosis, B-cell proliferative disorder, myeloma, hairy cell leukemia, and pancreatic cancer, including osteoarthritis, rheumatoid arthritis, psoriatic arthritis, lupus, relapsing multiple sclerosis (RMS), relapsing-remitting multiple sclerosis (RRMS), progressive multiple sclerosis (PMS), secondary-progressive multiple sclerosis (SPMS), primary-progressive multiple sclerosis (PPMS), progressive-relapsing multiple sclerosis (PRMS), chronic lymphocytic leukemia, Waldenstrom's macroglobulinemia, lymphoma, chronic lymphocytic lymphoma, Hodgkin's lymphoma, non-Hodgkin's lymphoma, diffuse large B-cell lymphoma, mediastinal large B-cell lymphoma, intravascular large B-cell lymphoma, mantle cell lymphoma, follicular lymphoma, small lymphocytic lymphoma, marginal zone lymphoma, splenic marginal zone lymphoma, nodal marginal zone B-cell lymphoma, extranodal marginal zone B-cell lymphoma, burkitt lymphoma, lymphoplasmacytic lymphoma, and primary effusion lymphoma.

Preferably, in the above mentioned embodiment, the disease is selected from the following: multiple sclerosis, relapsing multiple sclerosis, relapsing-remitting multiple sclerosis, progressive multiple sclerosis, secondary-progressive multiple sclerosis, primary-progressive multiple sclerosis, and progressive-relapsing multiple sclerosis.

Preferably, in the above mentioned embodiment, the therapeutically effective amount is a daily amount ranging from about 1 mg to 500 mg, alternatively from 20 mg to 300 mg, alternatively from 20 mg to 200 mg, alternatively from 30 mg to 300 mg, alternatively from 25 mg to 150 mg, alternatively from 50 mg to 100 mg, alternatively from 20 mg to 50 mg, alternatively from 50 mg to 100 mg, alternatively from 100 mg to 150 mg, alternatively from 75 mg to 100 mg, alternatively about 25 mg, alternatively about 50 mg, alternatively about 75 mg, and alternatively about 100 mg.

Preferably, in the above mentioned embodiment, the compound disclosed herein, or a pharmaceutically acceptable salt, stereoisomer, or tautomer thereof is administered once per day, twice per day, or three times per day.

Preferably, in the above mentioned embodiment, the compound disclosed herein, or a pharmaceutically acceptable salt, stereoisomer, or tautomer thereof is administered twice per day, and there is at least 8 hours, 6 hours, 4 hours, or 2 hours between taking two dosages.

Preferably, in the above mentioned embodiment, the compound disclosed herein, or a pharmaceutically acceptable salt, stereoisomer, or tautomer thereof is administered twice per day, and the two dosages are administered in the morning and in the evening, respectively.

Preferably, in the above mentioned embodiment, the compound disclosed herein, or a pharmaceutically acceptable salt, stereoisomer, or tautomer thereof is administered orally.

Preferably, in the above mentioned embodiment, the compound disclosed herein, or a pharmaceutically acceptable salt, stereoisomer, or tautomer thereof is administered for a duration of at least 1 week, alternatively at least 2 weeks, alternatively at least 3 weeks, alternatively at least 1 month, alternatively at least 2 months, alternatively at least 3 months, alternatively at least 6 months, alternatively at least 1 year, alternatively at least 2 years, and alternatively at least 3 years.

Preferably, in the above mentioned embodiment, the compound disclosed herein, or a pharmaceutically acceptable salt, stereoisomer, or tautomer thereof is administered with food, alternatively is administered without taking food, alternatively is administered within 1 hour prior to taking food, alternatively is administered within 2 hours prior to taking food, alternatively is administered within 3 hours prior to taking food, alternatively is administered within 1 hour after taking food, alternatively is administered within 2 hours after taking food, alternatively is administered within 3 hours after taking food.

Preferably, in the above mentioned embodiment, the compound disclosed herein, or a pharmaceutically acceptable salt, stereoisomer, or tautomer thereof is administered in a form of tablets, pills, capsules, semisolids, powders, sustained release formulations, solutions, suspensions, elixirs, aerosols, or any other appropriate compositions.

Preferably, in the above mentioned embodiment, the subject experiences at least a 5% reduction in the number of gadolinium positive Tl magnetic resonance imaging lesions after receiving the compound disclosed herein, or a pharmaceutically acceptable salt, stereoisomer, or tautomer thereof for a duration of 6 weeks, 12 weeks, 18 weeks, 24 weeks, or 48 weeks, for example, alternatively experiences at least a 15% reduction in the number of gadolinium positive Tl magnetic resonance imaging lesions after receiving the compound disclosed herein, or a pharmaceutically acceptable salt, stereoisomer, or tautomer thereof for a duration of 6 weeks, 12 weeks, 18 weeks, 24 weeks, or 48 weeks, for example, alternatively experiences at least a 30% reduction in the number of gadolinium positive Tl magnetic resonance imaging lesions after receiving the compound disclosed herein, or a pharmaceutically acceptable salt, stereoisomer, or tautomer thereof for a duration of 6 weeks, 12 weeks, 18 weeks, 24 weeks, or 48 weeks, for example, and alternatively experiences at least a 50% reduction in the number of gadolinium positive Tl magnetic resonance imaging lesions after receiving the compound of disclosed herein, or a pharmaceutically acceptable salt, stereoisomer, or tautomer thereof for a duration of 6 weeks, 12 weeks, 18 weeks, 24 weeks, or 48 weeks, for example.

Preferably, in the above mentioned embodiment, the subject experiences at least a 5% reduction in the collective size of gadolinium positive Tl magnetic resonance imaging lesions after receiving the compound disclosed herein, or a pharmaceutically acceptable salt, stereoisomer, or tautomer thereof for a duration of 6 weeks, 12 weeks, 18 weeks, 24 weeks, or 48 weeks, for example, alternatively experiences at least a 15% reduction in the collective size of gadolinium positive Tl magnetic resonance imaging lesions after receiving the compound disclosed herein, or a pharmaceutically acceptable salt, stereoisomer, or tautomer thereof for a duration of 6 weeks, 12 weeks, 18 weeks, 24 weeks, or 48 weeks, for example, alternatively experiences at least a 30% reduction in the collective size of gadolinium positive Tl magnetic resonance imaging lesions after receiving the compound disclosed herein, or a pharmaceutically acceptable salt, stereoisomer, or tautomer thereof for a duration of 6 weeks, 12 weeks, 18 weeks, 24 weeks, or 48 weeks, for example, and alternatively experiences at least a 50% reduction in the collective size of gadolinium positive Tl magnetic resonance imaging lesions after receiving the compound disclosed herein, or a pharmaceutically acceptable salt, stereoisomer, or tautomer thereof for a duration of 6 weeks, 12 weeks, 18 weeks, 24 weeks, or 48 weeks, for example.

Preferably, in the above mentioned embodiment, the subject experiences reduction of the number of new or enlarging T2 lesions formation, alternatively the number of new or enlarging T2 lesions is equal to or less than 2.

Preferably, in the above mentioned embodiment, further comprising evaluating disability progression in the subject, wherein disability progression is evaluated using the Expanded Disability Status Scale (EDSS), the 9-Hole Peg Test (9-HPT), or the Timed 25-Foot Walk Test (T25FWT), or any combinations thereof.

Preferably, in the above mentioned embodiment, further comprising evaluating the onset of composite 12-week confirmed disability progression (cCDP12), wherein onset of the cCDP12 comprises at least one progression event selected from the group consisting of:

(a) an increase from baseline in EDSS score of at least 1.0 point in a subject with a baseline EDSS score of less than or equal to 5.5 points; or an increase from baseline in EDSS score of at least 0.5 point in a subject with a baseline EDSS score of greater than 5.5 points;

(b) increase from baseline of at least 20% in time to complete the 9-HPT; and (c) increase from baseline of at least 20% in T25FWT.

and wherein the progression event is confirmed at least 12 weeks after the initial progression.

Preferably, in the above mentioned embodiment, time to a progression event in the subject is increased, wherein the progression event is increase of at least 20% from baseline in time to complete the 9-HPT.

Preferably, in the above mentioned embodiment, time to a progression event in the subject is increased, wherein the progression event is an increase of at least 20% from baseline in T25FWT.

Preferably, in the above mentioned embodiment, time to onset of 12-week confirmed disability progression (CDP12), cCDP12, 24-week confirmed disability progression (CDP24), or composite 24-week confirmed disability progression (cCDP24) is increased in comparison to a subject with PPMS who is not administered the compound disclosed herein, or a pharmaceutically acceptable salt, stereoisomer, or tautomer thereof.

Preferably, in the above mentioned embodiment, the subject with PPMS who is not administered an anti-CD20 antibody.

Preferably, in the above mentioned embodiment, the time to a progression event or time to onset is increased at least 5%, at least 10%, at least 15%, at least 20%, at least 25%, at least 30%, or at least 35%.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer (such as cis- and trans-isomer), or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses.

Also disclosed herein are all suitable isotopical variants of the compounds disclosed herein. An isotope derivative of a compound disclosed herein is defined as wherein at least one atom is replaced by an atom having the same atomic number but differing in atomic mass from the atomic mass typically found in nature. Examples of isotopes that can be incorporated into compounds disclosed herein include hydrogen, carbon, nitrogen, oxygen, fluorine, phosphorus, sulfur, and chlorine isotopes, such as $^{2}H$, $^{3}H$, $^{13}C$, $^{14}C$, $^{15}N$, $^{17}O$, $^{18}O$, $^{18}F$, $^{31}P$, $^{32}P$, $^{35}S$ and $^{36}Cl$, respectively. Certain isotopical variants of the compounds disclosed herein, such as the radioisotopes of $^{3}H$ and $^{14}C$ are incorporated are useful in the tissue distribution experiments of drugs and substrates. Tritium, i.e., $^{3}H$, and carbon-14, i.e., $^{14}C$, are particularly preferred for their case of preparation and detectability. In addition, substitution with heavier isotopes such as deuterium, i.e., $^{2}H$, has therapeutic advantages due to its good metabolic stability, for example, increased half-life in vivo or reduced dosage, and is thus preferable in some cases. Isotopical variants of the compounds disclosed herein can be prepared conventionally by the following procedures, for example by descriptive methods or by the preparations described in the Examples below, using appropriate reagents containing appropriate isotopes.

After study and research, the present inventors have unexpectedly discovered that the deuterated compound of the fused bicyclic compound disclosed herein and its pharmaceutically acceptable salt have equivalent or superior pharmacokinetics and/or pharmacodynamics properties, as compared with the non-deuterated compound of the fused bicyclic compound disclosed herein. It is thus suitable for use as a compound to inhibit BTK kinase and is more suitable for the preparation of a medicament for treating cancer and BTK kinase-related diseases.

The compound of the present disclosure or a pharmaceutically acceptable salt thereof may be in an amorphous or crystalline form. Furthermore, the compounds of the present disclosure may exist in one or more crystalline forms.

Accordingly, the disclosure includes within its scope all amorphous or crystalline forms of the compounds disclosed herein.

Those skilled in the art will appreciate that many organic compounds can form complexes with solvents that react in or precipitate or crystallize from the solvent. These complexes are referred to as "solvates." When the solvent is water, the complex is referred to as a "hydrate." The disclosure encompasses all solvates of the compounds disclosed herein.

In addition, prodrugs are also included within the context of the present disclosure. The term "prodrug" as used herein refers to a compound which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each is incorporated herein by reference.

A prodrug is any covalently bonded carrier which, when administered to a patient, releases the compound disclosed herein in vivo. Prodrugs are typically prepared by modifying functional groups in such a way that the modifications of the prodrug can be cleaved in vivo to yield the parent compound. Prodrugs include, for example, compounds disclosed herein wherein a hydroxy, amino or sulfhydryl group is bonded to any group which, when administered to a patient, can be cleaved to form a hydroxy, amino or sulfhydryl group. Thus, representative examples of prodrugs include, but are not limited to, covalent derivative formed by hydroxyl, amino or mercapto functional groups of the compounds disclosed herein reacted with acetic acid, formic acid or benzoic acid. Further, in the case of a carboxylic acid (—COOH), an ester such as a methyl ester, an ethyl ester or the like can be used. The ester itself may be active and/or may hydrolyze under conditions in human bodies. Suitable pharmaceutically acceptable hydrolysable in vivo ester groups include those groups which readily decompose in the human body to release the parent acid or a salt thereof.

Pharmaceutical Compositions, Formulations and Kits

In another aspect, the disclosure provides a pharmaceutical composition comprising a compound of the present disclosure (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that can be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (eg, vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The following formulation examples illustrate representative pharmaceutical compositions that may be prepared in accordance with this disclosure. The present disclosure, however, is not limited to the following pharmaceutical compositions.

Exemplary Formulation 1—Tablets: A compound of the present disclosure may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 2—Tablets: A compound of the present disclosure may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 3—Tablets: A compound of the present disclosure may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 4—Tablets: A compound of the present disclosure may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 5—Tablets: A compound of the present disclosure may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 6—Tablets: A compound of the present disclosure may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Exemplary Formulation 7—Tablets: A compound of the present disclosure may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 8—Capsules: A compound of the present disclosure may be admixed as a dry powder with a starch diluent in an approximate 1:1 weight ratio. The mixture is filled into 250 mg capsules (125 mg of active compound per capsule).

Exemplary Formulation 9—Liquid: A compound of the present disclosure (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 10—Injection: A compound of the present disclosure may be dissolved or suspended in a buffered sterile saline injectable aqueous medium to a concentration of approximately 5 mg/mL.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present disclosure may be further delivered using a variety of dosing methods. For example, in certain embodiments, the pharmaceutical composition may be given as a bolus, e.g., in order to rapidly raise the concentration of the compound in the blood to an effective level. The bolus dose depends on the systemic levels of the active ingredient desired, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient (s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional dermal penetration ingredients to enhance the stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present disclosure can also be administered in sustained release forms or from sustained release drug delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Treatment

The compounds disclosed herein and pharmaceutical compositions thereof can be used to treat or prevent a variety of conditions or diseases mediated by Bruton's Tyrosine kinase (BTK). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombogenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenia purpura, rheumatoid arthritis, Sjogren's syndrome, Eiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders, kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular pemphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemia, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenia purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The present disclosure thus provides the use of the compound of formula (I) or a pharmaceutically acceptable salt, a stereoisomer, a solvate, a hydrate, a polymorph, a prodrug or an isotopic variants thereof in therapeutics, especially in the treatment of diseases and disorders mediated by inappropriate BTK activity.

The inappropriate BTK activity referred to herein is any BTK activity that deviates from the normal BTK activity expected in a particular mammalian subject. Inappropriate BTK activity may take the form of, for instance, an abnormal increase in activity, or an aberration in the timing and or control of BTK activity. Such inappropriate activity may result then, for example, from overexpression or mutation of the protein kinase leading to inappropriate or uncontrolled activation.

In a further embodiment, the present disclosure is directed to methods of regulating, modulating, or inhibiting BTK for the prevention and/or treatment of disorders related to unregulated or inappropriate BTK activity.

In a further embodiment said disorder mediated by BTK activity is asthma. In a further embodiment said disorder is rheumatoid arthritis. In yet another embodiment, said disorder is cancer. In a further embodiment said disorder is ocular conjunctivitis.

In another embodiment, the present disclosure provides the use of the compound of formula (I) or a pharmaceutically acceptable salt, a stereoisomer, a solvate, a hydrate, a polymorph, a prodrug or an isotopic variants thereof in the manufacture of a medicament for treating diseases mediated by BTK activity.

A further aspect of the disclosure resides in the use of a compound of formula (I) or a pharmaceutically acceptable salt, a stereoisomer, a solvate, a hydrate, a polymorph, a prodrug or an isotopic variants thereof for the manufacture of a medicament to be used for the treatment of BTK-mediated diseases.

A further aspect of the disclosure resides in the use of a compound of formula (I) or a pharmaceutically acceptable salt, a stereoisomer, a solvate, a hydrate, a polymorph, a prodrug or an isotopic variants thereof for the manufacture of a medicament to be used for the treatment of chronic B cell disorders in which T cells play a prominent role.

In yet another aspect the disclosure resides in the use of a compound of formula (I) or a pharmaceutically acceptable salt, a stereoisomer, a solvate, a hydrate, a polymorph, a prodrug or an isotopic variants thereof for the manufacture of a medicament to be used for the treatment of BTK-mediated diseases. These BTK-mediated diseases include, but are not limited to, B cell lymphomas resulting from chronic active B cell receptor signaling.

Thus, the compounds disclosed herein may be used to treat or prevent diseases such as Bruton's Tyrosine Kinase (BTK) mediated diseases. BTK mediated diseases as used herein, mean any disease state or other deleterious condition in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds disclosed herein include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g. hemolytic anemia, aplastic anemia, idiopathic thrombocytopenia, chronic idiopathic thrombocytopenic purpura (ITP), and neutropenia), autoimmune gastritis, and autoimmune inflammatory bowel diseases (e.g. ulcerative colitis and Crohn's disease), irritable bowel syndrome, host versus graft disease, allograft rejection, chronic thyroiditis, Graves' disease, Sjorgren's disease, scleroderma, diabetes (type I and type II), active hepatitis (acute and chronic), pancreatitis, primary biliary cirrhosis, myasthenia gravis, multiple sclerosis, systemic lupus erythematosis, psoriasis, atopic dermatitis, dermatomyositis, contact dermatitis, eczema, skin sunburns, vasculitis (e.g. Behcet's disease), ANCA-associated and other vasculitides, chronic renal insufficiency, Stevens-Johnson syndrome, inflammatory pain, idiopathic sprue, cachexia, sarcoidosis, Guillain-Barre syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that may be treated or prevented include, among others, allergies to foods, food additives, insect poisons, dust mites, pollen, animal materials and contact allergens, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of formula (I) or pharmaceutically acceptable salts may be used for the treatment of B cell lymphomas resulting from chronic active B cell receptor signaling.

Included herein are methods of treatment and/or pharmaceutical compositions in which at least one compound of formula (I) or a pharmaceutically acceptable salt thereof is administered in combination with at least one other active agent. The other active agent is an anti-inflammatory agent, an immunosuppressant agent, or a chemotherapeutic agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The disclosure also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the disclosure pertain to combinations in which at least one anti-inflammatory agent is an anti-C5 monoclonal antibody (such as eculizumab or pexelizumab), a TNF antagonist, such as etanercept, or infliximab, which is an anti-TNF alpha monoclonal antibody.

Still other embodiments of the disclosure pertain to combinations in which at least one active agent is an immunosuppressant agent, such as an immunosuppressant compound chosen from methotrexate, leflunomide, cyclosporine, tacrolimus, azathioprine, and mycophenolate mofetil.

It has also been discovered that BTK inhibitors are useful as chemosensitizing agents, and, thus, are useful in combination with other chemotherapeutic agents, in particular, drugs that induce apoptosis. Examples of other chemotherapeutic agents that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g., antibodies such as anti CD20 antibody, IDEC 8, immunotoxins, and cytokines).

In another embodiment, the present disclosure provides a method of treating a mammal having a disease mediated by BTK activity, the method comprising: administering to the mammal an effective amount of a compound of formula (I) or a pharmaceutically acceptable salt, a solvate or a physiologically functional derivative thereof.

An effective amount of a compound disclosed herein will generally be administered in a single or multiple doses at an average daily dose of from 0.01 mg to 50 mg of compound per kilogram of patient body weight, preferably from 0.1 mg to 25 mg of compound per kilogram of patient body weight. In general, the compounds disclosed herein may be administered to a patient in need of such treatment in a daily dosage range of from about 1 mg to about 3500 mg per patient, preferably from 10 mg to 1000 mg. For example, the daily dose per patient can be 10, 20, 30, 40, 50, 60, 70, 80, 90, 100, 150, 200, 250, 300, 350, 400, 500, 600, 700, 800, 900 or 1000 mg. It can be administered one or more times daily, weekly (or several days apart) or on an intermittent schedule. For example, the compound can be administered one or more times per day on a weekly basis (e.g., every Monday), continually or for several weeks, such as 4-10 weeks. Alternatively, the administration may be continued for several days (e.g., 2-10 days), followed by a few days (e.g., 1-30 days) without administration of the compound, and the cycle may be repeated indefinitely or repeated for a given number of times, such as 4-10. Cycles. For example, the compounds disclosed herein may be administered daily for 5 days, then intermittently for 9 days, then administered daily for 5 days, then intermittent for 9 days, and so on, and the cycle is repeated indefinitely or repeated 4-10 times.

Combination in Therapy

Compounds disclosed herein, and their salts and solvates, and physiologically functional derivatives thereof, may be employed alone or in combination with other therapeutic agents for the treatment of BTK mediated diseases and conditions associated with inappropriate BTK activity. Combination therapies according to the present disclosure thus comprise the administration of at least one compound of formula (I) or a pharmaceutically acceptable salt or solvate thereof, or a physiologically functional derivative thereof, and the use of at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of formula (I) may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) nonselective COX-1/COX-2 inhibitors (such as piroxicam, diclofenac, propionic acids such as naproxen, flurbiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic HI receptor antagonists such as cetirizine, levocetirizine, loratadine, desloratadine, fexofenadine, astemizole, azelastine, levocabastine, olopatadine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK1 and/or JAK2 and or JAK3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present disclosure also provides for "triple combination" therapy, comprising a compound of formula (I) or a pharmaceutically acceptable salt thereof together with beta2-adrenoreceptor agonist and an anti-inflammatory corticosteroid. Preferably this combination is for treatment and/or prophylaxis of asthma, COPD or allergic rhinitis.

For the treatment of cancer a compound of formula (I) may be combined with one or more of an anticancer agents. Examples of such agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstilbestrol, tamoxifen, raloxifene, idoxifene, LY353381, LY117081, toremifene, fluoxymesterone, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fortamine sodium hydrate, raltitrexed, raltitrexed, emitefur, tiazofurin, decitabine, nolatrexed, pemetrexed, nelarabine, 2'-deoxy-2'-methylidenecytidine, 2'-fluoromethylene-2'-deoxycytidine, N6-[4-deoxy-4-[N2-[2(E),4(E)-tetradeca-dienoyl]glycylamino]-L-glycero-B-L-manno-hepto pyranosyl]adenine, aplidine, ecteinascidin, troxacitabine, aminopterin, 5-flurouracil, floxuridine, methotrexate, leucovorin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridin-2-carboxaldehyde thiosemicarbazone; (6) prenyl-protein transferase inhibitor including farnesyl-protein transferase (FPTasc), geranylgeranyl-protein transferase type I (GGPTase-I), and geranylgeranyl-protein transferase type-II (GGPTase-II, also called Rab GGPTase); (7) HMG-COA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoetin-α), granulocyte-CSF (filgrastim), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, Ukraine, ranpirnase, IM862, acetyldinaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannotetraose phosphate, and 3-[(2,4-dimethylpyrrol-5-yl) methylene]-2-indolinone (SU5416); (9) PPAR-Y agonists, PPAR-8 agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy) phenoxy)propoxy)-2-ethylchromone-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib, erlotinib, icotinib and Osimertinib (AZD9291)), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and CDK and CDC kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, porfiromycin, cisplatin, irofulven, dexifosfamide, cis-aminedichloro(2-methyl-pyridine) platinum, benzyl guanine, glufosfamide, GPX100, (trans, trans, trans)-bis-mu-(hexane-1,6-diamine)-mu-[diamine-platinum (II)]bis[diamine (chloro) platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicamycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS 188797.

Some examples of topoisomerase inhibitors are topotecan, hycamptamine, irinotecan, rubitecan, 6-ethoxypropionyl-3',4'-O-exo-benzylidene-chartreusin, lurtotecan, 7-[2-(N-isopropylamino)ethyl]-(20S) camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]-formamide, N-(2-(dimethylamino)ethyl) acridine-4-carboxamide, 6-[[2-(dimethylamino)ethyl]amino]-3-hydroxy-7H-indeno[2,1-c] quinolin-7-one, and dimesna.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosylidene, aplidine, ecteinascidin, troxacitabine, aminopterin, 5-flurouracil, floxuridine, methotrexate, leucovorin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of formula (I) include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; Tarceva; Orsiro; gemcitabine; gemtuzumab ozogamicin; goserelin acetate; histrelin acetate; hydroxyurea; ibritumomab tiuxetan; idarubicin; ifosfamide; imatinib mesylate; interferon α-2a; interferon α-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronate; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be apparent to those skilled in the art that, where appropriate, the other therapeutic component or ingredients may be used in the form of a salt (e.g., an alkali metal salt or amine salt or an acid addition salt), or a prodrug, or an ester (e.g., an ester of lower alkyl group), or solvates (e.g., hydrates), to optimize the activity and/or stability and/or physical properties (e.g., solubility) of the therapeutic component. It is also clear that the therapeutic ingredients can be used in optically pure form, where appropriate.

The above combination may conveniently be used in the form of a pharmaceutical composition, and thus a pharmaceutical composition comprising the above combination and a pharmaceutically acceptable diluent or carrier represents a further aspect of the present disclosure. These combinations are particularly useful for respiratory diseases and are suitable for inhalation or intranasal delivery.

The individual compound in the combination may be administered sequentially or simultaneously in separate or combined pharmaceutical compositions. Preferably, each compound is administered simultaneously in the form of a combined pharmaceutical composition. Suitable dosages of known therapeutic agents are readily apparent to those skilled in the art.

EXAMPLES

The following examples are provided to provide those skilled in the art with a complete disclosure and description of how to carry out the methods, and prepare and evaluate the compounds disclosed herein, which are only for illustrative purpose and not constitute any limitation of the scope of the invention.

Synthetic Method

The compounds of the present disclosure can be prepared according to conventional methods in the art and using suitable reagents, starting materials, and purification methods known to those skilled in the art.

The preparation of the compounds of the present disclosure is more specifically described below, but these specific methods do not constitute any limitation to the present disclosure. The compounds of the present disclosure may also be conveniently prepared by combining various synthetic methods described in the specification or known in the art, and such combinations are readily available to those skilled in the art to which the present disclosure pertains.

Usually, in the preparation, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Example 1 Preparation of 1-(3-(4-amino-5-(4-phenoxyphenyl)-5H-pyrrolo[3,2-d]pyrimidin-7-yl)piperidin-1-yl)prop-2-en-1-one (compound 14)

14

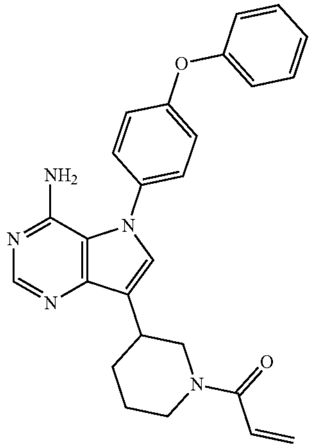

The specific synthetic steps are as follows:

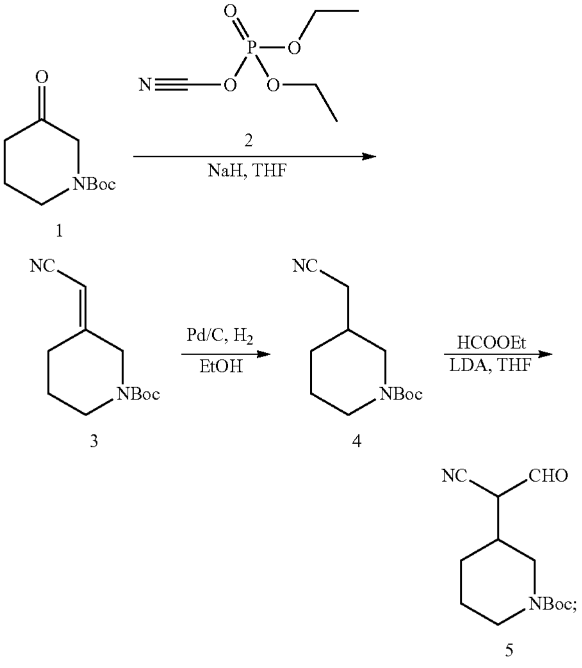

-continued

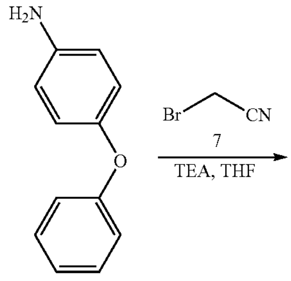

6

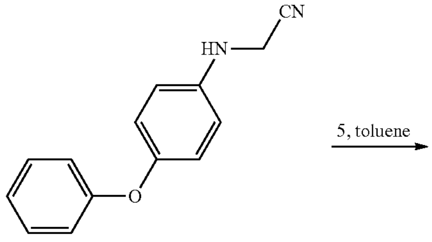

8

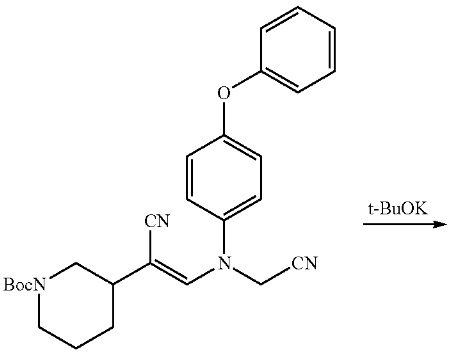

9

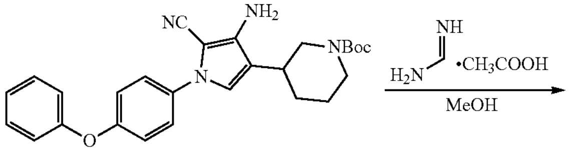

10

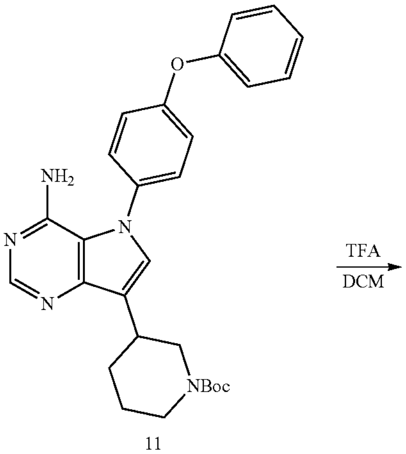

11

-continued

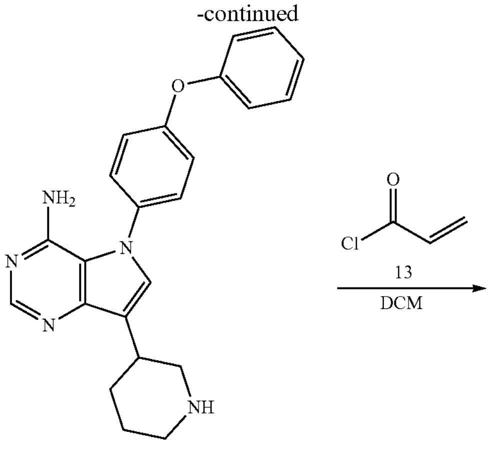

12

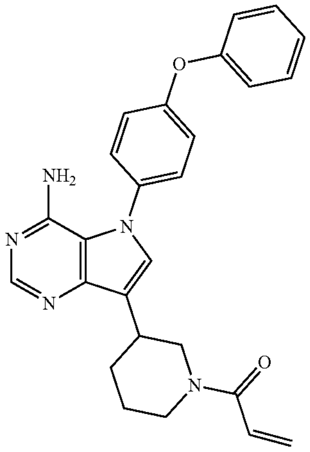

14

Step 1. Synthesis of (E)-tert-butyl 3-(cyanomethylene)piperidin-1-carboxylate (Compound 3)

Under nitrogen protection, sodium hydride (NaH, 0.19 g, 7.8 mmol) was added to 10 mL tetrahydrofuran, which was cooled to 0° C. with an ice bath, diethyl (cyanomethyl) phosphonate (compound 2, 1.38 g, 7.8 mmol) was added dropwise, and stirred for 10 minutes after the complete of addition. Then N-tert-butoxycarbonyl-3-piperidinone (compound 1, 1.7 g, 8.5 mmol) in 10 mL tetrahydrofuran (THF) was added dropwise to the solution, ice bath was removed after the complete of addition, and the reaction was reacted at room temperature overnight. To the reaction mixture were added 30 mL water and 30 mL ethyl acetate, stirred for 5 minutes, and the layers were separated after standing. The organic layer was washed with 10 mL brine, dried over anhydrous sodium sulfate, concentrated, and purified by column chromatography to afford 1.4 g of a light yellow oil, yield was 74%. LC-MS(APCI): m/z=223(M+1)$^+$.

Step 2. Synthesis of tert-butyl 3-(cyanomethyl)piperidin-1-carboxylate (Compound 4)

(E)-tert-butyl 3-(cyanomethylene)piperidin-1-carboxylate (1.4 g, 6.3 mmol) was dissolved in 20 mL anhydrous ethanol, to which 150 mg 10% Pd/C was added, the atmosphere was replaced with hydrogen gas for three times, the mixture was stirred under 1 atmospheric pressure of hydrogen gas at 50° C. overnight. Pd/C was filtered off after the reaction was complete, the filtrate was concentrated, and separated by silica gel column to afford 1.2 g of a light yellow oil, yield was 85%. LC-MS(APCI): m/z=225(M+1)$^+$.

Step 3. Synthesis of tert-butyl 3-(1-cyano-2-oxoethyl)piperidin-1-carboxylate (Compound 5)

Tert-butyl 3-(cyanomethyl)piperidin-1-carboxylate (1.2 g, 5.4 mmol) was dissolved in 10 mL tetrahydrofuran, which was cooled to −78° C., a solution of lithium diisopropylamide (LDA, 0.3 mg, 2.7 mmol) in tetrahydrofuran (2 M, 2.7 mL) was slowly added dropwise, and stirred for 10 minutes after the complete of addition. Then a pre-colded solution of ethyl formate (0.42 g, 5.6 mmol) in 10 mL tetrahydrofuran was added dropwise. After the addition was over, the reaction was reacted at −78° C. for 0.5 hour, then ice bath was removed, and the reaction was warmed to room temperature naturally and reacted overnight. The reaction mixture was adjusted with 1N hydrochloric acid to pH=3, then extracted with ethyl acetate, and the organic phase was washed with 15 mL brine, dried over anhydrous sodium sulfate, concentrated, and purified by column chromatography to afford 0.9 g of a light yellow oil, yield was 66.6%. LC-MS(APCI): m/z=253(M+1)$^+$.

Step 4. Synthesis of 2-((4-phenoxyphenyl)amino)acetonitrile (Compound 8)

4-phenoxyaniline (compound 6, 1.85 g, 10 mmol), bromoacetonitrile (compound 7, 1.56 g, 13 mmol) and triethylamine (TEA, 3 mL, 22 mmol) were dissolved in 50 mL tetrahydrofuran, which was reacted at 80° C. overnight. The temperature was cooled to room temperature after the reaction was complete, concentrated to dry under reduced pressure, 20 mL saturated solution of ammonium chloride and 30 mL ethyl acetate were added, the layers were separated while stirring, the organic phase was washed with 10 mL brine, dried over anhydrous sodium sulfate, concentrated, and purified by column chromatography to afford 1.9 g of a light yellow solid, yield was 85%. LC-MS(APCI): m/z=225 (M+1)$^+$; $^1$H NMR (500 MHz, DMSO-$d_6$) δ 10.36 (s, 1H), 8.36 (ddd, J=4.9, 2.0, 0.9 Hz, 1H), 8.17 (dt, J=8.4, 1.1 Hz, 1H), 7.95 (d, J=8.8 Hz, 2H), 7.80 (ddd, J=8.7, 7.4, 2.0 Hz, 1H), 7.12 (ddd, J=7.3, 4.8, 1.1 Hz, 1H), 6.87 (t, J=6.6 Hz, 1H), 6.78 (d, J=8.8 Hz, 2H), 4.37 (d, J=6.6 Hz, 2H).

Step 5. Synthesis of (Z)-tert-butyl 3-(1-cyano-2-((cyanomethyl)(4-phenoxyphenyl)amino)vinyl)piperidin-1-carboxylate (Compound 9)

2-((4-phenoxyphenyl)amino)acetonitrile (compound 8, 0.67 g, 3 mmol), tert-butyl 3-(1-cyano-2-oxoethyl)piperidin-1-carboxylate (compound 5, 0.9 g, 3.6 mmol) and p-toluene sulfonic acid (57 mg, 0.3 mmol) were dissolved in 20 mLtoluene. Water separator was set, and the reaction was refluxed overnight. The temperature was cooled to room temperature after the reaction was complete, concentrated to dry under reduced pressure, 10 mL saturated solution of sodium bicarbonate was added, stirred for 5 minutes, extracted with ethyl acetate, the organic phase was washed with 15 mL brine, dried over anhydrous sodium sulfate, concentrated, and purified by column chromatography to afford light yellow solid 0.96 g, yield was 70%. LC-MS (APCI): m/z=459(M+1)$^+$.

Step 6. Synthesis of tert-butyl 3-(4-amino-5-cyano-1-(4-phenoxyphenyl)-1H-pyrrol-3-yl)piperidin-1-carboxylate (Compound 10)

(Z)-tert-butyl 3-(1-cyano-2-((cyanomethyl)(4-phenoxyphenyl)amino)vinyl)piperidin-1-carboxylate (compound 9, 0.96 g, 2.1 mmol) was dissolved in 10 mL tert-butyl alcohol, potassium tert-butoxide (t-BuOK, 0.55 g, 4.9 mmol) was added in portions under stirring, and the reaction was reacted at 80° C. for 2 hours after the addition was complete. The reaction mixture was cooled to room temperature, poured into 20 mL 10% hydrochloric acid, stirred for 5 minutes, extracted with ethyl acetate, the organic phase was washed with 15 mL brine, dried over anhydrous sodium sulfate, concentrated, and purified by column chromatography to afford 0.63 g of a red-brown solid, yield was 63%. LC-MS (APCI): m/z=459(M+1)$^+$.

Step 7. Synthesis of Tert-butyl 3-(4-amino-5-(4-phenoxyphenyl)-5H-pyrrolo[3,2-d]pyrimidin-7-yl)piperidin-1-carboxylate (Compound 11)

Tert-butyl 3-(4-amino-5-cyano-1-(4-phenoxyphenyl)-1H-pyrrol-3-yl)piperidin-1-carboxylate (0.31 g, 0.7 mmol) was dissolved in 10 mL methanol, and formamidine acetate (0.55 g, 5.5 mmol) was added, and the reaction was refluxed overnight. The reaction mixture was cooled to room temperature, concentrated to dry under reduced pressure, 20 mL saturated solution of sodium bicarbonate was added, stirred for 5 minutes, extracted with ethyl acetate, the organic phase was washed with 15 mL brine, dried over anhydrous sodium sulfate, concentrated, and purified by column chromatography to afford 0.26 g of a light yellow solid, yield was 80%. LC-MS(APCI): m/z=486(M+1)$^+$.

Step 8. Synthesis of 5-(4-phenoxyphenyl)-7-(piperidin-3-yl)-5H-pyrrolo[3,2-d]pyrimidin-4-amine (Compound 12)

Tert-butyl 3-(4-amino-5-(4-phenoxyphenyl)-5H-pyrrolo[3,2-d]pyrimidin-7-yl)piperidin-1-carboxylate (0.26 g, 0.57 mmol) was dissolved in 10 mL dichloromethane, 4 mL trifluoroacetic acid was added, and stirred at room temperature for 1 hour. After being concentrated to dry under reduced pressure, 20 mL dichloromethane and 15 mL saturated solution of sodium bicarbonate were added, stirred for 5 minutes, the layers were separated, the organic phase was washed with 5 mL brine, dried over anhydrous sodium sulfate, concentrated, and purified by column chromatography to afford 186 mg of a white solid, yield was 90%. LC-MS(APCI): m/z=386(M+1)$^+$.

Step 9. Synthesis of 1-(3-(4-amino-5-(4-phenoxyphenyl)-5H-pyrrolo[3,2-d]pyrimidin-7-yl)piperidin-1-yl)prop-2-en-1-one (Compound 14)

5-(4-phenoxyphenyl)-7-(piperidin-3-yl)-5H-pyrrolo[3,2-d]pyrimidin-4-amine (180 mg, 0.47 mmol) was dissolved in 10 mL dichloromethane, which was cooled to −15° C., acryloyl chloride (compound 13, 42 mg, 0.47 mmol) was slowly added dropwise, and after the addition was complete, the reaction was stirred for 10 minutes. Ice bath was removed, then reacted for 1 hour. To the reaction mixture were added 10 mL water and 10 mL dichloromethane, the layers were separated while stirring, the organic phase was washed with 5 mL brine, dried over anhydrous sodium sulfate, concentrated, and purified by column chromatography to afford 140 mg of a white solid, yield was 70%. LC-MS(APCI): m/z=440(M+1)$^+$; $^1$H NMR (400 MHz, DMSO-$d_6$) δ 8.22 (d, J=6.9 Hz, 1H), 7.52 (s, 1H), 7.48-7.39 (m, 4H), 7.21 (d, J=7.4 Hz, 1H), 7.18-7.10 (m, 4H), 6.92-6.76 (m, 1H), 6.10 (dd, J=16.7, 2.4 Hz, 1H), 5.88 (s, 2H), 5.66 (d, J=10.5 Hz, 1H), 4.43-4.31 (m, 1H), 3.11 (t, J=12.3 Hz, 0.5H), 2.95 (t, J=11.2 Hz, 1H), 2.76 (t, J=12.3 Hz, 0.5H), 2.17-2.07 (m, 1H), 2.04-1.94 (m, 2H), 1.78 (d, J=13.5 Hz, 1H), 1.56-1.41 (m, 2H).
Example 2 Preparation of 1-(3-(7-amino-1-(4-phenoxyphenyl)-1H-pyrazolo[4,3-d]pyrimidin-3-yl)piperidin-1-yl)prop-2-en-1-one (Compound 23)
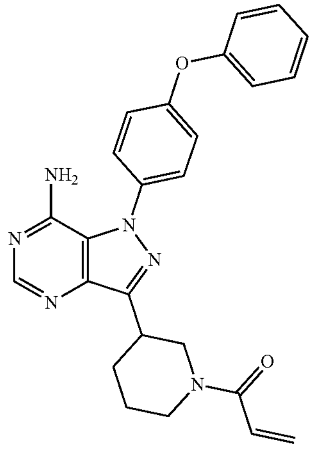
23
The specific synthetic steps are as follows:
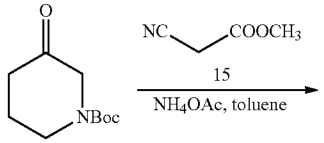
1
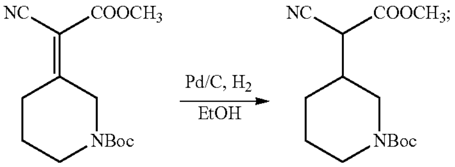
16
17
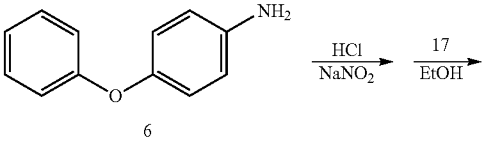
6
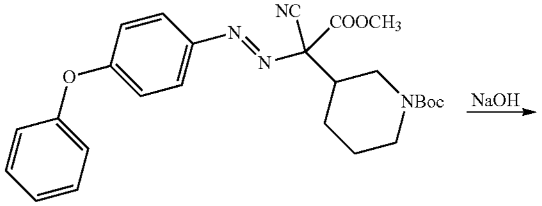
18
-continued
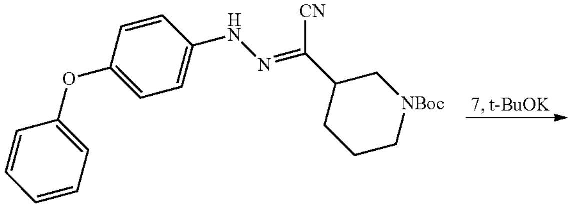
19
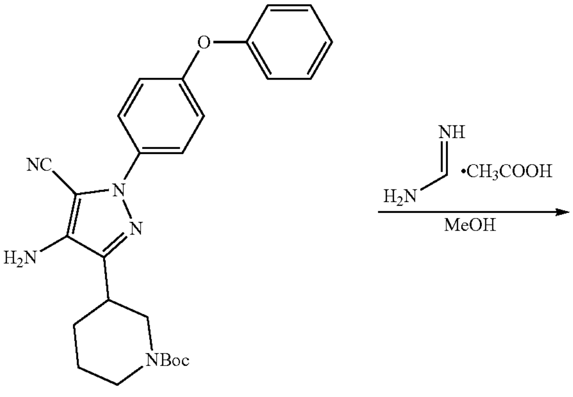
20
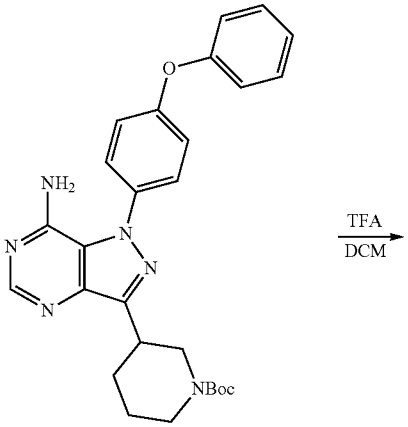
21
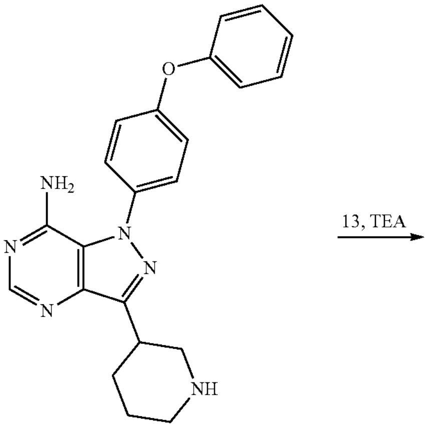
22

-continued

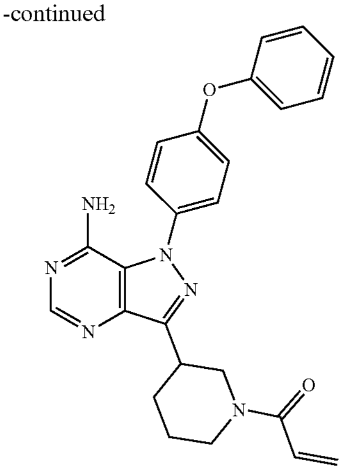

23

Step 1. Synthesis of (Z)-tert-butyl 3-(1-cyano-2-methoxy-2-oxoethylene)piperidin-1-carboxylate (Compound 16)

N-tert-butoxycarbonyl-3-piperidinone (1.99 g, 10 mmol), cyanoethyl acetate (0.99 g, 1 mmol) and ammonium acetate (100 mg, 1.3 mmol) were added to 10 mL toluene, 0.2 mL acetic acid was added dropwise, water separator was set, and the reaction was refluxed overnight. The temperature was cooled to room temperature after the reaction was complete, the reaction was concentrated to dry under reduced pressure, 20 mL water and 20 mL ethyl acetate were added, the layers were separated while stirring, the organic phase was washed with 10 mL brine, dried over anhydrous sodium sulfate, concentrated, and purified by column chromatography to afford 2.2 g of a light yellow oil, yield was 80%. LC-MS (APCI): m/z=281$(M+1)^+$.

Step 2. Synthesis of tert-butyl 3-(1-cyano-2-methoxy-2-oxoethyl)piperidin-1-carboxylate (Compound 17)

(Z)-tert-butyl 3-(1-cyano-2-methoxy-2-oxoethylene)piperidin-1-carboxylate (2.2 g, 7.8 mmol) was dissolved in 20 mL anhydrous ethanol, 200 mg 10% Pd/C was added, the atmosphere was replaced with hydrogen gas for three times, and the mixture was stirred under 1 atmospheric pressure of hydrogen gas at 50° C. overnight. Pd/C was filtered off after the reaction was complete, filtrate was concentrated, and separated by silica gel column to afford 1.34 g of a light yellow oil, yield was 61%. LC-MS(APCI): m/z=283$(M+1)^+$.

Step 3. Synthesis of (E)-tert-butyl 3-(1-cyano-2-methoxy-2-oxo-1-((4-phenoxyphenyl)diazenyl)ethyl)piperidin-1-carboxylate (Compound 18)

4-methoxyaniline (1.57 g, 8.5 mmol) was dissolved in 20 mL 1N hydrochloric acid, 1 M aqueous solution of sodium nitrite (0.58 g, 8.5 mmol) was added dropwise at room temperature, the reaction mixture was stirred at room temperature for 1 hour after the addition was complete. Under an ice bath, the above reaction mixture was slowly added to tert-butyl 3-(1-cyano-2-methoxy-2-oxoethyl)piperidin-1-carboxylate (1.2 g, 4.2 mmol) in ethanol (6 mL)-water (80 mL), adjusted with sodium acetate to pH=7, and the reaction mixture was stirred at 0° C. for 3 hours, then warmed to room temperature and the mixture was stirred overnight. To the reaction mixture was added 30 mL saturated solution of ammonium chloride and 50 mL ethyl acetate, the layers were separated while stirring, the organic phase was washed with 10 mL brine, dried over anhydrous sodium sulfate, concentrated, and purified by column chromatography to afford 1.02 g of a light yellow oil, yield was 50%. LC-MS(APCI): m/z=479$(M+1)^+$.

Step 4. Synthesis of (Z)-tert-butyl 3-(cyano(2-(4-phenoxyphenyl)hydrazono)methyl)piperidin-1-carboxylate (compound 19) (E)-tert-butyl 3-(1-cyano-2-methoxy-2-oxo-1-((4-phenoxyphenyl)diazenyl)ethyl)piperidin-1-carboxylate (1.0 g, 2.1 mmol) was dissolved in 20 mL tetrahydrofuran, cooled to 0° C. in an ice bath, 10N aqueous solution of sodium hydroxide (5 mL) was added, and stirred at room temperature for 1 hour. 30 mL saturated solution of ammonium chloride and 50 mL ethyl acetate were added, the layers were separated while stirring, the organic phase was washed with 10 mL brine, dried over anhydrous sodium sulfate, concentrated, and purified by column chromatography to afford 0.66 g of a light yellow oil, yield was 75%. LC-MS(APCI): m/z=421$(M+1)^+$.

Step 5. Synthesis of tert-butyl 3-(4-amino-5-cyano-1-(4-phenoxyphenyl)-1H-pyrazol-3-yl)piperidin-1-carboxylate (Compound 20)

(Z)-tert-butyl 3-(cyano (2-(4-phenoxyphenyl)hydrazono) methyl)piperidin-1-carboxylate (0.66 g, 1.6 mmol) and bromoacetonitrile (0.13 mL, 3.4 mmol) were dissolved in 10 mL tert-butyl alcohol, potassium tert-butoxide (0.54 g, 4.8 mmol) was added in portions at room temperature, and stirred at room temperature for 2 hours. 20 mL water and 40 mL ethyl acetate were added, the layers were separated while stirring, the organic phase was washed with 10 mL brine, dried over anhydrous sodium sulfate, concentrated, and purified by column chromatography to afford 0.5 g of a light yellow oil, yield was 70%. LC-MS(APCI): m/z=460 $(M+1)^+$.

Step 6. Synthesis of tert-butyl 3-(7-amino-(4-phenoxyphenyl)-1H-pyrazolo[4,3-d]pyrimidin-3-yl) piperidin-1-carboxylate (Compound 21)

Tert-butyl 3-(4-amino-5-cyano-1-(4-phenoxyphenyl)-1H-pyrazol-3-yl)piperidin-1-carboxylate (0.25 g, 0.55 mmol) was dissolved in 10 mL methanol, formamidine acetate (0.45 g, 4.4 mmol) was added, and the reaction was refluxed overnight. The reaction mixture was cooled to room temperature, concentrated to dry under reduced pressure, 20 mL saturated solution of sodium bicarbonate was added, and stirred for 5 minutes, extracted with ethyl acetate, the organic phase was washed with 10 mL brine, dried over anhydrous sodium sulfate, concentrated, and purified by column chromatography to afford 210 mg of a light yellow solid, yield was 80%. LC-MS(APCI): m/z=487$(M+1)^+$.

Step 7. Synthesis of 1-(4-phenoxyphenyl)-3-(piperidin-3-yl)-1H-pyrazolo[4,3-d]pyrimidin-7-amine (Compound 22)

Tert-butyl 3-(7-amino-(4-phenoxyphenyl)-1H-pyrazolo [4,3-d]pyrimidin-3-yl)piperidin-1-carboxylate (200 mg, 0.41 mmol) was dissolved in 10 mL dichloromethane, 4 mL trifluoroacetic acid was added, and stirred at room temperature for 1 hour. The reaction was concentrated to dry under reduced pressure, 20 mL dichloromethane and 15 mL saturated solution of sodium bicarbonate were added, stirred for 5 minutes, the layers were separated, the organic phase was washed with 5 mL brine, dried over anhydrous sodium sulfate, concentrated, and purified by column chromatography to afford 140 mg of a white solid, yield was 90%. LC-MS(APCI): m/z=387(M+1)$^+$.

Step 8. Synthesis of 1-(3-(7-amino-1-(4-phenoxyphenyl)-1H-pyrazolo[4,3-d]pyrimidin-3-yl)piperidin-1-yl)prop-2-en-1-one (Compound 23)

1-(4-phenoxyphenyl)-3-(piperidin-3-yl)-1H-pyrazolo[4,3-d]pyrimidin-7-amine (0.14 g, 0.36 mmol) was dissolved in 10 mL dichloromethane, cooled to −15° C., acryloyl chloride (32 mg, 0.36 mmol) was slowly added dropwise, and stirred for 10 minutes after the addition was complete. The ice bath was removed, and the reaction was continued for 1 hour. To the reaction mixture were added 10 mL water and 10 mL dichloromethane, the layers were separated while stirring, the organic phase was washed with 5 mL brine, dried over anhydrous sodium sulfate, concentrated, and purified by column chromatography to afford 116 mg of a white solid, yield was 73%. LC-MS(APCI): m/z=441(M+1)$^+$; $^1$H NMR (400 MHz, $CDCl_3$) δ 8.44 (d, J=11.8 Hz, 1H), 7.65-7.32 (m, 4H), 7.24-6.97 (m, 5H), 6.65 (dd, J=16.7, 10.3 Hz, 1H), 6.39-6.18 (m, 1H), 5.65 (dd, J=25.0, 10.8 Hz, 1H), 5.30 (s, 2H), 4.42-4.21 (m, 1H), 3.40 (d, J=10.8 Hz, 1H), 3.24 (dt, J=22.3, 12.2 Hz, 1H), 3.05-2.76 (m, 1H), 2.33 (d, J=13.7 Hz, 1H), 2.22-1.98 (m, 2H), 1.98-1.87 (m, 1H), 1.70 (d, J=13.2 Hz, 1H).

Example 3 Preparation of (S)-1-(3-(4-amino-5-(4-phenoxyphenyl)-5H-pyrrolo[3,2-d]pyrimidin-7-yl)piperidin-1-yl)prop-2-en-1-one (Compound 24)

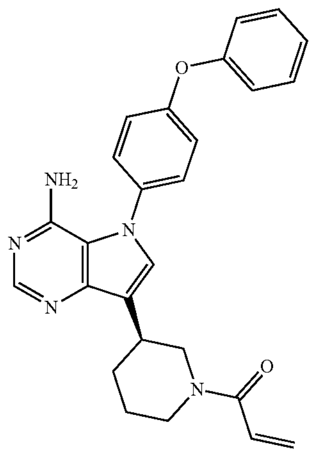 [SMILES: C=CC(=O)N1CCC[C@@H](c2cn(-c3ccc(Oc4ccccc4)cc3)c3c(N)ncnc23)C1]

Compound 24 was prepared according to the method of Example 1, and was obtained by chiral column separation.

Example 4 Preparation of (R)-1-(3-(4-amino-5-(4-phenoxyphenyl)-5H-pyrrolo[3,2-d]pyrimidin-7-yl)piperidin-1-yl)prop-2-en-1-one (Compound 25)

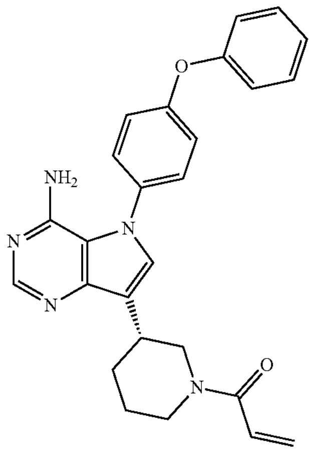 [SMILES: C=CC(=O)N1CCC[C@H](c2cn(-c3ccc(Oc4ccccc4)cc3)c3c(N)ncnc23)C1]

Compound 25 was prepared according to the method of Example 1, and was obtained by chiral column separation.

Example 5 Preparation of (R)-1-(3-(7-amino-1-(4-phenoxyphenyl)-1H-pyrazolo[4,3-d]pyrimidin-3-yl)piperidin-1-yl)prop-2-en-1-one (Compound 26)

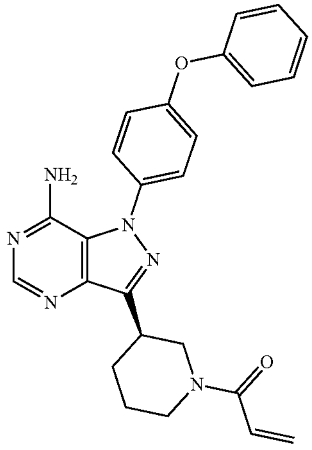 [SMILES: C=CC(=O)N1CCC[C@@H](c2nn(-c3ccc(Oc4ccccc4)cc3)c3c(N)ncnc23)C1]

Compound 26 was prepared according to the method of Example 2, and was obtained by chiral column separation.

Example 6 Preparation of (S)-1-(3-(7-amino-1-(4-phenoxyphenyl)-1H-pyrazolo[4,3-d]pyrimidin-3-yl)piperidin-1-yl)prop-2-en-1-one (Compound 27)
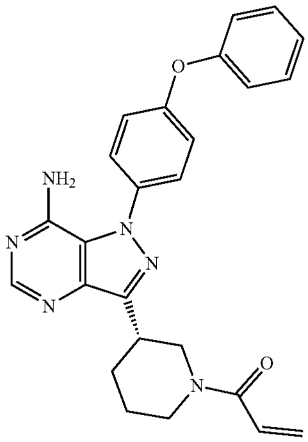 [SMILES: C=CC(=O)N1CCC[C@H](c2nn(-c3ccc(Oc4ccccc4)cc3)c3c(N)ncnc23)C1]
Compound 27 was prepared according to the method of Example 2, and was obtained by chiral column separation.
Example 7 Preparation of (S)-1-(3-(8-amino-1-(4-phenoxyphenyl)-1H-pyrazolo[4,3-d]pyrimidin-3-yl)piperidin-1-yl)prop-2-en-1-one (Compound 38)
38
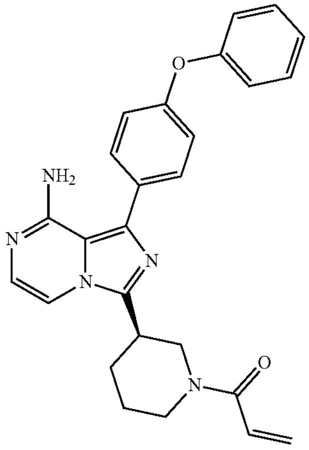
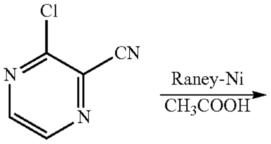
28
-continued
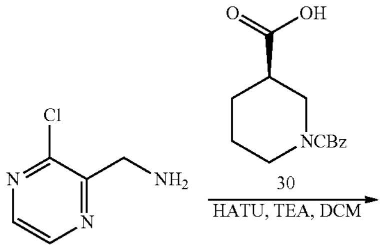
29
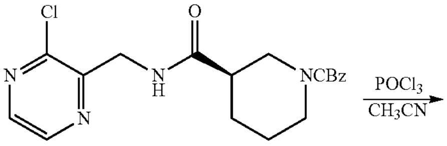
31
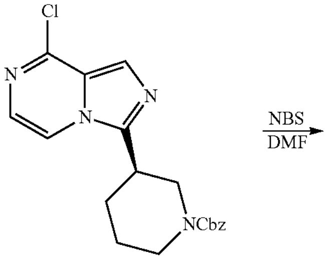
32
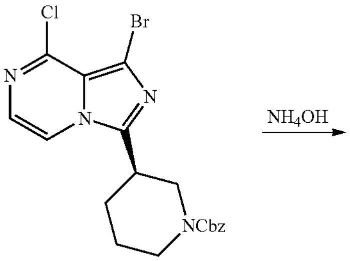
33
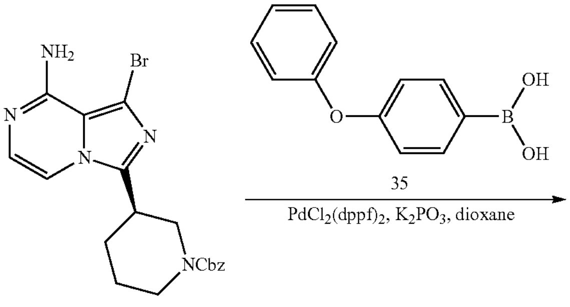
34

-continued

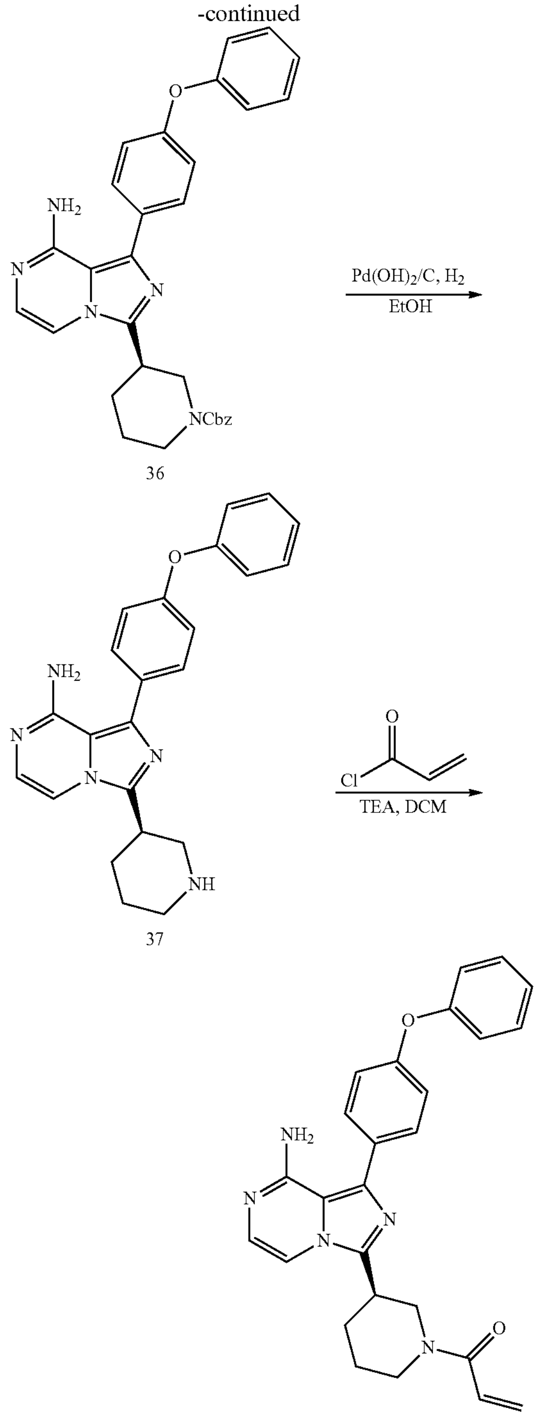

36

37

38

Step 1. Synthesis of (3-chloropyrazin-2-yl)methylamine (Compound 29)

2-cyano-3-chloropyrazine (0.8 g, 5.8 mmol) and Raney-Ni (0.3 g) were added to 10 mL glacial acetic acid, the atmosphere was replaced with hydrogen gas for three times, the mixture was stirred under 3 atmospheric pressure of hydrogen gas at 50° C. overnight. The reaction was filtered after the reaction was complete, filtrate was concentrated, the residue was dissolved in ethyl acetate, washed with saturated solution of sodium bicarbonate, dried over anhydrous sodium sulfate, concentrated, and separated by silica gel column to afford 0.5 g of a light yellow oil, yield was 60%. LC-MS(APCI): m/z=144(M+1)$^+$.

Step 2. Synthesis of (R)-benzyl 3-(((3-chloropyrazin-2-yl)methyl) carbamoyl)piperidin-1-carboxylate (Compound 31)

(3-chloropyrazin-2-yl)methylamine (0.3 g, 2.1 mmol), (R)-piperidin-1,3-dicarboxylate 1-benzyl (compound 30, 0.55 g, 2.1 mmol) and triethylamine (0.42 g, 4.2 mmol) were dissolved in 10 mL dichloromethane, under an ice bath 2-(7-azabenzotriazol)-N,N,N',N'-tetramethyluronium hexafluorophosphate (HATU, 0.84 g, 2.2 mmol) was added, and reacted at 0° C. for 1 hour. The reaction was warmed to room temperature naturally and reacted overnight. After the reaction was complete, the reaction mixture was washed sequentially with 0.1N hydrochloric acid, 5% $NaHCO_3$ and brine. The organic phase was dried over anhydrous sodium sulfate, concentrated, and separated by silica gel column to afford 0.5 g of a light yellow oil, yield was 62%. LC-MS (APCI): m/z=389(M+1)$^+$.

Step 3. Synthesis of (R)-benzyl 3-(8-chloroimidazo[1,5-a]pyrazin-3-yl)piperidin-1-carboxylate (Compound 32)

(R)-3-(((3-chloropyrazin-2-yl)methyl) carbamoyl)piperidin-1-carboxylate (0.49 g, 1.3 mmol) was dissolved in 10 mL anhydrous acetonitrile, phosphorus oxychloride (0.8 g, 5.2 mmol) was added, and the reaction was heated to 60° C., and reacted overnight. The solvent was evaporated after the reaction was complete, the residue was slowly added to ice-water, extracted with ethyl acetate (10 mL*3), the organic phase was washed with 10 mL brine, dried over anhydrous sodium sulfate, concentrated, and separated by silica gel column to afford 0.37 g of a light yellow solid, yield was 80%. LC-MS(APCI): m/z=371(M+1)$^+$.

Step 4. Synthesis of (R)-benzyl 3-(1-bromo-8-chloroimidazo[1,5-a]pyrazin-3-yl)piperidin-1-carboxylate (Compound 33)

(R)-benzyl 3-(8-chloroimidazo[1,5-a]pyrazin-3-yl)piperidin-1-carboxylate (0.37 g, 1.0 mmol) was dissolved in 10 mL DMF, N-bromosuccinimide (NBS, 0.21 g, 1.2 mmol) was added in portions under an ice bath, the reaction was warmed to room temperature naturally and reacted overnight. After the reaction was complete, 20 mL water was added to the reaction mixture, extracted with ethyl acetate (10 mL*3), the organic phase was washed with 10 mL brine, dried over anhydrous sodium sulfate, concentrated, and separated by silica gel column to afford 0.31 g of a light yellow solid, yield was 70%. LC-MS(APCI): m/z=449(M+1)$^+$.

Step 5. Synthesis of (R)-benzyl 3-(8-amino-1-bromoimidazo[1,5-a]pyrazin-3-yl)piperidin-1-carboxylate (Compound 34)

To a 50 mL scaled tube were added (R)-benzyl 3-(1-bromo-8-chloroimidazo[1,5-a]pyrazin-3-yl)piperidin-1-carboxylate (0.31 g, 0.7 mmol) and 10 mL concentrated ammonia, the reaction was heated to 120° C. in an oil bath and reacted overnight. The reaction was cooled to room temperature after the reaction was complete, the solvent was evaporated in a rotary evaporator, to afford 0.25 g of a white solid as powder, yield was 84%. LC-MS(APCI): m/z=430 $(M+1)^+$.

Step 6. Synthesis of benzyl (R)-3-(8-amino-1-(4-phenoxyphenyl) imidazo[1,5-a]pyrazin-3-yl)piperidin-1-carboxylate (Compound 36)

(R)-3-(8-amino-1-bromoimidazo[1,5-a]pyrazin-3-yl)piperidin-1-carboxylate (250 mg, 0.58 mmol) and (4-phenoxyphenyl) boronic acid (compound 35, 137 mg, 0.64 mmol), $PdCl_2(dppf)_2$ (110 mg, 0.15 mmol) and potassium carbonate (160 mg, 1.16 mmol) were added to 8 mL dioxane and 2 mL water, the atmosphere was replaced by nitrogen gas for three times, the reaction was heated to 90° C., and reacted overnight. The reaction was cooled to room temperature after the reaction was complete, 10 mL water was added, extracted with ethyl acetate (10 mL*3), the organic phase was washed with 10 mL brine, dried over anhydrous sodium sulfate, concentrated, and separated by silica gel column to afford 200 mg of a light yellow solid, yield was 66%. LC-MS(APCI): m/z=520$(M+1)^+$.

Step 7. Synthesis of (R)-1-(4-phenoxyphenyl)-3-(piperidin-3-yl) imidazo[1,5-a]pyrazin-8-amine (Compound 37)

(R)-benzyl 3-(8-amino-1-(4-phenoxyphenyl) imidazo[1,5-a]pyrazin-3-yl)piperidin-1-carboxylate (200 mg, 0.38 mmol) and 10% $Pd(OH)_2/C$ (40 mg) were added to 10 mL anhydrous ethanol, the atmosphere was replaced with hydrogen gas for three times, and the mixture was stirred under 3 atmospheric pressure of hydrogen gas at 50° C. overnight. The reaction was filtered after the reaction was complete, the filtrate was concentrated, and separated by silica gel column to afford 125 mg of a light yellow oil, yield was 85%. LC-MS(APCI): m/z=386$(M+1)^+$.

Step 8. Synthesis of (R)-1-(3-(8-amino-1-(4-phenoxyphenyl) imidazo[1,5-a]pyrazin-3-yl)piperidin-1-yl)prop-2-en-1-one (Compound 38)

(R)-1-(4-phenoxyphenyl)-3-(piperidin-3-yl) imidazo[1,5-a]pyrazin-8-amine (125 mg, 0.32 mmol) and triethylamine (50 mg, 0.48 mmol) were dissolved in 10 mL dichloromethane, cooled to −15° C., acryloyl chloride (29 mg, 0.32 mmol) was slowly added dropwise, and stirred for 10 minutes after the addition was complete. The ice bath was removed, and the reaction was continued for 1 hour. To the reaction mixture were added 10 mL water and 10 mL dichloromethane, the layers were separated while stirring, the organic phase was washed with 5 mL brine, dried over anhydrous sodium sulfate, concentrated, and purified by column chromatography to afford 100 mg of a white solid, yield was 70%. LC-MS(APCI): m/z=440$(M+1)^+$. $^1H$ NMR (400 MHz, $CDCl_3$) δ 8.41 (d, J=2.0 Hz, 1H), 8.26 (d, J=2.1 Hz, 1H), 7.66 (d, J=7.9 Hz, 2H), 7.50-7.38 (m, 2H), 7.26-7.07 (m, 5H), 6.79 (m, 1H), 6.10 (t, J=17.7 Hz, 1H), 5.65 (dd, J=36.5, 10.9 Hz, 1H), 4.65-4.40 (m, 1H), 4.25-3.65 (m, 2H), 3.08-2.91 (m, 2H), 2.25 (m, 1H), 2.11 (d, J=14.3 Hz, 1H), 1.93 (d, J=13.6 Hz, 1H), 1.60 (m, 1H).

Example 8 Preparation of (R)-1-(3-(4-amino-5-(4-phenoxyphenyl) imidazo[5,1-f][1,2,4]triazin-7-yl) piperidin-1-yl)prop-2-en-1-one (Compound 49)

49

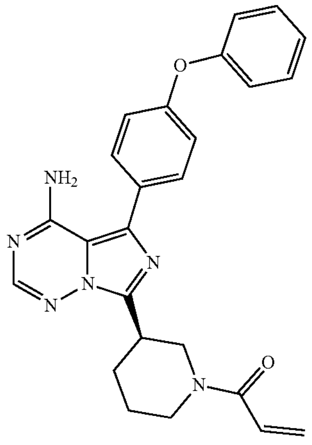

The specific synthetic steps are as follows:

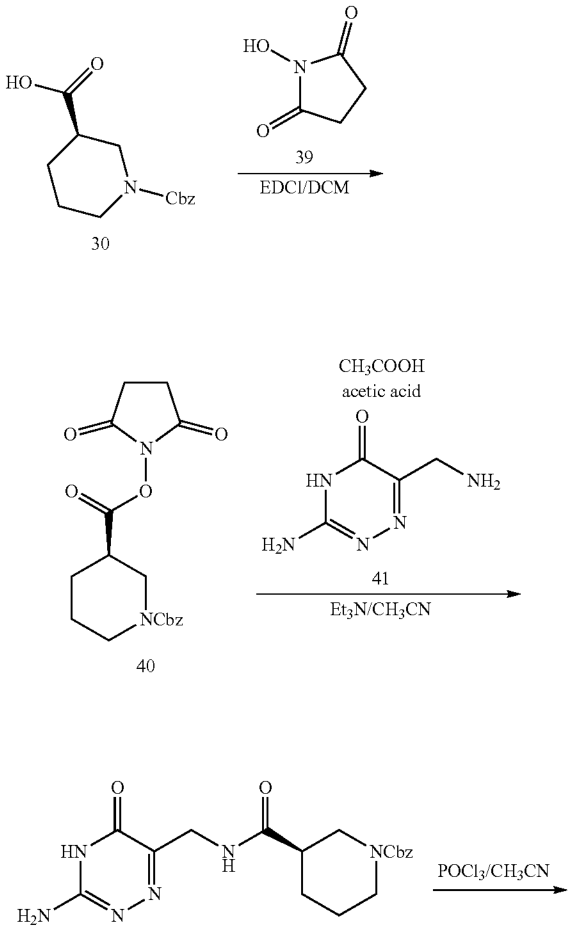

30 39 40 41 42

-continued

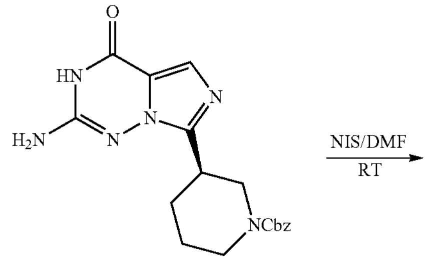

43

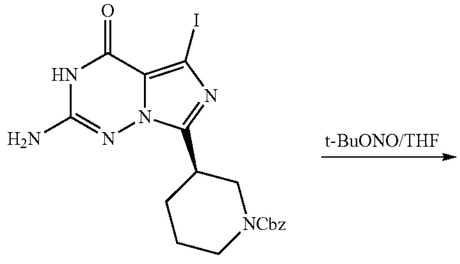

44

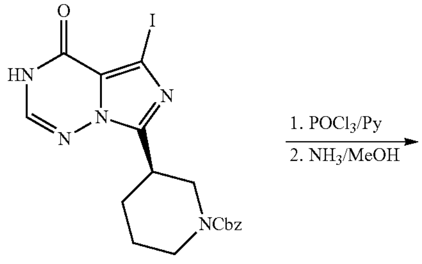

45

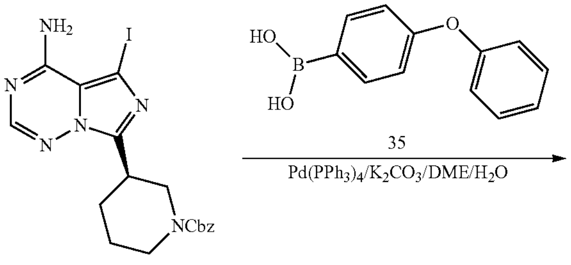

46

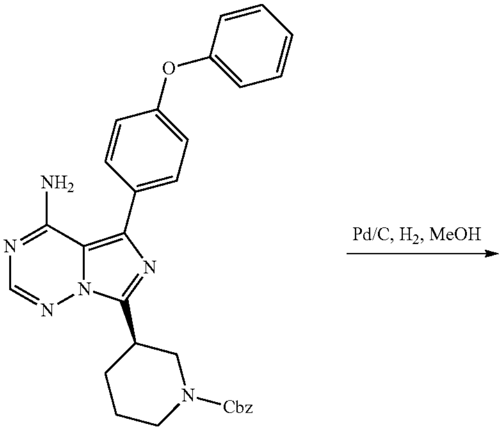

47

-continued

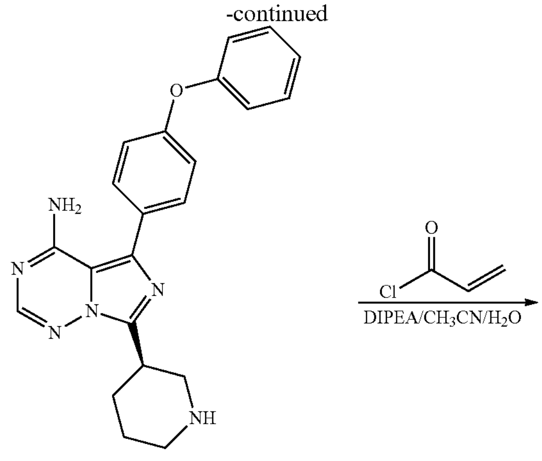

48

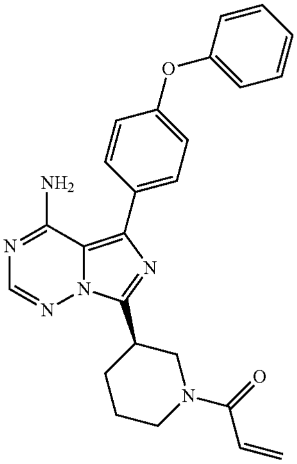

49

Step 1. Synthesis of 1-benzyl 3-(2,5-dioxopyrrolidin-1-yl)(R)-piperidine-1,3-dicarboxylate (Compound 40)

(R)-1-((benzyloxy) carbonyl)piperidine-3-carboxylic acid (4.0 g, 15.2 mmol), and 1-hydroxypyrrolidine-2,5-dione (1.92 g, 16.7 mmol) were added to 40 mL DCM, and the reaction was stirred and dissolved. Under an ice bath, the above reaction mixture was slowly added to 1-(3-Dimethylaminopropyl)-3-ethylcarbodiimide hydrochloride (3.79 g, 19.7 mmol). After the addition was completed, the cooling bath was removed, and the reaction was stirred under nitrogen protection at room temperature for 2 hours. The reaction was quenched by adding 60 mL water and additional 80 mL DCM, the organic layer was combined and washed with water (60 mL×2), dried over anhydrous $Na_2SO_4$, filtered and evaporated to dryness to afford 5.4 g of a yellow oil, yield was 98.5%. LC-MS(APCI): m/z=361.2 $(M+1)^+$.

Step 2. Synthesis of Benzyl (R)-3-(((3-amino-5-oxo-4,5-dihydro-1,2,4-triazin-6-yl)methyl) carbamoyl)piperidine-1-carboxylate (Compound 42)

1-benzyl 3-(2,5-dioxopyrrolidin-1-yl)(R)-piperidine-1,3-dicarboxylate (3.60 g, 10.0 mmol) and 3-amino-6-(aminomethyl)-1,2,4-triazin-5 (4H)-one (2.01 g, 10.0 mmol) were dissolved in 30 mL anhydrous $CH_3CN$, then $Et_3N$ (3.03 g, 30 mmol) was added, and the reaction mixture was heated to 50° C., and stirred under nitrogen protection until the reaction was completed. After cooling to room temperature, the solvent was removed under reduced pressure, water (60 mL) was added, and the mixture was stirred for 10 mins. The formed solid was filtered, washed with water (10 mL), oven dried to afford 2.55 g of a white solid, yield was 65.9%. LC-MS(APCI): m/z=387.3$(M+1)^+$.

Step 3. Synthesis of benzyl (R)-3-(2-amino-4-oxo-3,4-dihydroimidazo[5,1-f][1,2,4]triazin-7-yl)piperidine-1-carboxylate (Compound 43)

Benzyl (R)-3-(((3-amino-5-oxo-4,5-dihydro-1,2,4-triazin-6-yl)methyl) carbamoyl)piperidine-1-carboxylate (2.50 g, 6.47 mmol) was added into 15 mL anhydrous $CH_3CN$, stirred evenly, $POCl_3$ (1.98 g, 12.94 mmol) was added, and the reaction mixture was heated to reflux under nitrogen protection for 4 hours. After cooling to room temperature, it was concentrated to dry under reduced pressure, DCM (50 mL) and saturated $NaHCO_3$ (aq, 20 mL) were added and stirred for 10 mins, the organic layer was separated and the aqueous layer was extracted with DCM (30 mL×2), the organic phase was combined and dried over anhydrous $Na_2SO_4$, filtered and concentrated, and purified by flash column chromatography, to afford 920 mg of a white solid, yield was 38.6%. LC-MS(APCI): m/z=369.5$(M+1)^+$.

Step 4. Synthesis of Benzyl (R)-3-(2-amino-5-iodo-4-oxo-3,4-dihydroimidazo[5,1-f][1,2,4]triazin-7-yl) piperidine-1-carboxylate (Compound 44)

Benzyl (R)-3-(2-amino-4-oxo-3,4-dihydroimidazo[5,1-f][1,2,4]triazin-7-yl)piperidine-1-carboxylate (0.90 g, 2.44 mmol) was dissolved in 10 mL DMF, stirred evenly, NIS (0.60 g, 2.69 mmol) was added, and the reaction mixture was stirred under nitrogen protection at room temperature for 1 hour. The reaction mixture was poured in 30 mL water, extracted with ethyl acetate (40 mL×2), the organic phase was combined, washed with saturated NaCl (aq, 80 mL×3), dried over anhydrous $Na_2SO_4$, filtered and concentrated, and purified by flash column chromatography to afford 1.2 g of a white solid, yield was 91.2%. LC-MS(APCI): m/z=495.1 $(M+1)^+$.

Step 5. Synthesis of Benzyl (R)-3-(5-iodo-4-oxo-3,4-dihydroimidazo[5,1-f][1,2,4]triazin-7-yl)piperidine-1-carboxylate (Compound 45)

Benzyl (R)-3-(2-amino-5-iodo-4-oxo-3,4-dihydroimidazo[5,1-f][1,2,4]triazin-7-yl)piperidine-1-carboxylate (0.90 g, 1.82 mmol) was dissolved in 20 mL anhydrous THF, stirred evenly, cooled in an ice-water bath, and tert-butyl nitrite (0.37 g, 3.64 mmol) was slowly added. After the addition was complete, the cooling bath was removed, and the reaction mixture was stirred under nitrogen protection at room temperature overnight. The solvent was removed under reduced pressure, the residue was purified by flash column chromatography to afford 0.75 g of a white solid, yield was 86.0%. LC-MS(APCI): m/z=480.1$(M+1)^+$.

Step 6. Synthesis of benzyl (R)-3-(4-amino-5-iodoimidazo[5,1-f][1,2,4]triazin-7-yl) piperidine-1-carboxylate (Compound 46)

To a 50 mL three-neck flask was added 1,2,4-triazole (0.60 g, 8.76 mmol) and pyridine (7.3 mL), which was stirred and cooled in an ice-water bath, $POCl_3$ (0.45 g, 2.92 mmol) was added. After the addition was complete, the reaction was stirred under nitrogen protection for 20 mins, then the solution of benzyl (R)-3-(5-iodo-4-oxo-3,4-dihydroimidazo[5,1-f][1,2,4]triazin-7-yl)piperidine-1-carboxylate (0.70 g, 1.46 mmol) in pyridine (7.3 mL) was slowly dropped, and stirred at room temperature overnight. After cooling to −10° C., $NH_3$ in MeOH (7 M, 21.9 mmol, 3.13 mL) was slowly dropped into the reaction, and the reaction was stirred for 1 hour, concentrated to dryness, and purified by flash column chromatography to afford 0.56 g of a white solid, yield was 80.0%. LC-MS(APCI): m/z=479.1$(M+1)^+$.

Step 7. Synthesis of benzyl (R)-3-(4-amino-5-(4-phenoxyphenyl) imidazo[5,1-f][1,2,4]triazin-7-yl) piperidine-1-carboxylate (Compound 47)

Benzyl (R)-3-(4-amino-5-iodoimidazo[5,1-f][1,2,4]triazin-7-yl)piperidine-1-carboxylate (0.5 g, 1.04 mmol), (4-phenoxyphenyl) boronic acid (0.25 g, 1.15 mmol), $K_2CO_3$ (0.34 g, 2.5 mmol), DME (5 mL), $H_2O$ (1 mL) and $Pd(PPh_3)_4$ (0.11 g, 0.10 mmol) were added into a 50 mL one-neck flask, flushed with nitrogen gas for three times, and under nitrogen protection, the reaction was heated to 100° C., and stirred for 4 hours. After cooling to room temperature, the solvent was removed and the residue was purified by flash column chromatography to afford 0.46 g of a white solid, yield was 85.0%. LC-MS(APCI): m/z=521.1$(M+1)^+$.

Step 8 Synthesis of (R)-5-(4-phenoxyphenyl)-7-(piperidin-3-yl) imidazo[5,1-f][1,2,4]triazin-4-amine (Compound 48)

Benzyl (R)-3-(4-amino-5-(4-phenoxyphenyl)-imidazo[5,1-f][1,2,4]triazin-7-yl)piperidine-1-carboxy late (0.4 g, 0.77 mmol) was dissolved in 5 mL MeOH, Pd/C (50 mg, 10%) was added, the atmosphere was replaced with hydrogen gas for three times, and the mixture was stirred under 1 atmospheric pressure of hydrogen gas for 3 hours. Pd/C was filtered off, filtrate was washed with MeOH (5 mL), concentrated to dryness to afford 0.30 g of a brown oil, yield was 100%. LC-MS(APCI): m/z=387.2$(M+1)^+$.

Step 9. Synthesis of (R)-1-(3-(4-amino-5-(4-phenoxyphenyl) imidazo[5,1-f][1,2,4]triazin-7-yl)piperidin-1-yl)prop-2-en-1-one (Compound 49)

(R)-5-(4-phenoxyphenyl)-7-(piperidin-3-yl) imidazo[5,1-f][1,2,4]triazin-4-amine (0.3 g, 0.77 mmol) was dissolved in $CH_3CN$ (5 mL) and $H_2O$ (2 mL), DIPEA (0.2 g, 1.54 mmol) was added, cooled in an ice-water bath, the solution of acryloyl chloride (90 mg, 1.0 mmol) in $CH_3CN$ (1 mL) was slowly dropped into the above reaction. The cooling bath was removed, and the reaction was stirred at room temperature for 1 hours. Ethyl acetate (30 mL) and saturated NaCl (aq, 10 mL) was added, the organic layer was separated and the aqueous layer was extracted with ethyl acetate (15 mL×2), combined and dried over anhydrous $Na_2SO_4$, filtered and concentrated, the residue was purified by flash column chromatography to afford 0.21 g of a white solid, yield was 62.0%. LC-MS(APCI): m/z=441.1$(M+1)^+$. $^1H$ NMR (400 MHz, DMSO-$D_6$) δ/ppm: 8.23 (br s, 1H), 7.93 (s, 1H), 7.62 (d, J=7.2 Hz, 1H), 7.44-7.34 (m, 2H), 7.19-7.02 (m, 5H), 6.88-6.70 (m, 1H), 6.46 (br s, 1H), 6.13-6.01 (m, 1H), 5.70-5.56 (m, 1H), 4.62 (d, J=12.0 Hz, 0.5H), 4.20 (d, J=12.0 Hz, 2H), 4.06 (d, J=12.0 Hz, 0.5H), 3.54 (t, J=12.0 Hz, 0.5H), 3.19 (t, J=12.0 Hz, 0.5H), 3.09-2.99 (m, 1H), 2.20-2.13 (m, 1H), 2.02-1.86 (m, 2H), 1.55-1.52 (m, 1H).
Example 9 Preparation of 1-(3-(4-amino-5-(4-phenoxyphenyl) pyrrolo[2,1-f][1,2,4]triazin-7-yl)piperidin-1-yl)prop-2-en-1-one (Compound 58)
58
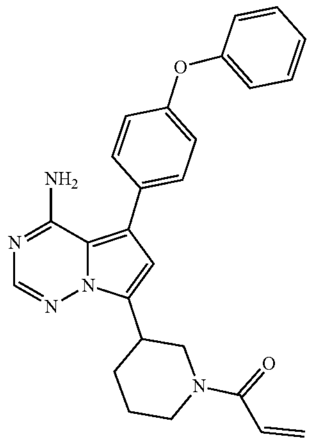
The specific synthetic steps are as follows:
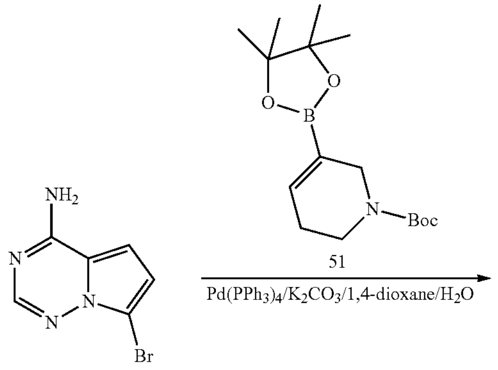
50
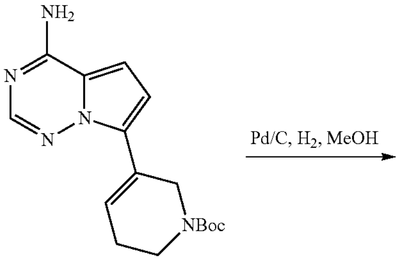
52
-continued
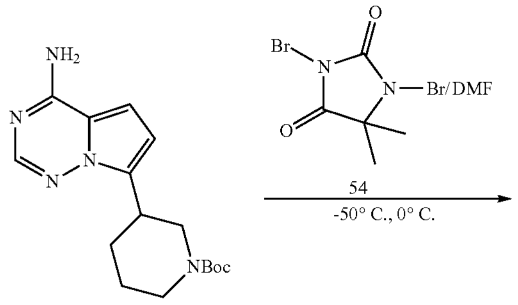
53
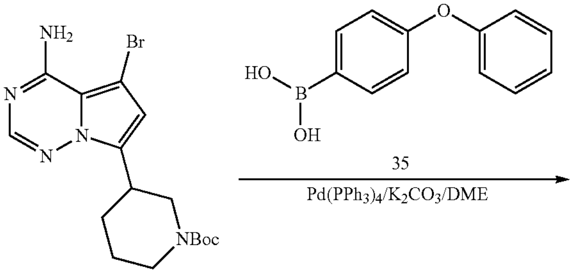
55
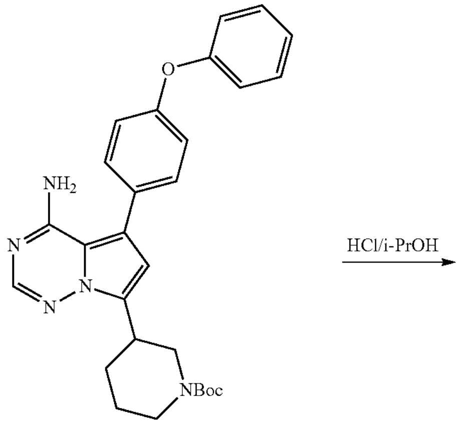
56
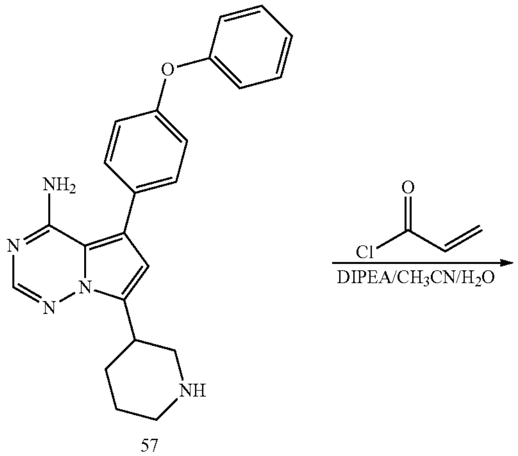
57

-continued

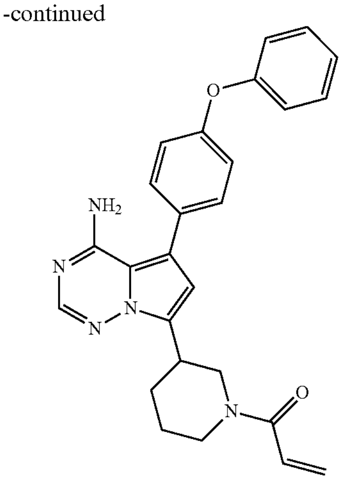

58

Step 1. Synthesis of tert-butyl 3-(4-aminopyrrolo[2,1-f][1,2,4]triazin-7-yl)-5,6-dihydropyridine-1 (2H)-carboxylate (Compound 52)

7-Bromopyrrolo[2,1-f][1,2,4]triazin-4-amine (22.64 mmol, 4.82 g), tert-butyl 3-(4,4,5,5-tetramethyl-1,3,2-dioxaborolan-2-yl)-5,6-dihydropyridine-1 (2H)-carboxylate (22.64 mmol, 7.00 g), potassium carbonate (56.6 mmol, 7.81 g) was dissolved in 1,4-dioxane (80 mL) and water (20 mL), then tetrakis(triphenylphosphine) palladium (0)(2.26 mmol, 2.51 g) was added, flushed with nitrogen gas for three times, and under nitrogen protection, the reaction mixture was heated to 100° C., and stirred for 4 hours. After cooling to room temperature, the reaction was filtered to remove the insoluble solid, the filtrate was concentrated and purified by flash column chromatography to afford 3.58 g of a white solid, yield was 50.2%. LC-MS(APCI): m/z=316.2$(M+1)^+$.

Step 2. Synthesis of tert-butyl 3-(4-aminopyrrolo[2,1-f][1,2,4]triazin-7-yl)piperidine-1-carboxylate (Compound 53)

Tert-butyl 3-(4-aminopyrrolo[2,1-f][1,2,4]triazin-7-yl)-5,6-dihydropyridine-1 (2H)-carboxylate (3.5 g, 11.1 mmol) was dissolved in 600 mL MeOH, TFA (4.3 mL) and water (2.0 mL) was added, then Pd/C (3.5 g, 10%) was added, the atmosphere was replaced with hydrogen gas for three times, and the mixture was stirred under 1 atmospheric pressure of hydrogen gas overnight. The Pd/C was filtered off, filtrate was washed with MeOH (20 mL), concentrated to dryness to afford 3.5 g of a white solid, yield was 99.9%. LC-MS (APCI): m/z=318.2$(M+1)^+$.

Step 3. Synthesis of tert-butyl 3-(4-amino-5-bromopyrrolo[2,1-f][1,2,4]triazin-7-yl)piperidine-1-carboxylate (Compound 55)

To a 250 mL three-neck flask was added tert-butyl 3-(4-aminopyrrolo[2,1-f][1,2,4]triazin-7-yl)piperidine-1-carboxylate (3.5 g, 11.1 mmol) and DMF (70 mL), which was stirred and cooled to −50° C. under nitrogen protection, 1,3-dibromo-5,5-dimethylimidazolidine-2,4-dione (1.58 g, 5.55 mmol) in DMF (10 mL) was slowly dropped. After the addition was complete, the reaction was slowly warmed to 0° C. and stirred at 0° C. for 1.5 hours. The reaction was quenched by adding 80 mL water and 80 mL ethyl acetate, the aqueous layer was extracted with ethyl acetate (50 mL×2), the organic phase was combined and washed with saturated NaCl (aq., 150 mL×3), dried over anhydrous $Na_2SO_4$, filtered and concentrated, and purified by flash column chromatography to afford 3.2 g of a white solid, yield was 73.0%. LC-MS(APCI): m/z=396.1$(M+1)^+$.

Step 4. Synthesis of tert-butyl 3-(4-amino-5-(4-phenoxyphenyl) pyrrolo[2,1-f][1,2,4]triazin-7-yl) piperidine-1-carboxylate (Compound 56)

Tert-butyl 3-(4-amino-5-bromopyrrolo[2,1-f][1,2,4]triazin-7-yl)piperidine-1-carboxylate (3.0 g, 7.60 mmol), (4-phenoxyphenyl) boronic acid (1.79 g, 8.35 mmol), $K_2CO_3$ (2.62 g, 19.0 mmol), DME (40 mL), $H_2O$ (10 mL) and $Pd(PPh_3)$ 4 (0.88 g, 0.76 mmol) were added into a 250 mL one-neck flask, flushed with nitrogen gas for three times, and under nitrogen protection, the reaction mixture was heated to 100° C., and stirred overnight. After cooling to room temperature, ethyl acetate (80 mL) was added, the reaction was filtered to remove the insoluble solid, and the filtrate was washed with ethyl acetate (10 mL), concentrated to dryness, and purified by flash column chromatography to afford a white solid 2.6 g of a white solid, yield was 70.5%. LC-MS(APCI): m/z=486.1$(M+1)^+$.

Step 5. Synthesis of 5-(4-phenoxyphenyl)-7-(piperidin-3-yl) pyrrolo[2,1-f][1,2,4]triazin-4-amine Hydrogen Chloride (Compound 57)

Under nitrogen protection, tert-butyl 3-(4-amino-5-(4-phenoxyphenyl) pyrrolo[2,1-f][1,2,4]triazin-7-yl)piperidine-1-carboxylate (2.5 g, 5.15 mmol) and 5 M HCl in i-PrOH (40 mL) were stirred at room temperature for 2 hours. The solvent was removed under reduced pressure, then MTBE (50 mL) was added, and the mixture was stirred for 10 mins. The formed suspension was filtered, washed with MTBE (5 mL), oven dried to afford 1.96 g of a white solid, yield was 90.7%. LC-MS (APCI): m/z=386.2$(M+1)^+$.

Step 6. Synthesis of 1-(3-(4-amino-5-(4-phenoxyphenyl) pyrrolo[2,1-f][1,2,4]triazin-7-yl)piperidin-1-yl)prop-2-en-1-one (Compound 58)

5-(4-phenoxyphenyl)-7-(piperidin-3-yl) pyrrolo[2,1-f][1,2,4]triazin-4-amine hydrogen chloride (1.9 g, 4.51 mmol) was dissolved in $CH_3CN$ (30 mL) and $H_2O$ (10 mL), DIPEA (1.74 g, 13.5 mmol) was added, cooled in an ice-water bath, the solution of acryloyl chloride (446 mg, 4.96 mmol) in $CH_3CN$ (3 mL) was slowly dropped into the above reaction. The cooling was removed, and the reaction was stirred at room temperature for 1 hour. Ethyl acetate (80 mL) and saturated NaCl (aq, 50 mL) was added, the organic layer was separated and the aqueous layer was extracted by ethyl acetate (30 mL×2), combined and dried by anhydrous $Na_2SO_4$, filtered and concentrated, the residue was purified by flash column chromatography to afford 1.2 g of a white solid, yield was 60.4%. LC-MS(APCI): m/z=440.1$(M+1)^+$. $^1H$ NMR (400 MHz, DMSO-$D_6$) δ/ppm: 7.93 (d, J=10.4 Hz, 1H), 7.47-7.40 (m, 4H), 7.18 (t, J=7.2 Hz, 1H), 7.13-7.09 (m, 4H), 6.90-6.76 (m, 1H), 6.61 (s, 1H), 6.14-6.08 (m, 1H), 5.67 (t, J=13.2 Hz, 1H), 4.63 (d, J=14.0 Hz, 0.5H), 4.36-4.28 (m, 1H), 4.05 (d, J=14.0 Hz, 0.5H), 3.31-3.27 (m, 2H), 2.95-2.86 (m, 1H), 2.24-2.12 (m, 1H), 1.87-1.79 (m, 2H), 1.54-1.52 (m, 1H).

Example 10 Preparation of (R)-1-(3-(4-amino-5-(4-phenoxyphenyl) imidazo[5,1-f][1,2,4]triazin-7-yl) piperidin-1-yl)prop-2-en-1-one (Compound 59)

59

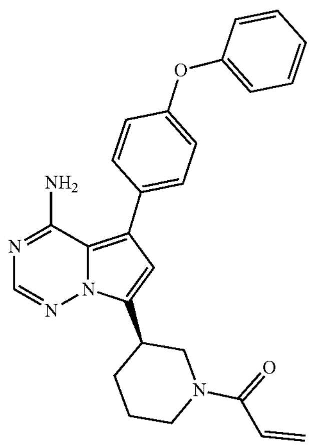

Chiral column: CHIRALPAK IC;

Mobile phase: MTBE:Hexane:MeOH=13:70:5:12

UV detection wavelength: 254 nm

With the above chiral column and chiral resolution conditions, the racemic compound 58 was dissolved in MeOH (50 mL) and separated to afford 550 mg of compound 59 (retention time: 26.195 min)

Example 11 Preparation of (S)-1-(3-(4-amino-5-(4-phenoxyphenyl) imidazo[5,1-f][1,2,4]triazin-7-yl) piperidin-1-yl)prop-2-en-1-one (Compound 60)

60

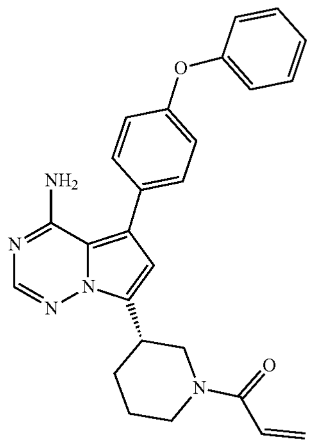

Chiral column: CHIRALPAK IC;

Mobile phase: MTBE:Hexane:MeOH=13:70:5:12

UV detection wavelength: 254 nm

With the above chiral column and chiral resolution conditions, the racemic compound 58 was dissolved in MeOH (50 mL) and separated to afford 550 mg of compound 60 (retention time: 28.892 min).

BIOLOGICAL ACTIVITY ASSAY (1) Kinase Inhibition Test

Reagents and Materials:

BTK (Invitrogen, catalog number: PR5442A), HTRF-TK kit (Cisbio, catalog number: 62TK0PEC), $MgCl_2$ (SIGMA, catalog number: 63020-1L), ATP (Sigma, catalog number: A7699-1G), DMSO (Sigma, catalog number: D2650), BSA (Sigma, catalog number: V900933), 384-well plate (compound dilution plate)(Greiner, catalog number: 781280), 384-well plate (test plate)(Perkin Elmer, catalog number: 6007299); XL-665 (CIS Bio International, catalog number: 610SAXL).

Experimental Procedures

1) Compound dilution: The test compounds were dissolved in DMSO to make a 10 mM stock solution. Compounds were diluted to 1 mM in DMSO prior to use, and serially diluted (3-fold) in 384 well plates for a total of 11 concentrations, with final concentrations ranging from 10 μM to 0.17 nM.
2) Kinase assay: in a 10 μL reaction system (containing buffer 50 mM Hepes (pH 7.5), 5 mM $MgCl_2$, 0.01 mM $Na_3VO_4$, 1% BSA) in a 384-well plate, 1 nM BTK, 1 μM biotin-TK peptide (from HTRF-TK kit) and 20 μM ATP were incubated at 23° C. for 90 minutes. 10 μL stop solution containing 20 mM EDTA, 1.67 nM TK antibody, 62.5 nM XL-665 was added and incubated at 23° C. for 60 minutes, then read with Envision.
3) $IC_{50}$ value calculation: The inhibition rate of the compound was calculated from the data read by the instrument, and then the $IC_{50}$ value was calculated using the mode 205 of XLFIT5 of IDBS.

Experimental Results

The results of the kinase inhibition in the examples are summarized in Table 1 below, and the results of the experiments indicate that the compounds disclosed herein are potent inhibitors of BTK kinase activity.

TABLE 1

| Kinase inhibition | | |
|---|---|---|
| Example No. | BTK $IC_{50}$(nM) | RAMOS $IC_{50}$(nM) |
| Example 3 | <1 | <100 |
| Example 4 | <1 | <100 |
| Example 5 | <1 | <100 |
| Example 6 | <1 | <100 |
| Example 7 | <1 | <100 |
| Example 8 | <1 | |
| Example 10 | <1 | |
| Ibrutinib | <1 | <100 |

(2) Metabolic Stability Evaluation

Experiments in Microsome

Reagents and Materials:

Human liver microsomes (0.5 mg/mL, Xenotech, catalog number: H0610); rat liver microsomes (0.5 mg/mL, Xenotech, catalog number: R1000); coenzyme (NADPH/NADH) (1 mM, Sigma Life Science); D-glucose-6-phosphate sodium salt (G-6-P, Aladdin, catalog number: G111871-5 g); glucose-6-phosphate dehydrogenase (G-6-P D, Sigma Life Science, catalog number: G6378-250UM); magnesium chloride (5 mM), propranolol hydrochloride (Sigma, catalog number: P0884-1G); tolbutamide (Sigma Life Science, catalog number: T0891); 100 mM phosphate buffer (pH 7.4); 96-well plate mixer (IKA, model: MTS 2/4 digital); 96-well deep well plate (Doublehelix Biology Science and Technology Co., Ltd, 2.2 mL); 96-well incubator plate (Doublehelix Biology Science and Technology Co., Ltd, 2.2 mL).

Experimental Procedures

1) Preparation of stock solutions: Powder of the compounds of Examples 3-7 and Ibrutinib were accurately weighed and separately dissolved in DMSO to a concentration of 5 mM.
2) Preparation of phosphate buffer (100 mM, pH 7.4): 150 mL of pre-formulated 0.5 M potassium dihydrogen phosphate was taken and mixed with 700 mL of 0.5 M dipotassium hydrogen phosphate solution, and the pH of the mixture was adjusted to 7.4 with 0.5 M dipotassium hydrogen phosphate solution. Before use it was diluted by 5 times with ultrapure water, and magnesium chloride was added to obtain the phosphate buffer (100 mM), which contains 100 mM potassium phosphate, 3.3 mM magnesium chloride, and a pH of 7.4.
3) Preparation of NADPH: A reconstituted system solution (containing 6.5 mM NADPH, 16.5 mM G-6-P, 3 U/mL G-6-P D, 3.3 mM magnesium chloride) was prepared and placed on wet ice prior to use.
4) Preparation of stop solution: The stop solution was an acetonitrile solution containing 50 ng/mL propranolol hydrochloride and 200 ng/mL tolbutamide (internal standard).
5) Preparation of liver microsome dilution: 25057.5 μL phosphate buffer (pH 7.4) was taken and placed into a 50 mL centrifuge tube, 812.5 μL human liver microsomes was added, and evenly mixed to obtain liver microsomes dilution with a protein concentration of 0.625 mg/mL. 25057.5 μL of phosphate buffer (pH 7.4) was taken and placed into a 50 mL centrifuge tube, 812.5 μL of SD rat liver microsomes was added, and evenly mixed to obtain a liver microsome dilution with a protein concentration of 0.625 mg/mL.
6) Incubation of the sample: The stock solutions of the corresponding compounds were diluted to 0.25 mM with an aqueous solution containing 70% acetonitrile, which is used as a working solution and is ready for use. 398 μL of human liver microsomes dilution or rat liver microsome dilution was added to 96-well incubation plates (N=2), and 2 μL of 0.25 mM working solutions were added respectively, and evenly mixed.
7) Determination of metabolic stability: 300 μL of pre-cooled stop solution was added to each well of a 96-well deep well plate, which was placed on ice as a stop plate. The 96-well incubation plate and the NADPH regeneration system were placed in a 37° C. water bath, shaken at 100 rpm, and pre-incubated for 5 min. 80 μL of the incubation solution was taken from each well of the incubation plate, added to the stop plate, evenly mixed, and 20 μL of the NADPH regeneration system solution was added as 0 minute sample. Then, 80 μL of the NADPH regeneration system solution was added to each well of the incubation plate to start the reaction and start timing. The corresponding compound had a reaction concentration of 1 μM and a protein concentration of 0.5 mg/mL. 100 μL of the reaction solutions were taken at 10, 30, and 90 min, respectively, added to the stop place, and the reaction was terminated by vortexing for 3 min. The plate was centrifuged at 5000×g for 10 min at 4° C. 100 μL of the supernatant was taken and added into a 96-well plate to which 100 μL of distilled water was previously added, evenly mixed, and samples were analyzed by LC-MS/MS.
8) Data analysis: The peak area of the corresponding compounds and the internal standard was detected by LC-MS/MS system, and the ratio of the peak area of the compounds to the internal standard was calculated. The slope is measured by plotting the natural logarithm of the percentage of the remaining amount of the compounds versus time, and tin and $CL_{int}$ were calculated according to the following formula, where V/M is equal to 1/protein concentration.

$$t_{1/2} = -\frac{0.693}{\text{slope}},\ CL_{int} = \frac{0.693}{t_{1/2}} \cdot \frac{V}{M}$$

Experimental Results

The experimental results are shown in Table 2 below. Compared with Ibrutinib, the compounds disclosed herein have improved metabolic stability in human liver microsomes and rat liver microsomes, indicating the metabolic stability of the drug is improved.

TABLE 2

Evaluation of liver microsomes metabolism of the Example compounds

| | Human liver microsomes experiment | | Rat liver microsomes experiment | |
|---|---|---|---|---|
| No. | $t_{1/2}$(min) | CLint (μL/min/mg) | $t_{1/2}$(min) | CLint(μL/min/mg) |
| Ibrutinib | 1.3 | 1096.0 | 1.1 | 1218.7 |
| Example 3 | 1.3 | 1097.9 | — | — |
| Example 4 | 3.5 | 399.2 | 2.9 | 483.3 |
| Example 5 | 1.5 | 921.8 | — | — |
| Example 6 | 12.5 | 111.1 | 4.1 | 337.8 |
| Example 7 | 5.7 | 242.6 | 2.4 | 576.3 |

(3) Pharmacokinetic Experiments in Rats

8 Male Sprague-Dawley rats, 7-8 weeks old and weight of 210 g, were divided into 2 groups, 4 rats in each group. They were intravenously given 0.5 mg/kg of and orally given 10 mg/kg single dose of (a) control group: reference compound; (b) test group: Example compounds. The pharmacokinetic differences were compared.

Rats were fed with a standard diet and water. Fasting began 16 hours before the test. The drug was dissolved with PEG400 and dimethyl sulfoxide. Blood was collected from the eyelids at a time point of 0.083 hour, 0.25 hour, 0.5 hour, 1 hour, 2 hours, 4 hours, 6 hours, 8 hours, 12 hours, and 24 hours after administration.

Rats were briefly anesthetized after inhalation of ether, and 300 μL of blood samples were collected from the eyelids and placed to test tubes, wherein there were 30 μL of 1% heparin salt solution in the test tube. The tubes were dried overnight at 60° C. before use. After the blood sample collection was completed at a later time point, the rats were anesthetized with ether and sacrificed.

Immediately after the blood samples were collected, the test tubes were gently inverted at least 5 times to ensure sufficient mixing, and were placed on ice. Blood samples were centrifuged at 5000 rpm for 5 minutes at 4° C. to separate plasma from red blood cells. 100 μL of the plasma was pipetted into a clean plastic centrifuge tube, marking the name of the compound and time of collection. Plasma was stored at −80° C. prior to analysis. The concentration of the compounds disclosed herein in plasma was determined by LC-MS/MS. Pharmacokinetic parameters were calculated based on the plasma concentration of each animal at different time points.

The compounds disclosed herein were tested in the above pharmacokinetic experiments in rats, and the compounds disclosed herein were found to have superior pharmacokinetic properties compared to Ibrutinib. The results of the pharmacokinetic experiments in rats of representative Example 7 and the control compound Ibrutinib are summarized in Table 3 below.

TABLE 3

Rat pharmacokinetic experiments of Example compounds

| | Ibrutinib | | Example 7 | |
|---|---|---|---|---|
| PK parameters | IV | PO | IV | PO |
| $T_{max}$ (h) | 0.08 | 0.50 | 0.08 | 0.67 |
| $C_{max}$ (ng/mL) | 1228.7 | 250.3 | 965.7 | 364.7 |
| AUC $_{last}$h*ng/mL) | 437.0 | 727.4 | 401.2 | 931.0 |
| F(%) | 16.65 | | 23.20 | |
| | **Example 8** | | **Example 10** | |
| PK parameters | IV | PO | IV | PO |
| $T_{max}$ (h) | | 0.333 | | 0.50 |
| $C_{max}$ (ng/mL) | 1115 | 348 | 647 | 29.7 |
| AUC $_{last}$h*ng/mL) | 255 | 820 | 156 | 68.4 |
| F(%) | 16.0 | | 2.31 | |

(4) BTK C481S and ITK Kinase Inhibition Test

Reagents and materials: BTK C481S (Carna, catalog number: 08-547), ITK (Carna, catalog number: 08-181). HTRF-TK kit (Cisbio, catalog number: 62TK0PEC), $MgCl_2$ (Sigma, catalog number: M1028), $MnCl_2$ (Sigma, catalog number: M1787), DTT (Sigma, catalog number: D0632), ATP (Sigma, catalog number: A7699-1 g), DMSO (Sigma, catalog number: D2650), 384 well plate (PE, catalog number: 6008280).

Kinase Assay: Stock solution of the test compounds were prepared. The final concentration of DMSO in the kinase detection system was not exceed 1%. All of the procedures were carried out on ice, and the total volume of the reaction is 10 μL. Compound (4 μL), substrate and ATP (4 μL), and kinase (2 μL) were added to the wells of a 384-well plate in sequence, shaked for 30 sec, and reacted at room temperature for a proper time. Then, the resection was stopped by adding the detection reagents. The reaction mixture was reacted at room temperature for 1 hr, and detected with Microplate Reader. Details of protocols are as follows:

a) The volume of 1× kinase buffer for use in the kinase detection was calculated based on the amount of the test compounds.
b) 2.5× working solution of the test compounds was prepared by 40× gradiently diluting the 100-fold stock solution to the desired concentration, mixed well, and added 4 μL to each well.
c) 5× working solution of the substrate and ATP were prepared, mixed well in a ratio of 1:1, and added to the wells of the 384-well plate, 4 μL per well.
d) 5× working solution of the kinase was prepared, and added 2 μL to each well.
e) The plate was shaked for 30 sec on a microplate shaker, sealed with a sealing film, and reacted at room temperature for a proper time.
f) 5× working solution of Streptavidin XL-665 and TK Antibody-Cryptate were prepared, mixed well in a ratio of 1:1, and added to the wells, 10 μL per well.
g) The plate was read after reacting at RT for 1 h.
h) Blank control and positive control wells were set, wherein the blank control wells only included substrate, ATP, 1% DMSO, without kinase, and the positive control wells included substrate, ATP, 1% DMSO and kinase.

Plate reading: The value of the emission signal at 665 nm (XL665) and 620 nm (Cryptate) was read using BioTek Synerg Neo2 microplate reader, and the ratio of values at 665/620 was calculate for each well.

Data Analysis: The $IC_{50}$ value was calculated with GraphPad Prism 7.0.

The $IC_{50}$ of the compounds was fit using the following formula.

$$Y=Bottom+(Top-Bottom)/(1+10\hat{}((Log\ IC_{50}-X)*HillSlope))$$

X: log value of compound concentration $$Y:\ Inhibition\ \%=(1-(Ratio_{test}-Ratio_{blank})/(Ratio_{positive}-Ratio_{blank}))*100\%$$

Experimental Results

The results of the kinase inhibition in the examples are summarized in Table 4 below, and the results of the experiments indicate that the compounds disclosed herein are superior potent inhibitors of BTK C481S kinase compared to Ibrutinib. Furthermore, the compounds disclosed herein are more selective than Ibrutinib with preferential inhibition of BTK C481S over ITK.

TABLE 4 results of the kinase inhibition.

| | BTK C481S $IC_{50}$ (nM) | ITK $IC_{50}$ (nM) |
|---|---|---|
| Ibrutinib | 5.05 | 30.47 |
| 3 | 10.70 | 139.00 |
| 5 | 6.02 | 619.00 |
| 6 | 16.10 | 4383.00 |
| 7 | 2.46 | 21.90 |
| 8 | 3.85 | 172.00 |
| 10 | 30.10 | 705.00 |

(5) Phospho-BTK (Y223) Assay

The Adherent Cells Protocol:

Day 1:

1. 7.5k/well of NIH/3T3 BTK WT cells and 10k/well of NIH/3T3 BTK C481S cells were seeded in a 96-well plate, respectively. The plate was incubated overnight at 37° C., 5% $CO_2$.

Day 2:

1. 3-fold compound dilution was prepared, and dispensed 50 μL into 100 μL cell culture. 0.5% DMSO was used as positive control of the cell growth.
2. The plate was incubated at 37° C., 5% $CO_2$ for 0.5 h.
3. 50 μL of 1 mM $Na_3VO_4$ was added, and incubated at 37° C., 5% $CO_2$ for 2 h.
4. During the incubation, the following reagents were prepared: 1× supplemented lysis buffer: 3 vol $ddH_2O$+1 vol 4× Lysis buffer+100× Blocking reagent. p-BTK (Y223) cryptate-antibody and p-BTK (Y223) d2-antibody working solution: 1 volume of the stock solution of each antibody frozen aliquot (stored at)−20° was added into 19 volumes of the detection buffer (stored at) 4°.

5. At the end of the incubation, the plate was flicked to remove the medium, then added 50 μL of 1× supplemented lysis buffer, and incubated at RT for 30 min, with 500 rpm shaking.
6. The lysate was homogenized by pipetting up and down, and transferred 16 μL to a 384-well microplate. 1× supplemented lysis buffer was used as blank control.
7. 4 μL of premixed antibody working solutions (cryptate Ab:d2 Ab=1:1) was added. The plate was covered with a plate sealer.
8. Incubated at RT overnight.

Day 3:

The emission signal at 665 nm and 620 nm was read using Biotek Cytation3.0 microplate reader and the ratio of values of 665/620 was calculated for each well.

Data Analysis:

The $IC_{50}$ value was calculated with GraphPad Prism 7.0.

The $IC_{50}$ of the compounds for phosphorylating BTK Y223 was fit using the following formula.

$$Y=Bottom+(Top-Bottom)/(1+10\hat{}((Log\ IC_{50}-X)*HillSlope))$$

X: log value of compound concentration $$Y{:}Inhibition\ \%=(1-(Ratio_{test}-Ratio_{blank})/(Ratio_{positive}-Ratio_{blank}))*100\%$$

The results of inhibition of the phosphor-BTK Y223 in the examples are summarized in Table 5 below.

TABLE 5 results of inhibition of the phosphor-BTK Y223

| Example No. | NIH/3T3 BTK-WT pBTK (IC50 nM) | NIH/3T3 BTK-C481S pBTK (IC50 nM) |
|---|---|---|
| Ibrutinib | 3.30 | 637.50 |
| 3 | 6.62 | 502.00 |
| 5 | 5.48 | 663.50 |
| 6 | 18.70 | >1000 |
| 7 | 7.36 | 162.50 |
| 8 | 4.86 | 291.50 |
| 10 | 13.20 | >1000 |

(6) Pharmacokinetics and Brain Distribution Study in Male Sprague Dawley Rats Following a Single Oral Administration This study is designed to evaluate the pharmacokinetics and brain distribution of compounds disclosed herein in male Sprague Dawley Rat following a single Oral administration.

Total 12 male SD Rats assigned to this study were orally dosed via gavage (3 rats per timepoint) with the compounds disclosed herein in 5% DMSO+15% Solutol HS 15+80% (20% Hp-β-CD in DW) at 10 mg/kg. The animals were fasted overnight from 18:00 p.m. before the dosing day, and fed at 4 hr post-dose. All animals were free access to water during the study. Blood, CSF and brain were collected after each occasion of dosing at 0.5, 1, 2, and 8 hr. Blood samples (~0.25 mL per time-point) were collected via jugular venous sinus puncture and placed in K2EDTA-containing tubes. Immediately following blood collection, the samples were inverted several times and held on wet ice before centrifugation. All the samples were centrifuged within 30 min of collection under refrigeration (set to maintain 4° C. for 5 min at 6000 rpm) to obtain plasma. The CSF samples (about 100 μL) were collected into tubes via puncture of the cisterna magna. The brain samples were rinsed with saline, drained with filter paper and removed with blood vessels, then weighted and recorded. 5-fold of the homogenate solvent (30% MeOH/70% 10 mM PBS) were used for the homogenization. All the samples were stored at −80° C., or lower until being analyzed with LC-MS/MS. Concentrations of the compounds disclosed herein in each matrix were used for PK analysis by non-compartmental method using WinNonlin.

The results of pharmacokinetics and brain distribution study in the examples were summarized in Table 6 below, and the results of the experiments indicate that the compounds disclosed herein had higher concentration in Brain and CSF of the rats.

TABLE 6 results of pharmacokinetics and brain distribution study

| | Example No. | | | | | |
|---|---|---|---|---|---|---|
| | Ibrutinib | | | Example 7 | | |
| | Plasma | Brain | CSF | Plasma | Brain | CSF |
| $T_{max}$ (h) | 0.5 | 0.5 | 0.5 | 0.5 | 0.5 | 0.5 |
| $C_{max}$ (ng/mL) | 251 | 25.4 | 0.35 | 117 | 18 | 0.478 |
| $AUC_{last}$ (h*ng/mL) | 626 | 28 | 0.0875 | 275 | 16.4 | 0.119 |
| $AUC_{INF\_pred}$ (h*ng/mL) | 666 | NA | NA | 285 | NA | NA |
| $MRT_{INF\_pred}$ (h) | 2.41 | NA | NA | 2.03 | NA | NA |
| $Vz_{\_pred}$ (L/kg) | 43 | NA | NA | 85.5 | NA | NA |
| $Cl_{\_pred}$ (L/h/kg) | 15 | NA | NA | 586 | NA | NA |
| $T_{1/2}$ (h) | 1.98 | NA | NA | 1.69 | NA | NA |

It is to be understood that the examples are merely illustrative of the invention and are not intended to limit the scope of the invention, and the experimental methods in which the specific conditions are not indicated, are carried out generally in accordance with conventional conditions, or in accordance with the conditions suggested by the manufacturer. Parts and percentages are parts by weight and percentage by weight unless otherwise stated.

The above is a further detailed description of the present disclosure in connection with the specific preferred embodiments, and the specific embodiments of the present disclosure are not limited to the description. It will be apparent to those skilled in the art that the present disclosure may be practiced by making various simple deduction and replacement, without departing from the spirit and scope of the invention.

The invention claimed is:

1. A method for inhibiting Bruton's tyrosine kinase (BTK) activity in a subject in need thereof, wherein the method comprises administering to the subject in need thereof a therapeutically effective amount of a compound of formula (IV):

(IV)

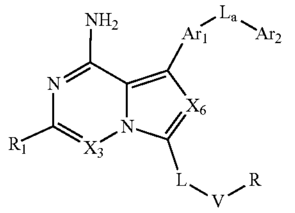

or a pharmaceutically acceptable salt or tautomer thereof, wherein:

$X_3$ is $CR_1$;

$X_6$ is N;

each $R_1$ is independently H;

$Ar_1$ is ring C of the formula:

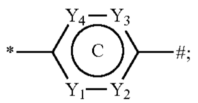

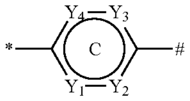

is:

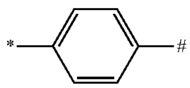 or 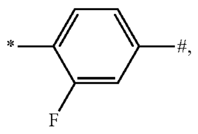

wherein * is the point of attachment to the carbon atom of the imidazo[1,5-a]pyrazine ring and # is the point of attachment to $L_a$;

$L_a$ is —O—;

$Ar_2$ is unsubstituted phenyl;

L is:

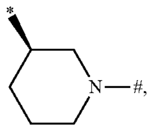

wherein * is the point of attachment to the carbon atom of the imidazo[1,5-a]pyrazine ring and # is the point of attachment to V;

V is —C(O)—; and

R is $C_2$-$C_4$ alkenyl;

wherein the subject has a multiple sclerosis.

2. The method of claim 1, wherein the Bruton's tyrosine kinase is the C481S mutant form of Bruton's tyrosine kinase.

3. The method of claim 1, wherein the therapeutically effective amount is a daily amount in the range of from 1 mg to 500 mg.

4. The method of claim 1, wherein the method further comprises once, twice, or three times daily administering to the subject in need thereof a therapeutically effective amount of the compound of formula (IV), or a pharmaceutically acceptable salt or tautomer thereof.

5. The method of claim 1, wherein the method further comprises twice daily administering to the subject in need thereof a therapeutically effective amount of the compound of formula (IV), or a pharmaceutically acceptable salt or tautomer thereof.

6. The method of claim 5, wherein the method further comprises twice daily administering to the subject in need thereof a therapeutically effective amount of the compound of formula (IV), or a pharmaceutically acceptable salt or tautomer thereof, at least eight hours between the first daily administration and the second daily administration.

7. The method of claim 1, wherein the method further comprises twice daily administering to the subject in need thereof a therapeutically effective amount of the compound of formula (IV), or a pharmaceutically acceptable salt or tautomer thereof, once in the morning and once in the evening.

8. The method of claim 1, wherein the method further comprises administering to the subject in need thereof a therapeutically effective amount of the compound of formula (IV), or a pharmaceutically acceptable salt or tautomer thereof, for a duration of at least one week.

9. The method of claim 1, wherein the method further comprises administering to the subject in need thereof a therapeutically effective amount of the compound of formula (IV), or a pharmaceutically acceptable salt or tautomer thereof, without eating food.

10. The method of claim 1, wherein the method further comprises administering to the subject in need thereof a therapeutically effective amount of the compound of formula (IV), or a pharmaceutically acceptable salt or tautomer thereof, within one hour prior to eating food.

11. The method of claim 1, wherein the method further comprises administering to the subject in need thereof a therapeutically effective amount of the compound of formula (IV), or a pharmaceutically acceptable salt or tautomer thereof, along with eating food.

12. The method of claim 1, wherein the method further comprises administering to the subject in need thereof a therapeutically effective amount of the compound of formula (IV), or a pharmaceutically acceptable salt or tautomer thereof, in a form selected from the group consisting of an aerosol, a capsule, an elixir, a pill, a powder, a semisolid, a solution, a suspension, a sustained release formulation, and a tablet.

13. The method of claim 1, wherein the method further comprises orally administering to the subject in need thereof a therapeutically effective amount of the compound of formula (IV), or a pharmaceutically acceptable salt or tautomer thereof.

14. The method of claim 1, wherein

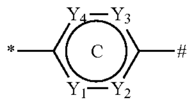

is:

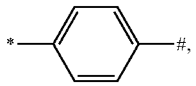

wherein * is the point of attachment to the carbon atom of the imidazo[1,5-a]pyrazine ring and # is the point of attachment to $L_a$.

15. The method of claim 1, wherein R is $CH{=}CH_2$.

16. The method of claim 1, wherein the compound is:

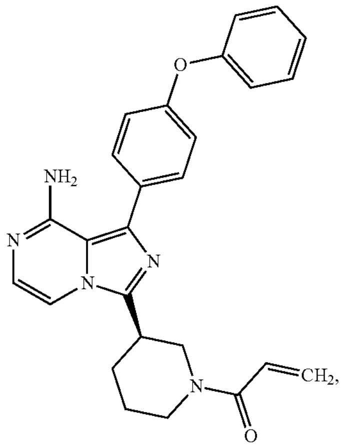 [SMILES: C=CC(=O)N1CCC[C@@H](c2nc(-c3ccc(Oc4ccccc4)cc3)c3c(N)nccn23)C1]

or a pharmaceutically acceptable salt or tautomer thereof.

17. The method of claim 1, wherein the multiple sclerosis is progressive multiple sclerosis (PMS) or relapsing multiple sclerosis (RMS).

18. The method of claim 1, wherein the progressive multiple sclerosis is primary-progressive multiple sclerosis (PPMS) or secondary-progressive multiple sclerosis (SPMS).

19. The method of claim 17, wherein the relapsing multiple sclerosis is progressive-relapsing multiple sclerosis (PRMS) or relapsing-remitting multiple sclerosis (RRMS).

* * * * *